United States Patent [19]
Takeuchi et al.

[11] Patent Number: 5,965,556
[45] Date of Patent: Oct. 12, 1999

[54] PYRROLIDINE DERIVATIVES

[75] Inventors: Tomio Takeuchi, Tokyo; Takaaki Aoyagi, Fujisawa; Yasuhiko Muraoka; Makoto Tsuda, both of Tokyo, all of Japan

[73] Assignee: Zaidan Hojin Biseibutsu Kagaku Kenkyukai, Tokyo, Japan

[21] Appl. No.: 09/019,535

[22] Filed: Feb. 5, 1998

Related U.S. Application Data

[62] Division of application No. 08/581,507, filed as application No. PCT/JP94/01208, Jul. 22, 1994, Pat. No. 5,756,763.

[30] Foreign Application Priority Data

Jul. 23, 1993 [JP] Japan ................... 5-182930

[51] Int. Cl.$^6$ ............... A61K 31/535; C07D 413/12; C07D 405/14
[52] U.S. Cl. ................... 514/232.2; 514/233.5; 514/343; 544/82; 544/131; 544/141; 546/256; 546/279.1
[58] Field of Search .................. 546/292, 290, 546/156; 544/126; 514/232.2, 233.5, 343

[56] References Cited

FOREIGN PATENT DOCUMENTS

| 0 468 339 | 1/1992 | European Pat. Off. . |
| 1-197468 | 8/1989 | Japan . |
| 2-28149 | 1/1990 | Japan . |
| 5-271187 | 10/1993 | Japan . |

*Primary Examiner*—Robert W. Ramsuer
*Assistant Examiner*—Ebenezer Sackey
*Attorney, Agent, or Firm*—Nields, Lemack & Dingman

[57] ABSTRACT

The invention relates to novel pyrrolidine derivatives represented by formula (1):

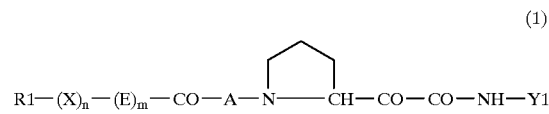

wherein:

R1 represents (1) a lower alkyl group having 1 to 6 carbon atoms, or (2) a 3- to 15-membered mono- or fused cyclic hydrocarbon group which may contain a hetero atom on the ring, or which may be substituted with a substituent(s); each of n and m represents an integer and the sum of n and m is an integer of 0 to 2; each of X and E represents oxygen, NR' (wherein R' is hydrogen or a lower alkyl group having 1 to 6 carbon atoms), sulfur, phenylene, CH=CH or $CH_2$; A represents an amino acid residue or an imino acid residue, which functional group may be optionally protected, or a glycine residue which may be substituted at the amino moiety thereof; and, Y1 represents a cycloalkyl group having 3 to 8 carbon atoms; or a salt thereof. The pyrrolidine derivatives inhibit a prolyl endopeptidase and are expected to be effective for the treatment of amnesia.

16 Claims, No Drawings

PYRROLIDINE DERIVATIVES

This Application is a Divisional of application Ser. No. 08/581,507 filed Jan. 11, 1996 now U.S. Pat. No. 5,756,763 also a PCT JP94/01208 filed Jul. 22, 1994.

TECHNICAL FIELD

The present invention relates to a novel pyrrolidine derivative having an inhibitory action on a serine protease or a thiol protease, especially on prolyl endopeptidase, which is expected to be effective for the treatment of amnesia (Alzheimer disease) and autoimmune diseases, or a pharmaceutically acceptable salt thereof.

BACKGROUND ART

Low molecular protease inhibitors originating from natural sources such as leupeptin, chymostatin and elastatinal are known. Based on these compounds, a number of peptidyl aldehydes have been synthesized and provided as inhibitors. It is known that upon inhibition of serine protease or thiol protease, these peptidyl aldehydes are known to form a covalent bond to the hydroxy or thiol group of the enzyme, see Thompson, R. C., Biochemistry, 12, 47–51 (1973).

Peptidyl aldehydes contain an aldehyde group at the C terminus of peptide chain. Then, modification of their amino acid sequences to enhance the specificity or inhibitory activity is restricted to the N-terminal site. Compounds including Poststatin, that were found by the present inventors, contain also at the C terminus as the activity center such a structure that enhances the specificity and contain an α-keto acid moiety in peptide chain; it is thus considered that these compounds would inhibit the enzyme in the same mechanism as in the peptidyl aldehydes, cf. EP-A-0423358, EP-A-0468339 and U.S. Pat. No. 5,221,752. However, poststatin and the like might be degraded by various proteases in vivo since they have the peptide residue and amino acid residue bound to the a-keto acid structure at the C and N termini. It is therefore expected to develop compounds having other stable functional groups with less possibility of degradation.

DISCLOSURE OF INVENTION

The present inventors have made extensive studies to solve the foregoing problems. As a result, it has been found that novel pyrrolidine derivatives inhibit a serine protease or a thiol protease, especially prolyl endopeptidase and are expected to be an effective ingredient of drugs for the treatment of amnesia and autoimmune disease.

That is, a first aspect of the present invention relates to a novel pyrrolidine derivative represented by formula (Z) below, preferably formulae (1) through (4) below.

A pyrrolidine derivative represented by formula (Z):

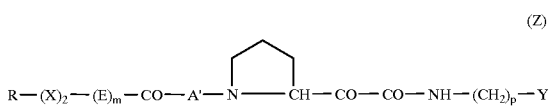

(Z)

wherein R represents R1, R2 or R3;

R1 represents (1) a lower alkyl group having 1 to 6 carbon atoms, or (2) a 3- to 15-membered mono- or fused cyclic hydrocarbon group which may contain a hetero atom on the ring, or which may be substituted with a substituent(s);

R2 represents a 3- to 15-membered mono- or fused cyclic hydrocarbon group which may contain a hetero atom on the ring, or which may be substituted with a substituent(s);

R3 represents a phenyl group which may be substituted;

each of n and m represents an integer and the sum of n and m is an integer of 0 to 2;

each of X and E represents oxygen, NR' (wherein R' is hydrogen or a lower alkyl group having 1 to 6 carbon atoms), sulfur, phenylene, CH=CH or $CH_2$;

A' represents a single bond or A; A represents an amino acid residue or an imino acid residue which functional group may be optionally protected, or a glycine residue which may be substituted at the amino moiety thereof;

p represents an integer of 0 to 3; and,

Y represents Y1 and Y2; Y1 represents a cycloalkyl group having 3 to 8 carbon atoms and Y2 represents a 3- to 15-membered mono- or fused cyclic hydrocarbon group which may contain a hetero atom on the ring, or which may be substituted with a substituent(s);

provided that:

when A' represents A, R is R1, p is 0 and Y is Y1;

when A' represents a single bond and p represents 0, R is R2 and Y is Y1 (except that (1) R2 is a phenyl group which may be substituted and both X and E are $CH_2$, (2) n+m is 0; R2 is a cycloalkyl group which may be substituted or a phenyl group which may be substituted and (3) R2 is a phenyl group which may be substituted, X is $CH_2$, E is O and both n and m are 1); and, when A' represents a single bond and p represents an integer of 1 to 3, R is R2 or R3 and Y is Y2; or a salt thereof;

a pyrrolidine derivative represented by formula (1):

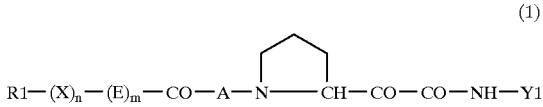

(1)

wherein:

R1 represents (1) a lower alkyl group having 1 to 6 carbon atoms, or (2) a 3- to 15-membered mono- or fused cyclic hydrocarbon group which may contain a hetero atom on the ring, or which may be substituted with a substituent(s);

each of n and m represents an integer and the sum of n and m is an integer of 0 to 2;

each of X and E represents oxygen, NR' (wherein R' is hydrogen or a lower alkyl group having 1 to 6 carbon atoms), sulfur, phenylene, CH=CH or $CH_2$;

A represents an amino acid residue or an imino acid residue, which functional group may be optionally protected, or a glycine residue which may be substituted at the amino moiety thereof; and, Y1 represents a cycloalkyl group having 3 to 8 carbon atoms;

or salts thereof;

a pyrrolidine derivative represented by formula (2):

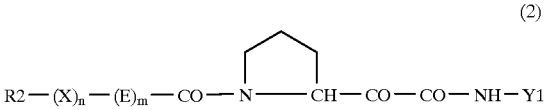

(2)

wherein:

R2 represents a 3- to 15-membered mono- or fused cyclic hydrocarbon group which may contain a hetero atom on the ring, or which may be substituted with a substituent(s);

each of n and m represents an integer and the sum of n and m is an integer of 0 to 2;

each of X and E represents oxygen, NR' (wherein R' is hydrogen or a lower alkyl group having 1 to 6 carbon atoms), sulfur, phenylene, CH=CH or $CH_2$; and, Y1 represents a cycloalkyl group having 3 to 8 carbon atoms, except that (1) R2 is a phenyl group which may be substituted and both X and E are CH$_2$, (2) n+m is 0; R2 is a cycloalkyl group which may be substituted or a phenyl group which may be substituted and (3) R2 is a phenyl group which may be substituted, X is CH$_2$, E is 0 and both n and m are 1);
or a salt thereof;
a pyrrolidine derivative represented by formula (3):

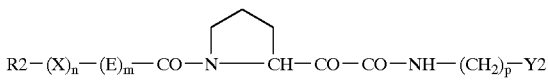

(3)

wherein:
R2 represents a 3- to 15-membered mono- or fused cyclic hydrocarbon group which may contain a hetero atom on the ring, or which may be substituted with a substituent(s);
each of n and m represents an integer and the sum of n and m is an integer of 0 to 2;
each of X and E represents oxygen, NR' (wherein R' is hydrogen or a lower alkyl group having 1 to 6 carbon atoms), sulfur, phenylene, CH=CH or CH$_2$;
p represents an integer of 1 to 3; and,
Y2 represents a 3- to 15-membered mono- or fused cyclic hydrocarbon group which may contain a hetero atom on the ring, or which may be substituted with a substituent(s);
or a salt thereof; and,
a pyrrolidine derivative represented by formula (4):

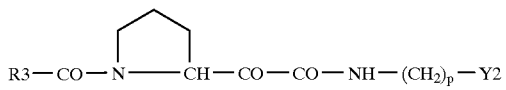

(4)

wherein
R3 represents a phenyl group which may be substituted;
p represents an integer of 1 to 3; and,
Y2 represents a 3- to 15-membered mono- or fused cyclic hydrocarbon group which may contain a hetero atom on the ring, or which may be substituted with a substituent(s);
or a salt thereof.

A second aspect of the present invention relates to a pharmaceutical composition comprising as an effective ingredient the pyrrolidine derivative represented by formula (Z) or any one of formulae (1) through (4), or a salt thereof.

A third aspect of the present invention relates to use of the pyrrolidine derivative represented by formula (Z) or represented by any one of formulae (1) through (4) or a salt thereof, as an effective ingredient for a pharmaceutical composition.

A fourth aspect of the present invention relates to use of the pyrrolidine derivative represented by formula (Z) or represented by any one of formulae (1) through (4) or a salt thereof, for the preparation of a pharmaceutical composition for inhibiting the activity of a serine protease or thiol protease.

A fifth aspect of the present invention relates to a method for inhibiting the activity of a serine protease or thiol protease which comprises administering an effective dose of the pyrrolidine derivative represented by formula (Z) or represented by any one of formulae (1) through (4) or a salt thereof to a mammal including human.

BEST MODE FOR CARRYING OUT THE INVENTION

In the present invention, the pyrrolidine derivatives of formula (Z) or salts thereof are preferably those shown by formulae (1) through (4) or salts thereof. Accordingly, the present invention will be described below, with reference to the pyrrolidine derivatives of formulae (1) to (4) or salts thereof.

In formula (1), R1 represents (1) a lower alkyl group having 1 to 6 carbon atoms, or (2) a 3- to 15-membered mono- or fused cyclic hydrocarbon group which may contain a hetero atom on the ring, or which may be substituted with a substituent(s).

The lower alkyl group means an alkyl group having 1 to 6 carbon atoms and specific examples include methyl, ethyl, propyl, isopropyl, butyl, 2-methylpropyl, t-butyl, pentyl and hexyl. Preferred is a branched alkyl group such as methyl, isopropyl, 2-methylpropyl and t-butyl, more preferably methyl and t-butyl.

The hetero atom on the ring means an oxygen, nitrogen and sulfur atom and examples of the substituent on the ring are a lower alkyl group, a lower alkoxy group (e.g., methoxy, ethoxy, propoxy, isopropoxy, butoxy, t-butoxy, pentyloxy and hexyloxy), phenoxy, methylenedioxy, a halogen atom, hydroxy, mercapto, an alkylthio group, nitro and a mono- and di-lower alkylamino group (e.g., methylamino, dimethylamino, ethylamino, diethylamino, propylamino, dipropylamino, isopropylamino, diisopropylamino, butylamino and dibutylamino).

The cyclic hydrocarbon group means a monovalent group derived from a saturated or unsaturated cyclic compound, e.g., furan, thiophene, pyrrole, 2H-pyrrole, oxazole, isoxazole, thiazole, isothiazole, imidazole, pyrazole, triazole, tetrazole, furazane, pyran, pyridine, pyridazine, pyrimidine, pyrazine, 2-pyrroline, pyrrolidine, 2-imidazoline, imidazolidine, 2-pyrazoline, pyrazolidine, piperidine, piperazine, morpholine, indole, isoindole, benzo [b]furan, benzo[b]thiophene, indolidine, 4H-chromene, quinoline, isoquinoline, 4H-quinolidine, purine, 1H-indazole, quinazoline, cinnoline, quinoxaline, phthalazine, pteridine, carbazole, acridine, phenanthridine, xanthene, phenazine, phenothiazine, phenoxthine, phenoxazine, thianthrene, indoline, isoindoline, chroman, isochroman, cyclohexane, cyclohexene, cyclopentane, cyclopentene, cyclopropane, cyclobutane, benzene, indene, naphthalene, azulene, fluorene, phenanthrene, anthracene, acenaphthylene and biphenylene. Of these groups, preferred are a phenyl group, a cycloalkyl group having 3 to 8 carbon atoms, a pyridyl, morpholinyl, piperidinyl, pyrrolidinyl, imidazolyl, naphthyl, quinolyl, isoquinolyl, thienyl or furyl group, which may be substituted.

In formula (1) above, preferred examples of the group shown by R1—(X)n—(E)m—CO— include acetyl, t-butoxycarbonyl, benzoyl, benzyloxycarbonyl, phenoxyacetyl, cyclohexylcarbonyl, cyclohexylacetyl, cyclohexylpropionyl, phenylthioacetyl, pyridylthioacetyl, pyridylacetyl, morpholinomethylbenzoyl, piperidinomethylbenzoyl, pyrrolidinomethylbenzoyl, phenoxybenzoyl, naphthoyl, quinolinecarbonyl, isoquinolinecarbonyl, thenoyl, furancarbonyl, furylacryloyl, pyridylacryloyl, pyridylcarbonyl and cinnamoyl.

In formula (1) above, examples of the amino acid residue shown by A include residues of phenylalanine, homophenylalanine, valine, leucine, isoleucine, alanine, β-cyclohexyla.lanine; an optionally protected amino acid such as a lysine (e.g., lysine, ε-carbobenzoxylidine and ε-t-butoxycarbonyllysine), an ornithine (e.g., ornithine, δ-carbobenzoxyorinithine and δ-t-butoxycarbonylornithine), an arginine (e.g., arginine and nitroarginine), a serine (e.g., serine, O-benzylserine and O-t-butylserine), a homoserine (e.g., homoserine, O-benzylhomoserine and O-t-butyl-homoserine), a threonine (e.g., threonine, O-benzylthreonine and O-t-butylthreonine), a methionine (e.g., methionine and methionine sulfoxide), an aspartic acid (e.g., aspartic acid, 4-benzyl aspartate and 4-t-butyl aspartate), and a glutamic acid (e.g., glutamic acid, 5-benzyl glutamate and 5-t-butyl glutamate). Examples of the imino acid residue are those of proline, a hydroxyproline (e.g., hydroxyproline, O-benzylhydroxyproline and O-t-butylhydroxyproline), and dihydroindole-2-carbonyl. Examples of the glycine residue which may be substituted on the amino group thereof include glycine, sarcosine, N-benzylglycine, N-cyclohexylglycine, N-cyclohexylmethylglycine, N-isopropylglycine and N-isobutylglycine. Among them, preferred are phenylalanine, homophenylalanine, valine, leucine, isoleucine, β-cyclohexylalanine, N-benzylglycine, proline and dihydroindole-2-carbonyl, more preferably phenylalanine, valine, N-benzylglycine, proline, β-cyclohexylalanine and dihydroindole-2-carbonyl. Any mammalian enzyme that acts to cleave the bond Phe-Pro is unknown and thus, phenylalanine is most preferred. The functional groups of these amino acids on their side chains may be protected, if necessary and desired, and the steric configuration may also be any of D, L and DL but L-configuration is generally preferred.

The cycloalkyl group shown by Y1 refers to a cycloalkyl group having 3 to 10 carbon atoms, preferably 3 to 8 carbon atoms, and preferred examples include cyclopropyl, cyclobutyl, cyclopentyl, cyclohexyl, cycloheptyl and cyclooctyl.

In formula (1), preferred pyrrolidine derivatives of the present invention are compounds wherein R1—(X)n—(E)m—CO— represents acetyl, t-butoxycarbonyl, benzoyl, benzyloxycarbonyl, phenoxyacetyl, cyclohexylcarbonyl, cyclohexylacetyl, cyclohexylpropionyl, phenylthioacetyl, pyridylthioacetyl, pyridylacetyl, morpholinomethylbenzoyl, piperidinomethylbenzoyl, pyrrolidinomethylbenzoyl, phenoxybenzoyl, naphthoyl, quinolinecarbonyl, isoquinolinecarbonyl, thenoyl, furancarbonyl, furylacryloyl, pyridylacryloyl, pyridylcarbonyl or cinnamoyl; A represents a residue of phenylalanine, homophenylalanine, valine, leucine, isoleucine, alanine, β-cyclohexylalanine; a lysine, ornithine, arginine, serine, homoserine, threonine, methionine, aspartic acid, glutamic acid, proline, hydroxyproline, glycine, sarcosine, N-benzylglycine, N-cyclohexylglycine, N-cyclohexylmethylglycine, N-isopropylglycine, N-isobutylglycine or dihydroindole-2-carbonyl; and Y1 is a cycloalkyl group having 3 to 8 carbon atoms.

More preferred compounds are those of formula (1) wherein R1—(X)n—(E)m—CO— represents acetyl, t-butoxycarbonyl, benzoyl, benzyloxycarbonyl, phenoxyacetyl, cyclohexylpropionyl, phenylthioacetyl, pyridylthioacetyl, pyridylacetyl, morpholinomethylbenzoyl, phenoxybenzoyl, naphthoyl, quinolinecarbonyl, isoquinolinecarbonyl, thenoyl, furylacryloyl, pyridylacryloyl, pyridylcarbonyl or cinnamoyl; A represents a residue of phenylalanine, homophenylalanine, valine, leucine, isoleucine, N-benzylglycine, proline, β-cyclohexylalanine or dihydroindole-2-carbonyl; and Y1 is a cycloalkyl group having 3 to 8 carbon atoms.

Among the preferred compounds described above, most preferred compounds are those of formula (1) wherein A represents a residue of phenylalanine, valine, N-benzylglycine, proline, β-cyclohexylalanine or dihydroindole-2-carbonyl.

In formula (2) above, R2 represents a phenyl group which may be substituted with a substituent(s), a cycloalkyl group having 3 to 8 carbon atoms, pyridyl, morpholinyl, piperidinyl, pyrrolidinyl, imidazolyl, naphthyl, quinolyl, isoquinolyl, thienyl or furyl. Examples of the phenyl group which may be substituted with a substituent(s) are the same as those given for formula (1) above.

In formula (2) above, preferred examples of the group shown by R2—(X)n—(E)m—CO— include phenoxyacetyl, phenylthioacetyl, pyridylthioacetyl, pyridylacetyl, morpholinomethylbenzoyl, piperidinomethylbenzoyl, pyrrolidinomethylbenzoyl, phenoxybenzoyl, imidazolylmethylbenzoyl, naphthoyl, pyridinecarbonyl, quinolinecarbonyl, isoquinolinecarbonyl, thenoyl, furancarbonyl, furylacryloyl, pyridylacryloyl, cinnamoyl and a substituted cinnamoyl group.

More preferred examples of the group shown by R2—(X)n—(E)m—CO— are morpholinomethylbenzoyl, piperidinomethylbenzoyl, phenoxybenzoyl, imidazolylmethylbenzoyl, naphthoyl, pyridinecarbonyl, quinolinecarbonyl, pyridylacryloyl, cinnamoyl and chlorocinnamoyl.

In the pyrrolidine derivatives of formula (2) of the present invention, examples of the cyclic hydrocarbon group which may contain a hetero atom on the ring, or which may be substituted with a substituent(s) are the same as those given above for formula (1).

Y1 represents a cycloalkyl group having 3 to 8 carbon atoms and examples of the cycloalkyl group are the same as given above for formula (1).

In the present invention, R2 in formula (3) refers to the same as given for formula (2) above.

Among the compounds of formula (3), the compounds wherein R2 is R3, i.e., a phenyl group which may be substituted and the sum of n and m is 0, will be described hereinafter as the compounds of formula (4).

In formula (3) above, preferred examples of the group shown by R2—(X)n—(E)m—CO— include phenoxyacetyl, phenylthioacetyl, pyridylthioacetyl, pyridylacetyl, morpholinomethylbenzoyl, piperidinomethylbenzoyl, pyrrolidinomethylbenzoyl, phenoxybenzoyl, naphthoyl, quinolinecarbonyl, isoquinolinecarbonyl, thenoyl, furancarbonyl, furylacryloyl and cinnamoyl.

Examples of the substituent on the ring shown by Y2 include a lower alkyl group, a lower alkoxy group (e.g., methoxy, ethoxy, propoxy, isopropoxy, butoxy, t-butoxy, pentyloxy and hexyloxy), phenoxy, methylenedioxy, a halogen atom, hydroxy, mercapto, an alkylthio group, nitro and a mono- and di-lower alkylamino group (e.g., methylamino, dimethylamino, ethylamino, diethylamino, propylamino, dipropylamino, isopropylamino, diisopropylamino, butylamino and dibutylamino).

The hetero atom contained in the group shown by Y2 means an oxygen, nitrogen or sulfur atom and is four or less. Examples of such a hetero atom-containing cyclic hydrocarbon group shown by Y2 include a monovalent group derived from pyridine, pyrimidine, pyridazine, purine, imidazole, benzimidazole, morpholine, piperazine, pyrrolidine, piperidine, furan, thiophene, pyran, thiazole and benzothiazole. Of these groups, preferred examples are a monovalent group of nitrogen-containing heterocyclic group derived from pyridine, morpholine, benzimidazole, piperazine and pyrrolidine.

In formula (3), preferred compounds are those wherein R2—(X)n—(E)m—CO— represents phenoxyacetyl, phenylthioacetyl, pyridylthioacetyl, pyridylacetyl, morpholinomethylbenzoyl, piperidinomethylbenzoyl, pyrrolidinomethylbenzoyl, phenoxybenzoyl, naphthoyl, quinolinecarbonyl, isoquinolinecarbonyl, pyridylcarbonyl, thenoyl, furancarbonyl, furylacryloyl, pyridylacryloyl or cinnamoyl; and Y2 is a monovalent group derived from pyridine, morpholine, benzimidazole, piperidine or pyrrolidine.

More preferred are compounds of formula (3) wherein R2—(X)n—(E)m—CO— represents pyridylthioacetyl or pyridylcarbonyl; p is an integer of 1 or 2; and Y2 is a monovalent group from pyridine, morpholine or benzimidazole.

In the present invention, R3 in formula (4) represents (1) a phenyl group which may be substituted. Examples of the substituent on the ring are a lower alkyl group, a lower alkoxy group (e.g., methoxy, ethoxy, propoxy, isopropoxy, butoxy, t-butoxy, pentyloxy and hexyloxy), phenoxy, methylenedioxy, a halogen atom, hydroxy, mercapto, an alkylthio group, nitro and a mono- and di-lower alkylamino group (e.g., methylamino, dimethylamino, ethylamino, diethylamino, propylamino, dipropylamino, isopropylamino, diisopropylamino, butylamino and dibutylamino).

Y2 is the same as that given for formula (3).

In the compounds of formula (4), preferred are those wherein R3 represents a benzoyl group which may be substituted; and Y2 represents a monovalent group of pyridine, morpholine, benzimidazole, piperidine or pyrrolidine. Among them, chlorobenzoyl is more preferred as R3.

The pyrrolidine derivatives represented by formulae (1) through (4) may be in the form of pharmaceutically acceptable salts thereof. Examples of such salts are acid addition salts to inorganic acids such as hydrochloric acid, sulfuric acid and nitric acid;

and organic acids such as p-toluenesulfonic acid, citric acid, succinic acid, acetic acid, fumaric acid and maleic acid.

Representative examples of the pyrrolidine derivatives represented by formulae (1) to (4) are given in the following table.

Compounds of formula (1):

| R1 | n | m | X | E | A | Y1 |
|---|---|---|---|---|---|---|
| Ph | 0 | 0 | | | Phe | cHx |
| Ph | 0 | 0 | | | Phe | cPn |
| Ph | 1 | 1 | O | CH$_2$ | Phe | cHx |
| Ph | 1 | 1 | O | CH$_2$ | Phe | cPn |
| Ph | 1 | 1 | O | CH$_2$ | Val | cHx |
| Ph | 1 | 1 | O | CH$_2$ | Val | cPn |
| Ph | 0 | 0 | | | Phe | cHx |
| Ph(4-NO$_2$) | | | | | | |
| Ph | 0 | 0 | | | Phe | cPn |
| Ph(4-NO$_2$) | | | | | | |
| Ph | 1 | 1 | O | Ph(1.3) | Val | cHx |
| Ph | 1 | 1 | O | Ph(1.3) | Val | cPn |
| Ph(4-Cl) | 0 | 0 | | | Phe | cHx |
| Ph(i-Cl) | 0 | 0 | | | Phe | cPn |
| Ph(4-Br) | 0 | 0 | | | Phe | cHp |
| Ph | 1 | 1 | CH$_2$ | O | Val | cHx |
| Ph | 0 | 0 | | | Phe | cHx |
| (4-NH$_2$) | | | | | | |
| Ph | 0 | 0 | | | Phe | cPn |
| (4-NH$_2$) | | | | | | |
| Ph | 1 | 1 | S | CH$_2$ | Phe | cHx |
| Ph(4-Me) | 0 | 0 | | | Phe | cRx |
| Ph(4-Me) | 0 | 0 | | | Phe | cPn |
| Ph | 1 | 1 | CH$_2$ | O | Phe | cHx |
| Ph(4-MeO) | 0 | 0 | | | Phe | cHx |
| Ph(4-MeO) | 0 | 0 | | | Phe | cPn |
| Ph | 1 | 1 | O | Ph(1.3) | Phe | cPn |
| Ph | 1 | 1 | O | Ph(1.3) | Phe | cHp |
| Ph(4-OH) | 0 | 0 | | | Phe | cHx |
| Ph(4-OH) | 0 | 0 | | | Phe | cPn |
| Ph(2-Me) | 0 | 0 | | | Phe | cHx |
| Ph(3-Me) | 0 | 0 | | | Phe | cPn |
| Ph | 1 | 1 | O | Ph(1.3) | Phe | cHx |
| Ph | 1 | 1 | O | Ph(1.3) | Phe | cPr |
| Ph | 1 | 1 | O | Ph(1.3) | Phe | cOc |
| Ph (2.6-diMe) | 0 | 0 | | | Phe | cHx |
| Ph (2.6-diMe) | 0 | 0 | | | Phe | cPn |
| 4-pyridyl | 1 | 1 | S | CH$_2$ | Pro | cHx |
| 4-pyridyl | 1 | 1 | S | CH$_2$ | Pro | cPn |
| 4-pyridyl | 1 | 1 | S | CH$_2$ | Pro | cPn |
| Ph (3.5-diMe) | 0 | 0 | | | Phe | cHx |
| Ph (3.5-diMe) | 0 | 0 | | | Phe | cPn |
| t-butyl | 1 | 0 | O | | Phe | cHx |
| t-butyl | 1 | 0 | O | | Phe | cPn |
| t-butyl | 1 | 0 | O | | Plc | cHx |
| t-butyl | 1 | 0 | O | | Plc | cPr |
| isopropyl | 1 | 0 | O | | Phe | cHx |
| Me | 0 | 0 | | | Phe | cHx |
| Me | 0 | 0 | | | Cha | cPr |
| 1-naphthyl | 0 | 0 | | | Phe | cHx |
| 2-naphthyl | 0 | 0 | | | Phe | cHx |
| 2-naphthyl | 0 | 0 | | | Phe | cPn |
| 2-pyridyl | 0 | 1 | | CH$_2$ | Phe | cHx |
| 2-pyridyl | 0 | 1 | | CH$_2$ | Phe | cPn |
| 3-quinolyl | 0 | 0 | | | Phe | cHx |
| 2-quinolyl | 0 | 0 | | | Val | cHx |
| 2-quinolyl | 0 | 0 | | | Cha | cHx |
| 2-quinolyl | 0 | 0 | | | Cha | cPn |
| 2-quinolyl | 0 | 0 | | | Cha | cOc |
| 2-quinolyl | 0 | 0 | | | Phe | cPn |
| 2-pyridyl | 0 | 0 | | | Phe | cHp |
| 2-pyridyl | 0 | 0 | | | Phe | cHx |
| 2-pyridyl | 0 | 0 | | | Phe | cPn |
| 3-pyridyl | 0 | 0 | | | Phe | cHx |
| 3-pyridyl | 0 | 0 | | | Phe | cPn |
| 3-pyridyl | 1 | 0 | CH=CH | | Phe | cHx |
| 2-furyl | 1 | 0 | CH=CH | | Phe | cHx |
| 2-furyl | 1 | 0 | CH=CH | | Phe | cPn |
| 2-furyl | 1 | 1 | CH$_2$ | O | Phe | cHx |
| Ph(4-Cl) | 1 | 0 | CH=CH | | Phe | cHx |
| 2-thiophenyl | 0 | 0 | | | Phe | cHx |
| 2-thiophenyl | 0 | 0 | | | Phe | cPn |
| cHx | 1 | 1 | CH$_2$ | CH$_2$ | Phe | cHx |
| cHx | 1 | 1 | CH$_2$ | CH$_2$ | Phe | cPn |
| cPn | 1 | 1 | CH$_2$ | CH$_2$ | Phe | cHx |
| 4-pyridyl | 0 | 0 | | | Phe | cHp |
| 4-pyridyl | 0 | 0 | | | Phe | cHx |
| 4-pyridyl | 0 | 0 | | | Phe | cPn |
| 4-pyridyl | 1 | 1 | S | CH$_2$ | Phe | cHx |
| 4-pyridyl | 1 | 1 | S | CH$_2$ | Phe | cPn |
| morphorino | 1 | 1 | CH$_2$ | Ph(1.4) | Phe | cHx |
| morphorino | 1 | 1 | CH$_2$ | Ph(1.4) | Phe | cPn |
| 4-pyridyl | 0 | 0 | | | BnGly | cHx |
| 4-pyridyl | 1 | 1 | S | CH$_2$ | BnGly | cHx |
| Ph | 1 | 1 | CH$_2$ | N(CH$_3$) | Phe | cHx |
| Ph | 1 | 1 | CH$_2$ | N(CH$_3$) | Pro | cHx |
| thiophene | 0 | 0 | | | Phe | cHx |
| thiophene | 0 | 0 | | | Pro | cHx |

In the table, additional abbreviations are used to mean:
cHx: cyclohexyl
cPn: cyclopentyl
cPr: cyclopropyl
cOc: cyclooctyl
cHp: cycloheptyl
Ph: phenyl
Ph(a-B): phenyl group having substituent B at a-position, e.g., Ph(4-Cl): 4-chlorophenyl Ph(2,6-diMe): 2,6-dimethylphenyl -continued

| R1 | n | m | X | E | A | Y1 |
|---|---|---|---|---|---|---|

Me: methyl
MeO: methoxy
Ph(1,3): 1,3-phenylene
Ph(1,4): 1,4-phenylene
BnGly: N-benzylglycine
Phe: phenylalanine
Val: valine
Pro: proline
Cha: β-cyclohexylalanine
DIC: dihydoxyindole-2-carbonyl Compounds of formula (2):

| R2 | n | m | X | E | Y1 |
|---|---|---|---|---|---|
| Ph | 1 | 1 | O | Ph(1.3) | cHx |
| Ph | 1 | 1 | O | Ph(1.3) | cPn |
| Ph | 1 | 1 | O | $CH_2$ | cHx |
| Ph | 1 | 1 | O | $CH_2$ | cPn |
| Ph | 1 | 1 | S | $CH_2$ | cHx |
| Ph | 1 | 1 | S | $CH_2$ | cPn |
| 4-pyridyl | 1 | 1 | S | $CH_2$ | cHx |
| 4-pyridyl | 1 | 1 | S | $CH_2$ | cPn |
| 1-naphthyl | 0 | 0 | | | cHx |
| 2-naphthyl | 0 | 0 | | | cHx |
| 2-naphthyl | 0 | 0 | | | cPn |
| 2-naphthyl | 0 | 0 | | | cHp |
| 2-pyridyl | 0 | 1 | | $CH_2$ | cHx |
| 2-pyridyl | 0 | 1 | | $CH_2$ | cPn |
| 3-quinolyl | 0 | 0 | | | cHx |
| 2-quinolyl | 0 | 0 | | | cHx |
| 2-quinolyl | 0 | 0 | | | cPn |
| 2-pyridyl | 0 | 0 | | | cHp |
| 2-pyridyl | 0 | 0 | | | cHx |
| 2-pyridyl | 0 | 0 | | | cPn |
| 3-pyridyl | 0 | 0 | | | cHx |
| 3-pyridyl | 0 | 0 | | | cPn |
| 2-pyridyl | 1 | 0 | CH=CH | | cHx |
| 2-pyridyl | 1 | 0 | CH=CH | | cPn |
| 2-furyl | 1 | 0 | CH=CH | | cHx |
| 2-furyl | 1 | 0 | CH=CH | | cPn |
| 2-furyl | 1 | 0 | $CH_2$ | O | cHx |
| Ph | 1 | 0 | CH=CH | | cHx |
| Ph(4-Cl) | 1 | 0 | CH=CH | | cHx |
| 2-thiophenyl | 0 | 0 | | | cHx |
| 2-thiophenyl | 0 | 0 | | | cPn |
| 4-pyridyl | 0 | 0 | | | cHp |
| 4-pyridyl | 0 | 0 | | | cHx |
| 4-pyridyl | 0 | 0 | | | cPn |
| morphorino | 1 | 1 | $CH_2$ | Ph(1.4) | cHx |
| morphorino | 1 | 1 | $CH_2$ | Ph(1.4) | cPn |
| piperidino | 1 | 1 | $CH_2$ | Ph(1.4) | cHx |
| piperidino | 1 | 1 | $CH_2$ | Ph(1.4) | cPn |
| 1-imidazolyl | 1 | 1 | $CH_2$ | Ph(1.4) | cHx |
| 1-imidazolyl | 1 | 1 | $CH_2$ | Ph(1.4) | cPn |

Compounds of formula (3):

| R2 | n | m | X | E | p | Y2 |
|---|---|---|---|---|---|---|
| 4-pyridyl | 1 | 1 | S | $CH_2$ | 2 | morpholino |
| 2-pyridyl | 0 | 0 | | | 2 | morpholino |
| 3-pyridyl | 0 | 0 | | | 2 | morpholino |
| 4-pyridvl | 0 | 0 | | | 2 | morpholino |
| 4-pyridyl | 1 | 1 | S | $CH_2$ | 1 | 2-benzimidazolvl |
| 2-pyridyl | 0 | 0 | | | 1 | 2-benzimidazolyl |
| 3-pyridyl | 0 | 0 | | | 1 | 2-benzimidazolyl |
| 4-pyridyl | 0 | 0 | | | 1 | 2-benzimidazolyl |
| 4-pyridyl | 1 | 1 | S | $CH_2$ | 2 | 2-pyridyl |
| 2-pyridyl | 0 | 0 | | | 2 | 2-pyridyl |
| 3-pyridyl | 0 | 0 | | | 2 | 2-pyridyl |
| 4-pyridyl | 0 | 0 | | | 2 | 2-pyridyl |

Compounds of formula (4):

| R3 | p | Y2 |
|---|---|---|
| Ph(4-Cl) | 2 | morpholino |
| Ph(4-Cl) | 1 | 2-benzimidazolyl |
| Ph(4-Cl) | 2 | 2-pyridyl |

The compounds of the present invention represented by formulas (1) to (4) can be prepared by applying conventional methods used for synthesis of an acid amide or a peptide to a pyrrolidine derivative obtained from L-proline or DL-proline as a starting material to prepare an amide compound having a secondary hydroxy group, and then oxidizing the resulting acid amide compound by a conventional method for oxidizing a secondary hydroxy group to a ketone. Thus, the pyrrolidine derivatives of the present invention can be prepared, e.g., by the following reactions (A) through (G).

Reaction (A):

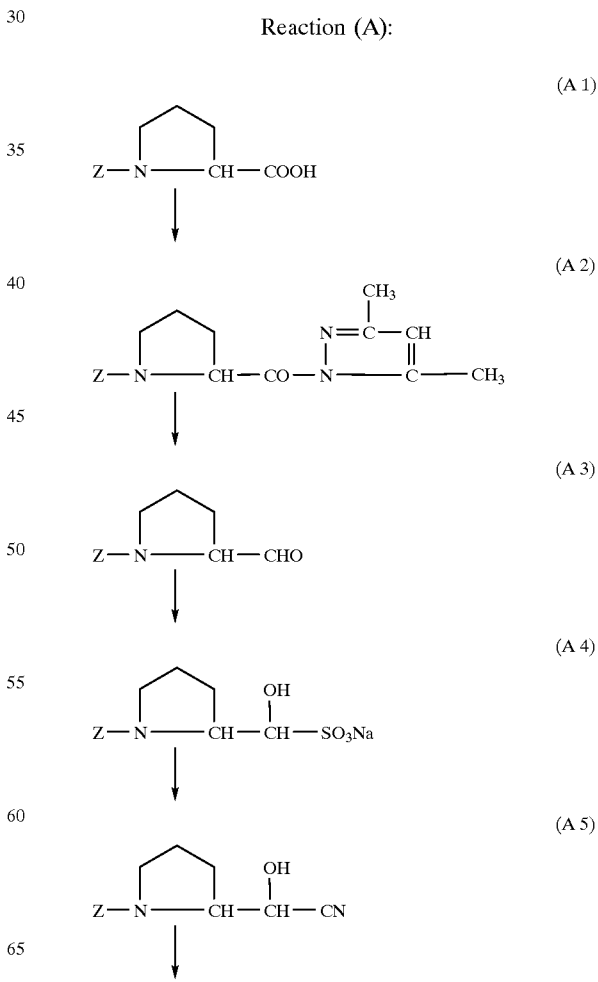

-continued

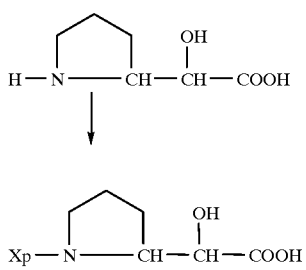
(A 6)

(A 7)

In Reaction (A), Z is benzyloxycarbonyl and Xp is an amino protective group. According to Reaction (A), 2-hydroxy-2-(N-t-butoxycarbonylpyrrolidin-2-yl)acetic acid, i.e., Compound (A7) wherein Xp is t-butoxycarbonyl is prepared from Z-proline (its steric configuration may be either L or DL, preferably L) by the method described in Rinzou Nishizawa, Tetsushi Saino, J. Med. Chem., 20, 513 (1977) or Japanese Patent Application Laid-Open No. 62-221667. With respect to the steric configuration of the 2-hydroxy group, a mixture of R- and S-form is obtained but the hydroxy group is later oxidized to the ketone. Accordingly, the mixture may be employed as it is or after separating into R- and S-forms. The separation may be effected in a conventional manner, e.g., by silica gel column chromatography (solvent system: dichloromethane/methanol).

Reaction (B):

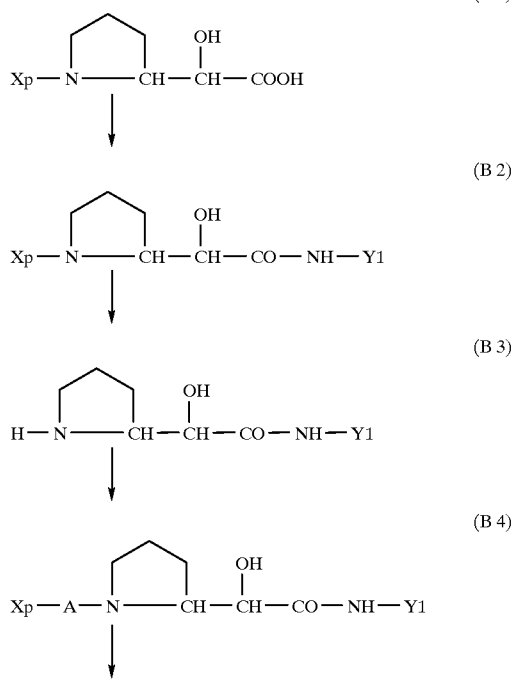

(B 1)

(B 2)

(B 3)

(B 4)

-continued

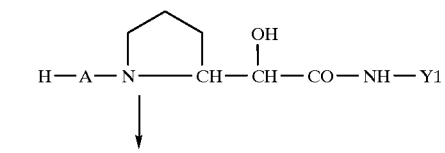
(B 5)

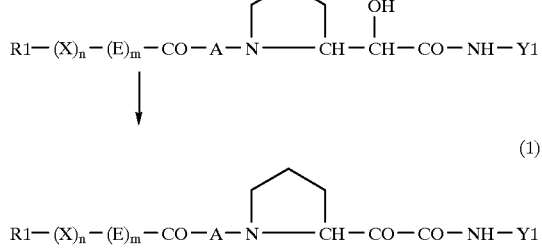
(B 6)

(1)

R1—(X)$_n$—(E)$_m$—CO—A—N——CH—CO—CO—NH—Y1

In Reaction (B) above, R1, X, E, n, m, A and Y1 have the same significance as defined hereinabove and Xp represents an amino protective group.

The process shown by Reaction (B) is explained below in more detail.

An α-hydroxyacetic acid derivative shown by formula (B1), which corresponds to Compound (A7) in Reaction (A), or an activated ester thereof is reacted with a compound shown by Y1—NH$_2$, wherein Y1 has the same significance as defined above, if necessary and desired, using dicyclo-carbodiimide or other carbodiimide and 1-hydroxy benzotriazole, or a peptide bond-forming reagent such as Bop reagent, PyBop reagent, etc. to obtain an amide of formula (B2).

Then the amino protective group Xp in formula (B2) is removed to give Compound (B3). The protective group Xp may be split off in a conventional manner; where the protective group is, for example, Boc, the protective group may be removed using a hydrochloric acid-dioxane solution or using trifluoroacetic acid as a splitting-off reagent; where the protective group is benzyloxycarbonyl, the group may be removed by catalytic hydrogenation in the presence of a Pd catalyst.

Next, Compound (B3) is reacted with a compound shown by Xp—A—OH, wherein Xp and A have the same significance as above, using a peptide bond-forming reagent as in the preparation of the amide (B2) to give an amide of formula (B4).

The amino protective group Xp is removed as in the preparation of Compound (B3) to give Compound (B5).

Compound (B5) is then reacted with a compound shown by:

R1—(X)n—(E)m—CO—OH

R1—(X)n—(E)m—CO—OSu or

R1—(X)n—(E)m—CO—Cl wherein R1, X, E, n and m have the same significance as defined above, to introduce R1—(X)n—(E)m—CO—. Compound of formula (B6) is thus obtained.

Compound (B6) is reacted with an appropriate oxidizing agent, e.g., a combination of dimethylsulfoxide (DMSO)/ pyridine, trifluoroacetic acid/a carbodiimide (dicyclohexylcarbodiimide, 1-ethyl-3-(3-dimethylaminopropyl)carbodiimide (EDC)) or DMSO/ acetic anhydride thereby to oxidize the hydroxy group of Compound (B6). Compound of formula (1) can be so obtained. The reaction is carried out generally in an inert organic solvent such as benzene, toluene or DMF or in DMSO at a temperature in the range of −10° C. to the boiling point of a solvent.

The compounds of the present invention may also be synthesized by the following Reaction (C), which is different from Reaction (B) described above.

Reaction (C):

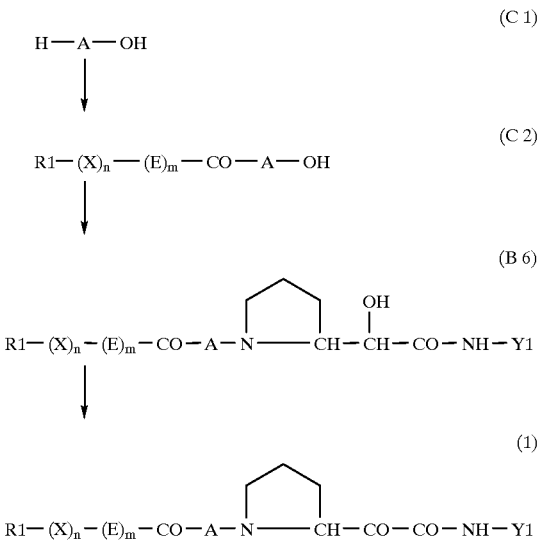

In Reaction (C) above, R1, X, E, n, m, A and Y1 have the same significance as defined above.

The procedures shown by Reaction (C) are explained below in more detail.

An amino acid shown by formula (C1) is reacted with an activated derivative of an acid shown by:

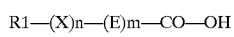

e.g., an acid chloride shown by R1—(X)n—(E)m—CO—Cl or an activated ester of R1—(X)n—(E)m—CO—OH and 1-hydroxybenzotriazole or N-hydroxysuccinimide to introduce the group shown by R1—(X)n—(E)m—CO—, whereby Compound (C2) is obtained. Compound (C2) is then reacted with Compound (B3) in Reaction (B) above using the same peptide bond-forming reagent as given for Reaction (B). Compound (B6) is thus obtained. Then, Compound (B6) is oxidized as in the oxidation performed to obtain the compound of formula (1) in Reaction (B). Thus, the compound of formula (1) can be prepared.

The compound of formula (2) can be prepared in a manner similar to the procedures for preparing the compound of formula (1).

Reaction (D):

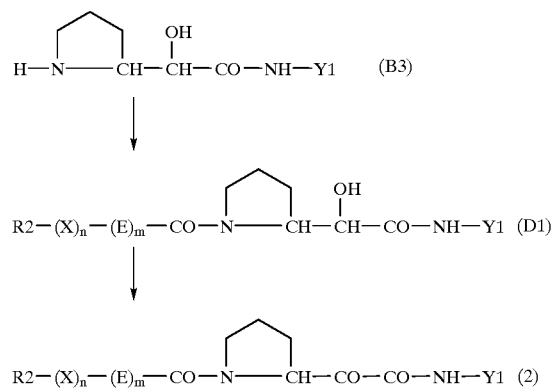

In Reaction (D) above, R2, X, E, n, m and Y1 have the same significance as defined above.

The procedures for Reaction (D) are explained below in more detail.

An amide derivative of α-hydroxyacetic acid shown by formula (B3) is reacted with a compound shown by:

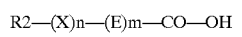

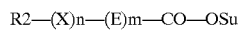

or

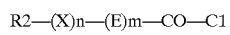

wherein R2, X, E, n and m have the same significance as defined above, to introduce R2—(X)n—(E)m—CO—. Compound of formula (D1) is thus obtained.

Compound (D1) is oxidized at the hydroxy group thereof in a manner similar to the procedure for preparing the compound of formula (1) in Reaction (B). The compound of formula (2) is thus obtained. The reaction is carried out generally in an inert organic solvent such as benzene, toluene or DMF at a temperature in the range of −10° C. to the boiling point of a solvent.

The compound of formula (2) may also be prepared according to Reaction (E).

Reaction (E):

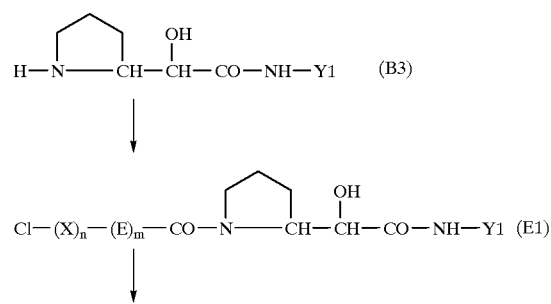

-continued

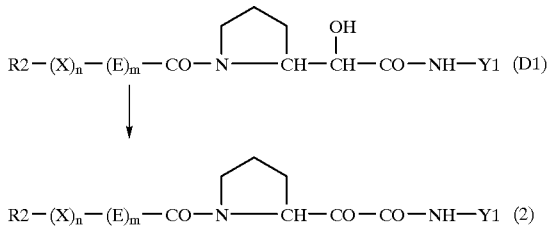

In Reaction (E) above, R2, X, E, n, m and Y1 have the same significance as defined above.

The procedures for Reaction (E) are explained below in more detail.

An amide shown by formula (B3) is reacted with an activated derivative of an acid shown by:

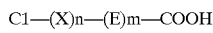

e.g., an acid chloride shown by Cl—(X)n—(E)m—COCl or a combination of Cl—(X)n—(E)m—COOH, carbodiimide and 1-hydroxybenzotriazole, or a peptide bond-forming reagent represented by Bop reagent to introduce Cl—(X)n—(E)m—CO— whereby the compound of formula (E1) is obtained. The compound of formula (E1) is reacted with a cyclic compound containing basic NH group, such as morpholine, piperidine or imidazole to give the compound of formula (D1). Then the compound of formula (D1) is oxidized following the procedure for preparing the compound of formula (2) in Reaction (B). The compound of formula (2) is thus prepared.

The compound of the present invention represented by formula (3) is prepared by the procedures of Reaction (F).

Reaction (F):

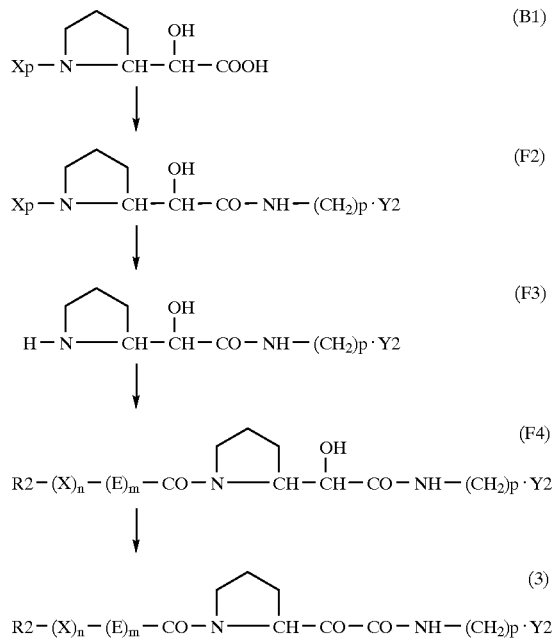

In Reaction (F) described above, R2, X, E, n, m, p and Y1 have the same significance as defined for formula (3) above; and Xp represents asn amino protective group.

The procedures for Reaction (F) are explained below in more detail.

An α-hydroxyacetic acid derivative shown by formula (B1), which corresponds to Compound (A7) in Reaction (A), or an activated ester thereof is reacted with a compound shown by:

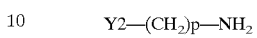

wherein Y2 has the same significance as defined above, if necessary and desired, using dicyclocarbodiimide or other carbodiimide and 1-hydroxy benzotriazole, or a peptide bond-forming reagent such as Bop reagent, PyBop reagent, etc. to obtain an amide of formula (F2).

Then the amino protective group Xp in formula (F2) is removed to give Compound (F3). The protective group Xp may be removed in a conventional manner; where the protective group is, for example, Boc, the protective group may be removed using a hydrochloric acid-dioxane solution or using trifluoroacetic acid as a splitting-off reagent; where the protective group is benzyloxycarbonyl, the protective group may be removed by catalytic hydrogenation in the presence of a Pd catalyst.

Next, Compound (F3) is reacted with a compound shown by:

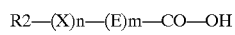

or

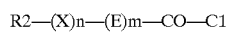

wherein R2, X, E, n and m have the same significance as defined above, to introduce R2—(X)n—(E)m—CO—. Compound of formula (F6) is thus obtained.

The compound of formula (F4) is oxidized following the procedure for preparing the compound of formula (2) in Reaction (B). The compound of formula (3) is thus prepared.

The compound of the present invention represented by formula (4) is prepared by the procedures of Reaction (G).

Reaction (G):

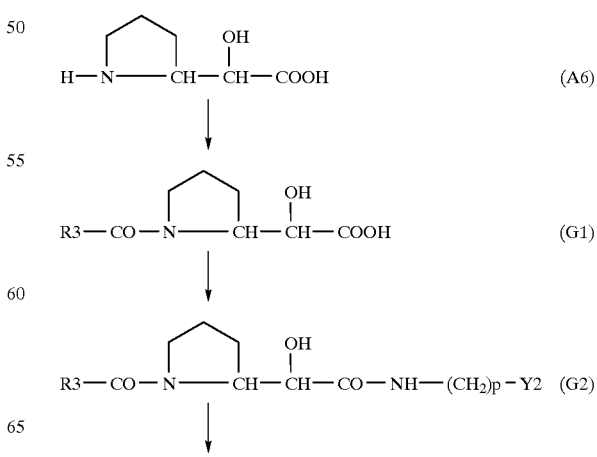

-continued

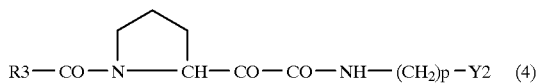 (4)

in Reaction (G) above, R3, p and Y2 have the same significance as defined for formula (4) hereinabove. The procedures shown by Reaction (G) are explained below in more detail.

An imino acid shown by formula (A6) is reacted with an activated derivative of an acid shown by R3—OH, e.g., an acid chloride shown by R3—COCl or an activated ester of R3—COOH and 1-hydroxybenzotriazole or N-hydroxysuccinimide to introduce the group shown by R3—CO—, whereby Compound (G1) is obtained. Compound (G1) or its activated ester is then reacted with a compound shown by:

Y2—(CH$_2$)p—NH$_2$ wherein Y2 has the same significance as defined above, if necessary and desired, using dicyclocarbodiimide or other carbodiimide and 1-hydroxy benzotriazole, or a peptide bond-forming reagent such as Bop reagent, PyBop reagent, etc. to obtain an amide of formula (G2).

Thereafter the compound of formula (G2) is oxidized as in the oxidation performed to obtain the compound of formula (1) in Reaction (B). Thus, the compound of formula (4) can be prepared.

The compound of formula (G2) can also be prepared by reacting the compound of formula (F3) with an acid shown by R3—OH using a peptide bond-forming reagent.

The compounds of the present invention may be prepared into a pharmaceutical composition in a conventional manner, using an excipient, a binder, a degrading agent, a lubricant, a stabilizer, a corrigent, etc., which are known in the art.

The pharmaceutical composition may be administered orally in the form of, e.g., a tablet, a capsule, a granule, a powder or syrup. The pharmaceutical composition of the present invention may also be administered parenterally in the form of an injection or a suppository.

A dose may vary depending upon condition and age but is generally in the range of 0.5 to 200 mg/kg body weight, preferably 1 to 100 mg/kg body weight.

The α-hydroxyacetic acid derivatives represented by formulae (B6), (D1), (F4) and (G2) below are useful as intermediates for preparing the compounds of formulae (1), (2), (3) and (4), all having a potent enzyme inhibition activity.

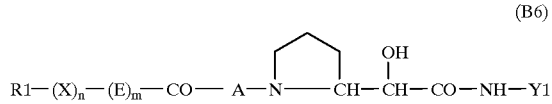 (B6)

In formula (B6), R1, n, m, X, E, A and Y1 have the same significance as defined for formula (1) above.

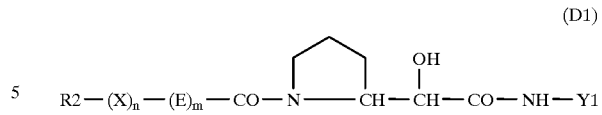 (D1)

In formula (D1), R2, n, m, X, E and Y1 have the same significance as defined for formula (2) above.

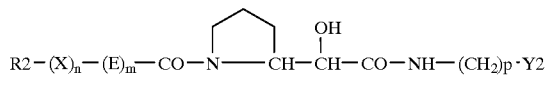 (F4)

In formula (F4), R2, n, m, X, E, p and Y2 have the same significance as defined for formula (3) above.

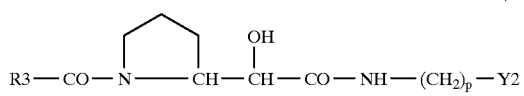 (G2)

In formula (G2), R3, p and Y2 have the same significance as defined for formula (4) above.

The compounds of formulae (B6), (D1), (F4) and (G2) are racemic or a mixture of two diastereomers; if necessary and desired, the diastereomer mixture may be divided into each diastereomer by a known method, e.g., using silica gel chromatography (solvent system: dichloromethane/methanol).

The compounds of the present invention were investigated in vitro and in vivo with respect to the prolyl endopeptidase inhibitory activity, which will be shown in the following experiments.

Experiment 1

Method for determination of the enzyme inhibitory action

Using 0.1 mM of benzyolxycarbonylglycyl-proline-β-naphthylamide as substrate and swine kidney-derived prolyl endopeptidase as enzyme, the enzyme was acted on the substrate at 37° C. for 30 minutes in 0.025 M Tris (hydroxymethyl)methane amine-hydrochloric acid (pH 7.5) solution. Fast Garnet was added to form a color and absorbance was measured at 525 nm. The inhibitory activity is expressed in terms of concentration required for 50% inhibition (IC$_{50}$).

The results are shown in Table 1 below.

TABLE 1

| Enzyme Inhibitory Activity | IC$_{50}$ (μg/ml) |
| --- | --- |
| Compound of Example 4 | 0.0005 |
| Compound of Example 7 | 0.0005 |
| Compound of Example 9 | 0.00064 |
| Compound of Example 13 | 0.00082 |
| Compound of Example 15 | 0.0015 |
| Compound of Example 18 | 0.0011 |
| Compound of Example 20 | 0.0008 |
| Compound of Example 22 | 0.0017 |
| Compound of Example 24 | 0.0011 |
| Compound of Example 26 | 0.00085 |
| Compound of Example 28 | 0.00065 |
| Compound of Example 31 | 0.0031 |
| Compound of Example 33 | 0.0005 |
| Compound of Example 41 | 0.0008 |

TABLE 1-continued

| Enzyme Inhibitory Activity | IC$_{50}$ ($\mu$g/ml) |
|---|---|
| Compound of Example 43 | 0.0009 |
| Compound of Example 45 | 0.0012 |
| Compound of Example 47 | 0.0008 |
| Compound of Example 49 | 0.0031 |
| Compound of Example 51 | 0.0014 |
| Compound of Example 53 | 0.002 |
| Compound of Example 55 | 0.0008 |
| Compound of Example 57 | 0.0054 |
| Compound of Example 60 | 0.0042 |
| Compound of Example 64 | 0.0082 |
| Compound of Example 66 | 0.01 |
| Compound of Example 68 | 0.017 |
| Compound of Example 70 | 0.043 |
| Compound of Example 72 | 0.085 |
| Compound of Example 74 | 0.032 |
| Compound of Example 76 | 0.0058 |
| Compound of Example 78 | 0.0092 |
| Compound of Example 84 | 0.031 |
| Compound of Example 86 | 0.035 |
| Compound of Example 88 | 0.054 |
| Compound of Example 93 | 0.055 |
| Compound of Example 95 | 0.066 |
| Compound of Example 97 | 0.035 |
| Compound of Example 108 | 0.0007 |
| Compound of Example 113 | 0.00095 |
| Compound of Example 115 | 0.0011 |
| Cdmpound of Example 118 | 0.00084 |
| Compound of Example 124 | 0.002 |
| Compound of Example 126 | 0.0008 |
| Compound of Reference Example 4 | 0.11 |

The compounds of the present invention all showed a potent prolyl endopeptidase inhibition activity.

Among the compounds of formula (1), the compounds of Examples 13, 28, 41, 108 and 113 wherein R1—(X)n—(E)m—CO is 3-phenoxybenzoyl, and A: Phe is the same and the cycloalkyl group shown by Y1 is different, all exhibited a potent inhibition activity on almost the same level.

The prolyl endopeptidase inhibition activity was determined in the mouse brain administered with the compounds of the present invention, which is shown in Experiment 2 below.

Experiment 2

Prolyl endopeptidase inhibition activity in mouse brain

Method:

Each of the compounds of the present invention was dissolved in physiological saline or physiological saline added with a surfactant. The solution was intravenously administered to male ddy strain mice (3 in one group) at a dose of 30 mg/kg. For control, physiological saline or a surfactant alone was intravenously given to 3 mice in a similar manner.

Thirty minutes after administration, the animal was bled to death and the whole brain was excised out. Each brain was homogenized with 20-fold volume of 0.1 M phosphate buffer containing 2 mM DTT and the homogenate was centrifuged at 3000 g for 20 minutes. The prolyl endopeptidase in the resulting supernatant was determined as in Experiment 1, as β-naphthylamine isolated. When the mean enzyme activity in the mouse brain for control is made 100 (β-naphthylamine value: 3.88±0.26), the residual enzyme activity was determined when the compounds of the present invention was administered. The results are shown in Table 2.

TABLE 2

| Compound | Residual Enzyme Activity (%) |
|---|---|
| Compound of Example 26 | 5.7 |
| Compound of Example 64 | 50.5 |
| Compound of Example 84 | 50.3 |

EXAMPLES

Hereinafter the present invention will be specifically described with reference to Examples but is not deemed to be limited thereto. In Examples, amino acid residues all refer to L-form in steric configuration, unless otherwise indicated.

Reference Example 1

Synthesis of 2-hydroxy-2-(pyrrolidin-2-yl)acetic acid

After 4.98 g of N-benzyloxycarbonyl-D,L-proline was dissolved in 100 ml of dichloromethane, 2.12 g of 3,5-dimethylpyrazole and 4.5 g of dicyclohexylcarbodiimide were added to the solution. The temperature was reverted to room temperature 30 minutes after the addition and stirring was continued for 20 hours. At the end of the reaction, 0.3 ml of acetic acid was added to the reaction mixture. Insoluble matters were filtered off and the solvent was removed by distillation. The residue was dissolved in a small volume of ethyl acetate. After insoluble matters were filtered off, the filtrate was evaporated to dryness under vacuum to give 6.0 g (yield, 91.7%) of N-benzyloxycarbonyl-D,L-proline-3,5-dimethylpyrazolide.

After 1.37 g of lithium aluminum hydride was suspended in 20 ml of anhydrous THF, the suspension was cooled to −20° C. A solution of 5.88 g of N-benzyloxycarbonyl-D,L-proline-3,5-dimethylpyrazolide in 45 ml of anhydrous THF was dropwise added to the suspension over 30 minutes. After the dropwise addition, the reaction was carried out at the same temperature for 30 minutes. The reaction mixture was then cooled to −60° C. followed by neutralization with hydrochloric acid. Celite was added to the precipitates formed and filtered. After concentration, the precipitates were dissolved in ethyl acetate. The organic layer was washed with saturated sodium chloride aqueous solution and a solution of 1.8 g of sodium hydrogensulfite in 2 ml of water was added thereto followed by concentration. The residual concentrate was dissolved in 16 ml of water. After 32 ml of ethyl acetate was added to the solution, a solution of 1.1 g of potassium cyanide in 8 ml of water was added to the mixture. The mixture was then stirred for 3 hours.

To the reaction mixture was added 80 ml of ethyl acetate. After washing with water and then with saturated sodium chloride aqueous solution, the system was dried over anhydrous sodium sulfate. After anhydrous sodium sulfate was filtered off, the solvent was distilled off under vacuum to give an oily substance. The thus obtained oily substance was dissolved in 20 ml of conc. hydrochloric acid and 20 ml of dioxane. The solution was refluxed for 10 hours. The reaction solution was concentrated under vacuum. The residue was washed with ether to give 14 g (yield, 35.0%) of 2-hydroxy-2-(pyrrolidin-2-yl)acetic acid hydrochloride.

Reference Example 2

2-Hydroxy-2-[2-(1-t-butoxycarbonylpyrrolidinyl)]acetic acid

In 2 ml of water and 2.87 ml of 1 N—NaOH was dissolved 520 mg of 2-hydroxy-2-(2-pyrrolidinyl)acetic acid. Thereafter, a solution of 940 mg of di-t-butyl dicarbonate in 4 ml of dioxane was added to the solution under ice cooling followed by stirring at room temperature for 30 minutes. After stirring at room temperature for further 5 hours, 30 ml of ethyl acetate and 30 ml of saturated sodium hydrogencarbonate aqueous solution were added to the reaction mixture to fractionate the aqueous layer. The aqueous layer was adjusted pH to 3 with phosphoric acid, followed by extraction with ethyl acetate. The extract was dried over anhydrous sodium sulfate. After filtration, the filtrate was concentrated to give 800 mg of oily 2-hydroxy-2-[2-(1-t-butoxycarbonylpyrrolidinyl)]acetic acid. Yield, 52.0%.

1H-NMR (CDCl$_3$) δ:
  1.47, 1.48 (9H two s)
  1.7–2.4 (4H, m)
  3.3–3.6 (2H, m)
  4.1–4.5 (2H, m)
  4.4–5.2 (2H, br)

Example 1

N-Cyclohexyl-2-hydroxy-2-[2-(1-t-butoxycarbonylpyrrolidinyl)]acetamide

In 9 ml of DMF were dissolved 1.64 g of 2-hydroxy-2-[2-(1-t-butoxycarbonylpyrrolidinyl)]acetic acid and 1.36 g of 1-hydroxybenzotriazole. Under ice cooling, 0.80 g of cyclohexylamine and 1.61 g of 1-ethyl-3-(3-dimethylaminopropyl)carbodiimide hydrochloride were added to the solution. After stirring for 2 hours, stirring was continued at room temperature for further 4 hours. At the end of the reaction, 50 ml of ethyl acetate was added to the reaction mixture for dilution. The mixture was washed successively with 40 ml each of 4% sodium hydrogencarbonate aqueous solution, saturated sodium chloride aqueous solution, 1% citric acid aqueous solution and saturated sodium chloride aqueous solution. The oily layer was dried over anhydrous sodium sulfate and the solvent was then distilled off to give 21.7 g of a white solid. The solid was purified by column chromatography (Sephadex LH20, developed with methanol) to give 2.11 g of N-cyclohexyl-2-hydroxy-2-[2-(1-t-butoxycarbonylpyrrolidinyl)]acetamide as a white solid. Yield, 96.3%.

FAB-MS m/z 327 (M+1)$^+$

Example 2

N-Cyclohexyl-2-hydroxy-2-(2-pyyrrolidinyl) acetamide hydrochloride

To 1.99 g of N-cyclohexyl-2-hydroxy-2-[2-(1-t-butoxycarbonylpyrrolidinyl)]acetamide was added 40 ml of 4 N hydrochloric acid-dioxane solution under ice cooling. After stirring at room temperature for an hour, the solvent was distilled off to give 1.92 g of white solid. To the white solid was added 30 ml of ether. The mixture was stirred for 30 minutes in a suspended state, followed by filtration and drying. Thus, 1.61 g of N-cyclohexyl-2-hydroxy-2-(2-pyrrolidinyl)acetamide hydrochloride was obtained as a white solid in a quantitative yield.

Example 3

N-Cyclohexyl-2-hydroxy-2-[2-1-N-benzyloxycarbonylvalylpyrrolidinyl)]acetamide

In 3 ml of DMF were dissolved 341.8 mg of N-cyclohexyl-2-hydroxy-2-(2-pyrrolidinyl)acetamide hydrochloride, 343.3 mg of N-benzyloxycarbonylvaline and 351.3 mg of 1-hydroxybenzotriazole. Under ice cooling, 153 μl of N-methylmorpholine and 348.9 mg of 1-ethyl-3-(3-dimethylaminopropyl)carbodiimide hydrochloride were added to the solution. After stirring for 2 hours, the reaction mixture was stirred at room temperature for further 18 hours. The reaction solution was then diluted with 30 ml of ethyl acetate. The resulting mixture was washed successively with 20 ml each of 4% sodium hydrogencarbonate aqueous solution, saturated sodium chloride aqueous solution, 1% citric acid aqueous solution and saturated sodium chloride aqueous solution. The organic layer was dried over anhydrous sodium sulfate and the solvent was then distilled off under vacuum to give 804 mg of an oily substance. The oily substance was purified by column chromatography (silica gel, developed with dichloromethane-methanol) to give 525.9 mg of N-cyclohexyl-2-hydroxy- 2-[2-(N-benzyloxycarbonylvalyl)pyrrolidinyl)]acetamide as a colorless amorphous solid. Yield, 88.0%.

FAB-MS m/z 460 (M+1)$^+$

Example 4

N-Cyclohexyl-2-oxo-2-[2-(1-(N-benzyloxycarbonylvalyl)pyrrolidinyl)]acetamide

To 161.1 mg of N-cyclohexyl-2-hydroxy-2-[2-(1-(N-benzyloxycarbonylvalyl)pyrrolidinyl)]acetamide were added 34.0 mg of pyridine-trifluoroacetate, 201.6 mg of 1-ethyl-3-(3-dimethylaminopropyl)carbodiimide hydrochloride and 2.0 ml of DMSO. The mixture was stirred at room temperature for 22 hours. At the end of the reaction, the reaction solution was diluted with 20 ml of ethyl acetate and the diluted solution was washed with 15 ml of water. After drying over anhydrous sodium sulfate, the diluted solution was concentrated under vacuum to give 268 mg of an oily substance. The oily substance was purified by column chromatography (silica gel, developed with dichloromethane-acetonitrile) to give 120.8 mg of N-cyclohexyl-2-oxo-2-(2-(1-(N-benzyloxycarbonylvalyl) pyrrolidinyl)]acetamide as a colorless amorphous solid. Yield, 74.0%.

melting point: 55–57° C.

FAB-MS m/z 458 (M+1)$^+$

1H-NMR (CDCl$_3$) δ:
  0.93, 1.04 (6H, two d, each J=6.8Hz)
  1.10–1.45 (5H, m)
  1.56–1.78 (3H, m)
  1.83–2.12 (6H, m)
  2.39 (1H, m)
  3.66 (1H, m)
  3.72 (1H, m)
  3.85 (1H, m)
  4.34 (1H, dd, J=6.3, 9.3Hz)
  5.06, 5.09 (2H, ABq, J=12.5Hz)
  5.30 (1H, dd, J=7.1, 8.5Hz)
  5.40 (1H, d, J=9.3Hz)
  6.73 (1H, brd, J=8.3Hz)
  7.24–7.43 (5H, m)

Example 5

N-Cyclohexyl-2-hydroxy-2-[2-(1-valylpyrrolidinyl)] acetamide

After 364.4 mg of N-cyclohexyl-2-hydroxy-2-[2-(1-(N-benzyloxycarbonylvalyl)pyrrolidinyl)]acetamide was dissolved in 4 ml of methanol, the solution was subjected to catalytic hydrogenation at room temperature for 24 hours in the presence of palladium black. The catalyst was filtered off and the solvent was then removed by distillation under vacuum to give 258.0 mg of N-cyclohexyl-2-hydroxy-2-[2-(1-valylpyrrolidinyl)]acetamide as a colorless amorphous solid in a quantitative yield.

Example 6

N-Cyclohexyl-2-hydroxy-2-[2-(1-(N-(3-phenoxybenzoyl)valyl)pyrrolidinyl)]acetamide In 2 ml of DMF were dissolved, 127.7 mg of N-cyclohexyl-2-hydroxy-2-[2-(1-valylpyrrolidinyl)] acetamide, 90.7 mg of 3-phenoxybenzoic acid and 108.7 mg of 1-hydroxybenzotriazole. Under ice cooling, 107.9 mg of 1-ethyl-3-(3-dimethylaminopropyl)carbodiimide hydrochloride was added to the solution. After stirring for 2 hours, stirring was continued at room temperature for further 5 hours. Then the reaction mixture was diluted with 20 ml of ethyl acetate and washed successively with 10 ml each of 4% sodium hydrogencarbonate aqueous solution, 1% citric acid aqueous solution and saturated sodium chloride aqueous solution. The organic layer was dried over anhydrous sodium sulfate and the solvent was then distilled off under vacuum to give an oily substance. The oily substance was purified by column chromatography (silica gel,. developed with dichloromethane-methanol) to give 187.9 mg of N-cyclohexyl-2-hydroxy-2-[2-(1-(N-(3-phenoxybenzoyl) valyl)pyrrolidinyl)]acetamide as a colorless amorphous solid. Yield, 91.8%.

FAB-MS m/z 522 (M+1)$^+$

Example 7

N-Cyclohexyl-2-oxo-2-[2-(1-(N-(3-phenoxybenzoyl) valyl)pyrrolidinyl)]acetamide

To 187.3 mg of N-cyclohexyl-2-hydroxy-2-[2-(1-(N-(3-phenoxybenzoyl)valyl)pyrrolidinyl)]acetamide were added 0.68 ml of acetic anhydride and 0.6 ml of DMSO. The mixture was stirred at room temperature for 24 hours. At the end of the reaction, 15 ml of water was added to the reaction solution and the mixture was stirred for 30 minutes. Thereafter the aqueous layer was extracted with 3 times with 10 ml each of dichloromethane. After drying over anhydrous sodium sulfate, the oily layer was concentrated under vacuum to give 623 mg of an oily substance. The oily substance was purified by column chromatography (silica gel, developed with dichloromethane-acetonitrile) to give 169.5 mg of N-cyclohexyl-2-oxo-2-[2-(1-(N-(3-phenoxybenzoyl)valyl)pyrrolidinyl)]acetamide as a colorless amorphous solid. Yield, 90.8%.

melting point: 70–72° C.

[α]27/D–83.7° (cl. 00, CHCl$_3$)

FAB-MS m/z 520 (M+1)$^+$

1H-NMR (CDCl$_3$) δ:
  1.00, 1.09 (6H, two d, each J=6.4Hz)
  ca. 1.14–1.46 (5H, m, overlapping)
  1.54–1.82 (3H, m)
  1.83–2.11 (5H, m)
  2.18 (1H, m)
  2.40 (1H, m)
  3.64–3.81 (2H, m)
  3.96 (1H, dt, J=6.1, 10.3Hz)
  4.83 (1H, dd, J=6.3, 8.8Hz)
  5.31 (1H, dd, J=7.1, 8.5Hz)
  6.75 (1H, d, J=8.3Hz)
  6.93 (1H, d, J=8.8Hz)
  5 7.01 (2H, m)
  7.12 (2H, m)
  7.28–7.56 (5H, m)

Example 8

N-Cyclohexyl-2-hydroxy-2-[2-(1-(N-(2-Quinolinecarbonyl)valyl)pyrrolidinyl)]acetamide In 2 ml of DMF were dissolved 130.3 mg of N-cyclohexyl-2-hydroxy-2-[2-(1-valylpyrrolidinyl)] acetamide, 73.6 mg of quinaldinic acid and 108.2 mg of 1-hydroxybenzotriazole. Under ice cooling, 107.5 mg of 1-ethyl-3-(3-dimethylaminopropyl)carbodiimide hydrochloride was added to the solution. After stirring for 2 hours, the reaction mixture was stirred at room temperature for further 14 hours. The reaction solution was then diluted with 20 ml of ethyl acetate. The resulting mixture was washed successively with 15 ml each of 4% sodium hydrogencarbonate aqueous solution and saturated sodium chloride aqueous solution. The organic layer was dried over anhydrous sodium sulfate and the solvent was then distilled off under vacuum to give 351 mg of an oily substance. The oily substance was purified by column chromatography (silica gel, developed with dichloromethane-methanol-triethylamine) to give 188.4 mg of N-cyclohexyl-2-hydroxy-2-[2-1-(N-(2-quinolinecarbonyl)valyl)pyrrolidinyl)] acetamide as a colorless amorphous solid. Yield, 97.9%.

FAB-MS m/z 481 (M+1)$^+$

Example 9

N-Cyclohexyl-2-oxo-2-[2-(1-(N-(2-quinolinecarbonyl)valyl)pyrrolidinyl)]acetamide To 188.0 mg of N-cyclohexyl-2-hydroxy-2-[2-(1-(N-(2-quinolinecarbonyl)valyl)pyrrolidinyl)]acetamide were added 0.74 ml of acetic anhydride and 0.7 ml of DMSO. The mixture was stirred at room temperature for 24 hours. At the end of the reaction, 15 ml of 4% sodium hydrogencarbonate aqueous solution was added to the reaction solution and the mixture was stirred for 30 minutes. Thereafter the aqueous layer was extracted with 3 times with 10 ml each of dichloromethane. After drying over anhydrous sodium sulfate, the oily layer was concentrated under vacuum to give an oily substance. The oily substance was purified by column chromatography (silica gel, developed with dichloromethane-acetonitrile-acetic acid) to give 86.7 mg of N-cyclohexyl-2-oxo-2-[2-(1-(N-(2-quinoline-carbonyl) valyl)pyrrolidinyl)]acetamide as colorless transparent crystals. Yield, 46.3%.

melting point: 145.5–146.5° C.

[α]26/D–35.6° (cl. 00, CHCl$_3$)

FAB-MS m/z 479 (M+1)$^+$

1H-NMR (CDCl$_3$) δ:
  1.07, 1.14 (6H, two d, J=6.4Hz, J=6.8Hz)
  ca. 1.15–1.47 (5H, m, overlapping)
  1.60–1.83 (3H, m)
  1.86–2.14 (5H, m)
  2.30 (1H, m)
  2.40 (1H, m)
  3.67–3.85 (2H, m)
  4.01 (1H, dt, J=6.3, 9.8Hz)
  4.88 (1H, dd, J=7.3, 9.8Hz)
  5.33 (1H, dd, J=6.8, 8.3Hz)
  6.78 (1H, d, J=8.3Hz)
  7.60, 7.75 (2H, two m)

7.86, 8.14, 8.25, 8.29 (4H, four d)
8.78 (1H, d, J=9.8Hz)

Example 10

N-Cyclopentyl-2-hydroxy-2-[2-(1-t-butoxycarbonylpyrrolidinyl)]acetamide

In 2 ml of DMF were dissolved 152.8 mg of 2-hydroxy-2-[2-(1-t-butoxycarbonylpyrrolidinyl)]acetic acid and 126.4 mg of 1-hydroxybenzotriazole. Under ice cooling, 63.9 mg of cyclopentylamine and 149.3 mg of 1-ethyl-3-(3-dimethylaminopropyl)carbodiimide hydrochloride were added to the solution. After stirring for 2 hours, stirring was continued at room temperature for further 4 hours. At the end of the reaction, 20 ml of ethyl acetate was added to the reaction mixture for dilution. The mixture was washed successively with 10 ml each of 4% sodium hydrogencarbonate aqueous solution, saturated sodium chloride aqueous solution, 1% citric acid aqueous solution and saturated sodium chloride aqueous solution. The oily layer was dried over anhydrous sodium sulfate and the solvent was then distilled off to give 205.6 mg of white solid. Next, the solid was purified by column chromatography (Sephadex LH20, developed with methanol) to give 181.1 mg of N-cyclopentyl-2-hydroxy-2-[2-(1-t-butoxycarbonylpyrrolidinyl)]acetamide as a white solid. Yield, 93.1%.

FAB-MS m/z 313 (M+1)$^+$

Example 11

N-Cyclopentyl-2-hydroxy-2-[2-(1-(N-t-butoxycarbonylphenylalanyl)pyrrolidinyl)acetamide To 88.6 mg of N-cyclopentyl-2-hydroxy-2-(2-(1-t-butoxycarbonylpyrrolidinyl)]acetamide was added 1.5 ml of trifluoroacetic acid. After stirring at room temperature for 40 minutes, the solvent was distilled off and 2 ml of toluene was added to the residue followed by distilling off the solvent. This cycle of the procedures was repeated 3 times to give N-cyclopentyl-2-hydroxy-2-(2-pyrrolidinyl)acetamide trifluoroacetate as an amorphous solid. After 90.3 mg of N-t-butoxycarbonylphenylalanine, 87.1 mg of 1-hydroxybenzotriazole and 1 ml of DMF were added to the solid, 48 μl of triethylamine and 86.5 mg of 1-ethyl-3-(3-dimethylaminopropyl)carbodiimide hydrochloride were added to the mixture. After stirring for 2 hours, stirring was continued at room temperature for further 22 hours. Thereafter, the reaction solution was diluted with 15 ml of ethyl acetate and the diluted solution was washed successively with 10 ml each of 4% sodium hydrogencarbonate aqueous solution and 1% citric acid aqueous solution. The organic layer was dried over-anhydrous sodium sulfate and the solvent was then distilled off to give an amorphous solid. The solid was purified by column chromatography (silica gel, developed with dichloromethane-methanol) to give 80.9 mg of N-cyclopentyl-2-hydroxy-2-[2-(1-(N-t-butoxycarbonylphenylalanyl)pyrrolidinyl)]acetamide as a colorless amorphous solid. Yield, 62.1%.

FAB-MS m/z 460 (M+1)$^+$

Example 12

N-Cyclopentyl-2-hydroxy-2-[2-(1-(N-(3-phenoxybenzoyl)phenylalanyl)pyrrolidinyl)] acetamide To 80.6 mg of N-cyclopentyl-2-hydroxy-2-[2-(1-(N-t-butoxycarbonylphenylalanyl)pyrrolidinyl)]acetamide was added 1.5 ml of trifluoroacetic acid. After stirring at room temperature for 40 minutes, the solvent was distilled off and 2 ml of toluene was added to the residue followed by distilling off the solvent. This cycle of the procedures was repeated 3 times to give N-cyclopentyl-2-hydroxy-2-[2-(1-phenylalanylpyrrolidinyl)]acetamide trifluoroacetate as an amorphous solid. After 39.5 mg of 3-phenoxybenzoic acid, 47.9 mg of 1-hydroxybenzotriazole and 1 ml of DMF were added to the solid, 29 μl of triethylamine and 47.1 mg of 1-ethyl-3-(3-dimethylaminopropyl)carbodiimide hydrochloride were added to the mixture. After stirring for 2 hours, stirring was continued at room temperature for further 22 hours. Thereafter, the reaction solution was diluted with 10 ml of ethyl acetate and the diluted solution was washed successively with 5 ml each of 4% sodium hydrogencarbonate aqueous solution, 1% citric acid aqueous solution and saturated sodium chloride aqueous solution. The organic layer was dried over anhydrous sodium sulfate and the solvent was then distilled off under vacuum to give 122.5 mg of the amorphous solid. The solid was purified by column chromatography (silica gel, developed with dichloromethane-methanol) to give 91.9 mg of N-cyclopentyl-2-hydroxy-2-[2-(1-(N-(3-phenoxybenzoyl) phenylalanyl)pyrrolidinyl)]acetamide as a colorless amorphous solid. Yield, 94.5%.

FAB-MS m/z 556 (M+1)$^+$

Example 13

N-Cyclopentyl-2-oxo-2-[2-(1-(N-(3-phenoxybenzoyl)phenylalanyl)pyrrolidinyl)] acetamide To 91.6 mg of N-cyclopentyl-2-hydroxy-2-[2-( 1-(N-(3-phenoxybenzoyl)phenylalanyl)pyrrolidinyl)]acetamide were added 312 μl of acetic anhydride and 0.5 ml of DMSO. The mixture was stirred at room temperature for 26 hours. At the end of the reaction, 20 ml of water was added to the reaction solution and the mixture was stirred for 30 minutes. Thereafter the aqueous layer was extracted with 3 times with 10 ml each of dichloromethane. After drying over anhydrous sodium sulfate, the oily layer was concentrated under vacuum to give 314 mg of an oily substance. The oily substance was purified by column chromatography (silica gel, developed with dichloromethane-acetonitrile) to give 89.0 mg of N-cyclopentyl-2-oxo-2-[2-(1-(N-(3-phenoxybenzoyl)phenylalanyl)pyrrolidinyl)]acetamide as a colorless amorphous solid. Yield, 97.5%.

melting point: 70–72° C.
[α28/D–45.1° (cl. 01, CHCl$_3$)
FAB-MS m/z 554 (M+1)$^+$
1H-NMR (CDCl$_3$) δ:
 1.35–1.80 (6H, m)
 1.81–2.15 (5H, m)
 2.33 (1H, m)
 3.07 (1H, dd, J=5.9, 13.7Hz)
 ca. 3.12 (1H, m)
 3.18 (1H, dd, J=7.3, 13.7Hz)
 3.70 (1H, m)
 4.18 (1H, sestet, J=7.0Hz)
 5.11 (1H, ddd, J=5.9, 7.3, 8.3Hz)
 5.33 (1H, dd, J=6.1, 8.5Hz)
 6.84 (1H, d, J=7.8Hz)
 6.93 (1H, d, J=8.3Hz)
 6.98–7.50 (14H, m)

Example 14

N-Cyclohexyl-2-hydroxy-2-[2-(1-(N-t-butoxycarbonylphenylalanyl)pyrrolidinyl)]acetamide After 763.3 mg of N-t-butoxycarbonylphenylalanine, 740.6 mg of 1-hydroxybenzotriazole and 6 ml of DMF were added to 720.9 mg of N-cyclohexyl-2-hydroxy-2-(2-pyrrolidinyl)]acetamide hydrochloride, 403 µl of triethylamine and 735.3 mg of 1-ethyl-3-(3-dimethylaminopropyl) carbodiimide hydrochloride were added to the solution under ice cooling. After stirring for 2 hours, stirring was continued at room temperature for further 4 hours. Thereafter the reaction solution was diluted with 60 ml of ethyl acetate and the diluted solution was washed successively with 40 ml each of 4% sodium hydrogencarbonate aqueous solution, saturated sodium chloride aqueous solution, 1% citric acid aqueous solution and saturated sodium chloride aqueous solution. The organic layer was dried over anhydrous sodium sulfate. The solvent was then distilled off under vacuum to give 1.544 g of a gum-like substance. The substance was purified by column chromatography (silica gel, developed with dichloromethane-methanol) to give 1.225 g of N-cyclohexyl-2-hydroxy-2-[2-(1-(N-t-butoxycarbonylphenylalanyl)pyrrolidinyl)]acetamide as a white solid. Yield, 94.3%.

FAB-MS m/z 474 (M+1)$^+$

Example 15

N-Cyclohexyl-2-oxo-2-[2-(1-(N-t-butoxycarbonylphenylalanyl)pyrrolidinyl)]acetamide To 214.5 mg of N-cyclohexyl-2-hydroxy-2-[2-(1-(N-t-butoxycarbonylphenylalanyl)pyrrolidinyl)]acetamide were added 43.8 mg of pyridine-trifluoroacetate, 260.5 mg of 1-ethyl-3-(3-dimethylaminopropyl)carbodiimide hydrochloride and 2.0 ml of DMSO. The mixture was stirred at room temperature for 9 hours. At the end of the reaction, the reaction solution was diluted with 20 ml of ethyl acetate and the diluted solution was washed with 10 ml of water. After drying over anhydrous sodium sulfate, the diluted solution was concentrated under vacuum to give 369 mg of an oily substance. The oily substance was purified by column chromatography (silica gel, developed with dichloromethane-acetonitrile) to give 171.3 mg of N-cyclohexyl-2-oxo-2-[2-(1-(N-t-butoxycarbonylphenylalanyl)pyrrolidinyl)] acetamide as a colorless amorphous solid. Yield, 80.2%.

melting point: 65–67° C.
[α]24/D–26.6° (cl. 03, CHCl$_3$)
FAB-MS m/z 472 (M+1)$^+$
1H-NMR (CDCl$_3$) δ:
 1.08–1.48 (5H, m)
 1.37 (9H, s)
 1.55–2.06 (8H, m)
 2.32 (1H, m)
 2.88 (1H, dd, J=6.8, 13.7Hz)
 3.06 (1H, dd, J=7.1, 13.7Hz)
 ca. 3.09 (1H, m, overlapping)
 3.64 (1H, m)
 3.74 (1H, m)
 4.64 (1H, ddd, J=6.8, 7.1, 8.6Hz)
 5.23 (1H, J=8.6Hz)
 5.32 (1H, dd, J=5.8, 8.4Hz)
 6.79 (1H, d, J=8.2Hz)
 7.17–7.37 (5H, m)

Example 16

N-Cyclohexyl-2-hydroxy-2-[2-(1-phenylalanylpyrrolidinyl]acetamide hydrochloride

To 613.6 mg of N-cyclohexyl-2-hydroxy-2-[2-(1-(N-t-butoxycarbonylphenylalanyl)pyrrolidinyl)]acetamide was added 10 ml of 4 N hydrochloric acid-dioxane solution under ice cooling. After stirring at room temperature for an hour, the solvent was distilled off to give a white solid. To the white solid was added 10 ml of ether. The mixture was stirred for 30 minutes in a suspended state, followed by filtration and drying. Thus, 521.3 mg of N-cyclohexyl-2-hydroxy-2-[2-(1-phenylalanylpyrrolidinyl)]acetamide hydrochloride was obtained as a white solid. Yield, 98.2%.

Example 17

N-Cyclohexyl-2-hydroxy-2-[2-(1-(N-(2-thenoyl) phenylalanyl pyrrolidinyl)]acetamide To 132.6 mg of N-cyclohexyl-2-hydroxy-2-[2-(1-phenylalanyl)pyrrolidinyl)]acetamide hydrochloride were added 1.3 ml of dry tetrahydrofuran and 100 µl of triethylamine. A solution of 38 µl of 2-thiophenecarbonyl chloride in 3 ml of dry tetrahydrofuran was then dropwise added to the mixture over 30 minutes. After completion of the dropwise addition, the mixture was stirred for 2 hours and the solvent was distilled off under vacuum. After 6 ml of 1 N hydrochloric acid was added to the solid obtained, the mixture was extracted once with 8 ml of ethyl acetate and twice with 4 ml of ethyl acetate. The oily layers were combined and washed successively with 12 ml each of saturated sodium hydrogencarbonate aqueous solution and saturated sodium chloride aqueous solution. The oily layer was dried over anhydrous sodium sulfate and the solvent was then distilled off under vacuum to give an amorphous solid. The solid was purified by column chromatography (silica gel, developed with dichloromethane-methanol) to give 154.0 mg of N-cyclohexyl-2-hydroxy-2-[2-(1-(N-(2-thenoyl)phenylalanyl)-pyrrolidinyl)]acetamide as a colorless amorphous solid. Yield, 98.4%.

FAB-MS m/z 484 (M+1)$^+$

Example 18

N-Cyclohexyl-2-oxo-2-[2-(1-(N-(2-thenoyl) phenylalanyl)pyrrolidinyl)]acetamide

To 154.0 mg of N-cyclohexyl-2-hydroxy-2-[2-(1-(N-(2-thenoyl)phenylalanyl)pyrrolidinyl)]acetamide were added 0.60 ml of acetic anhydride and 0.60 ml of DMSO. The mixture was stirred at room temperature for 25 hours. At the end of the reaction, 15 ml of water was added to the reaction solution and the mixture was stirred for an hour. Thereafter the aqueous layer was extracted with 3 times with 10 ml each of dichloromethane. After drying over anhydrous sodium sulfate, the oily layer was concentrated under vacuum to give an oily substance. The oily substance was purified by column chromatography (silica gel, developed with dichloromethane-acetonitrile) to give 117.5 mg of N-cyclohexyl-2-oxo-2-[2-(1-(N-(2-thenoyl)phenylalanyl) pyrrolidinyl)]acetamide as a colorless amorphous solid. Yield, 76.6%.

melting point: 88–91° C.
[α]27/D–58.2° (cl. 0.2, CHCl$_3$)
FAB-MS m/z 482 (M+1)$^+$
1H-NMR (CDCl$_3$) δ:
 1.11–1.48 (5H, m)
 1.52–2.06 (8H, m)
 2.34 (1H, m)
 3.10 (1H, dd, J=5.9, 13.7Hz)
 ca. 3.11 (1H, m, overlapping)
 3.17 (1H, dd, J=7.3, 13.7Hz)
 3.65–3.81 (2H, m)
 5.10 (1H, ddd, J=5.9, 7.3, 8.3Hz)

5.38 (1H, dd, J=5.9, 8.8Hz)
6.78 (1H, d, J=8.3Hz)
6.98 (1H, d, J=8.3Hz)
7.05 (1H, m)
7.19–7.53 (7H, m)

Example 19

N-Cyclohexyl-2-hydroxy-2-[2-(1-(N-phenoxyacetylphenylalanyl)pyrrolidinyl)]acetamide To 167.1 mg of N-cyclohexyl-2-hydroxy-2-[2-(1-(N-t-butoxycarbonylphenylalanyl)pyrrolidinyl)]acetamide was added 1.6 ml of trifluoroacetic acid. After stirring at room temperature for 40 minutes, the solvent was distilled off and 2 ml of toluene was added to the residue followed by distilling off the solvent. This cycle of the procedures was repeated twice to give N-cyclohexyl-2-hydroxy-2-[2-(1-phenylalanylpyrrolidinyl)]acetamide trifluoroacetate as an amorphous solid. After 1.5 ml of dry tetrahydrofuran and 119 μl of triethylamine were added to the solid, a solution of 59 μl of phenoxyacetyl chloride in 3 ml of dry tetrahydrofuran was dropwise added to the mixture over 30 minutes. After completion of the dropwise addition, the reaction mixture was stirred for 2 hours and the solvent was distilled off under vacuum. To the resulting solid was added 20 ml of ethyl acetate. The mixture was washed successively with 6 ml each of 1 N hydrochloric acid, saturated sodium hydrogencarbonate aqueous solution and saturated sodium chloride aqueous solution. The organic layer was dried over anhydrous sodium sulfate and the solvent was then distilled off under vacuum to give an amorphous solid. The solid was purified by column chromatography (silica gel, developed with dichloromethane-methanol) to give 172.6 mg of N-cyclohexyl-2-hydroxy-2-[2-(1-(N-phenoxyacetylphenylalanyl)pyrrolidinyl)]acetamide as a colorless amorphous solid. Yield, 96.4%.

FAB-MS m/z 508 (M+1)$^+$

Example 20

N-Cyclohexyl-2-oxo-2-[2-(1-(N-phenoxyacetylphenylalanyl)pyrrolidinyl)]acetamide

To 122.1 mg of N-cyclohexyl-2-hydroxy-2-[2-(1-(N-phenoxyacetylphenylalanyl)pyrrolidinyl)]acetamide were added 450 μl of acetic anhydride and 0.5 ml of DMSO. The mixture was stirred at room temperature for 21.5 hours. At the end of the reaction, 10 ml of water was added to the reaction solution and the mixture was stirred for an hour. Thereafter the aqueous layer was extracted with twice with 10 ml each of dichloromethane. After drying over anhydrous sodium sulfate, the oily layer was concentrated under vacuum to give an oily substance. The oily substance was purified by column chromatography (silica gel, developed with dichloromethane-acetonitrile) to give 94.3 mg of N-cyclohexyl-2-oxo-2-[2-(1-(N-phenoxyacetylphenylalanyl)pyrrolidinyl)]acetamide as a colorless amorphous solid. Yield, 77.5%. The amorphous solid was treated with dichloromethane-hexane to give needles.

melting point: 77–79° C.
[α]23/D–26.3° (c 1.12, CHCl$_3$)
FAB-MS m/z 506 (M+1)$^+$
1H-NMR (CDCl$_3$) δ:
1.10–1.50 (5H, m)
1.54–2.05 (8H, m)
2.33 (1H, m)
2.96 (1H, dd, J=6.6, 13.9Hz)
3.14 (1H, dd, J=6.9, 13.9Hz)
ca. 3.14 (1H, m, overlapping)
3.61–3.84 (2H, m)
4.41, 4.43 (2H, ABq, J=14.9Hz)
5.06 (1H, ddd, J=6.6, 6.9, 8.6Hz)
5.33 (1H, dd, J=5.9, 8.6Hz)
6.80 (1H, d, J=8.3Hz)
ca. 6.76–7.40 (11H, m, overlapping)

Example 21

N-Cyclohexyl-2-hydroxy-2-[2-(1-(N-(2-naphthoyl)phenylalanyl)pyrrolidinyl)]acetamide To 162.3 mg of N-cyclohexyl-2-hydroxy-2-[2-(1-(N-t-butoxycarbonylphenylalanyl)pyrrolidinyl)]acetamide was added 1.6 ml of trifluoroacetic acid. After stirring at room temperature for 40 minutes, the solvent was distilled off and 2 ml of toluene was added to the residue followed by distilling off the solvent. This cycle of the procedures was repeated twice to give N-cyclohexyl-2-hydroxy-2-[2-(1-phenylalanylpyrrolidinyl)]acetamide trifluoroacetate as an amorphous solid. After 62.0 mg of 2-naphthoenic acid, 93.4 mg of 1-hydroxybenzotriazole and 2 ml of DMF were added to the solid, 58 μl of triethylamine and 92.0 mg of 1-ethyl-3-(3-dimethylaminopropyl)carbodiimide hydrochloride were added to the mixture. After stirring for 2 hours, stirring was continued at room temperature for further 20 hours. Thereafter, the reaction solution was diluted with 20 ml of ethyl acetate and the diluted solution was washed successively with 10 ml each of 4% sodium hydrogencarbonate aqueous solution, 1% citric acid aqueous solution and saturated sodium chloride aqueous solution. The organic layer was dried over anhydrous sodium sulfate and then concentrated under vacuum to give an amorphous solid. The solid was purified by column chromatography (silica gel, developed with dichloromethane-methanol) to give 176.8 mg of N-cyclohexyl-2-hydroxy-2-[2-(1-(N-(2-naphthoyl)phenylalanyl)pyrrolidinyl)]acetamide as a colorless amorphous solid. Yield, 97.8%.

FAB-MS m/z 528 (M+1)$^+$

Example 22

N-Cyclohexyl-2-oxo-2-[2-(1-(N-(2-naphthoyl)phenylalanyl)pyrrolidinyl)]acetamide

To 176.1 mg of N-cyclohexyl-2-hydroxy-2-[2-(1-(N-(2-naphthoyl)phenylalanyl)pyrrolidinyl)]acetamide were added 630 μl of acetic anhydride and 0.6 ml of DMSO. The mixture was stirred at room temperature for 26 hours. At the end of the reaction, 15 ml of water was added to the reaction solution and the mixture was stirred for 2 hours. Thereafter the aqueous layer was extracted with twice with 10 ml each of dichloromethane. After drying over anhydrous sodium sulfate, the oily layer was concentrated under vacuum to give an oily substance. The oily substance was purified by column chromatography (silica gel,. developed with dichloromethane-acetonitrile) to give 137.7 mg of N-cyclohexyl-2-oxo-2-[2-(1-(N-(2-naphthoyl)phenylalanyl)pyrrolidinyl)]acetamide as crystals. Yield, 78.5%.

melting point: 181–184° C.
[α]23/D–53.5° (c 1.15, CHCl$_3$)
FAB-MS m/z 526 (M+1)$^+$
1H-NMR (CDCl$_3$) δ:
1.06–1.50 (5H, m)
1.54–2.06 (8H, m)

2.36 (1H, m)
3.16 (1H, dd, J=5.6, 13.5Hz)
ca. 3.17 (1H, m, overlapping)
3.26 (1H, dd, J=7.3, 13.5Hz)
3.66–3.86 (2H, m)
5.22 (1H, ddd, J=5.6, 7.3, 7.6Hz)
5.39 (1H, dd, J=6.3, 8.6Hz)
6.82 (1H, d, J=8.3Hz)
7.21 (1H, d, J=7.6Hz)
ca. 7.14–8.31 (12H, m, overlapping)

Example 23

N-Cyclohexyl-2-hydroxy-2-[2-(1-(N-(2-pyridyl)acetylphenylalanyl)pyrrolidinyl)]acetamide After 65.6 mg of 2-pyridylacetic acid hydrochloride, 97.1 mg of 1-hydroxybenzotriazole and 2 ml of DMF were added to 132.9 mg of N-cyclohexyl-2-hydroxy-[2-(1-phenylalanylpyrrolidinyl)]acetamide, 56 µl of triethylamine and 95.5 mg of 1-ethyl-3-(3-dimethylaminopropyl) carbodiimide hydrochloride were added to the solution under ice cooling. After stirring for 2 hours, stirring was continued at room temperature for further 22 hours. Thereafter the reaction solution was diluted with 20 ml of ethyl acetate and the diluted solution was washed successively with 15 ml each of 4% sodium hydrogencarbonate aqueous solution and saturated sodium chloride aqueous solution. The organic layer was dried over anhydrous sodium sulfate and concentrated under vacuum to give an amorphous solid. The solid was purified by column chromatography (silica gel, developed with dichloromethane-methanol) to give 149.2 mg of N-cyclohexyl-2-hydroxy-2-[2-(1-(N-(2-pyridyl)acetylphenylalanyl)pyrrolidinyl)]acetamide as amorphous solid. Yield, 85.1%.

FAB-MS m/z 493 (M+1)$^+$

Example 24

N-Cyclohexyl-2-oxo-2-[2-(1-(N-(2-pyridyl)acetylphenylalanyl)pyrrolidinyl)]acetamide To 149.2 mg of N-cyclohexyl-2-hydroxy-2-[2-(1-(N-(2-pyridyl)acetylphenylalanyl)pyrrolidinyl)]acetamide were added 29.9 mg of pyridine-trifluoroacetate, 174.2 mg of 1-ethyl-3-(3-dimethylaminopropyl)carbodiimide hydrochloride and 2.0 ml of DMSO. The mixture was stirred at room temperature for 24 hours. At the end of the reaction, a sodium hydrogencarbonate aqueous solution (13 mg of sodium hydrogencarbonate was dissolved in 20 ml of water) was added to the reaction solution followed by extraction 3 times with 10 ml each of dichloromethane. After washing with 15 ml of water, the oily layer was dried over anhydrous sodium sulfate and concentrated under vacuum to give 145 mg of yellow amorphous solid. The solid was purified by column chromatography (silica gel, developed with chloroform-methanol-acetic acid) and again purified by column chromatography (LH-20, developed with methanol-acetic acid) to give 33.6 mg of an amorphous solid. The solid was purified by thin layer chromatography (silica gel, multiple development by dichloromethane-ethyl acetate-acetonitrile). The desired fraction was scraped out to give 11.5 mg of N-cyclohexyl-2-oxo-2-[2-(1-(N-(2-pyridyl)acetylphenylalanyl)pyrrolidinyl)]acetamide as an amorphous solid. Yield, 7.7%.

FAB-MS m/z 491 (M+1)$^+$
1H-NMR (CDCl$_3$) δ:
1.05–1.47 (5H, m)
1.52–2.05 (8H, m)
2.31 (1H, m)
2.91 (1H, dd, J=6.3, 13.7Hz)
3.07 (1H, dd, J=6.8, 13.7Hz)
3.13 (1H, m)
3.64, 3.69 (2H, ABq, J=15.6Hz)
ca. 3.60–3.80 (2H, m, overlapping)
4.95 (1H, ddd, J=6.3, 6.8, 7.8Hz)
5.30 (1H, dd, J=5.6, 8.5Hz)
6.78 (1H, d, J=8.3Hz)
7.05–7.32 (7H, m)
7.61 (1H, m)
7.81 (1H, d, J=7.8Hz)
8.52 (1H, m)

Example 25

N-Cyclohexyl-2-hydroxy-2-[2-(1-(N-(2-pyridylcarbonyl)phenylalanyl)pyrrolidinyl)]acetamide To 167.5 mg of N-cyclohexyl-2-hydroxy-2-[2-(1-t-butoxycarbonylphenylalanyl)pyrrolidinyl)]acetamide was added 1.6 ml of trifluoroacetic acid. After stirring at room temperature for 40 minutes, the solvent was distilled off and 2 ml of toluene was added to the residue followed by distilling off the solvent. This cycle of the procedures was repeated twice to give N-cyclohexyl-2-hydroxy-2-(2-pyrrolidinyl)acetamide trifluoroacetate as an amorphous solid. After 45.9 mg of picolinic acid, 96.0 mg of 1-hydroxybenzotriazole and 2 ml of DMF were added to the solid, 59 µl of triethylamine and 94.9 mg of 1-ethyl-3-(3-dimethylaminopropyl)carbodiimide hydrochloride were added to the mixture. After stirring for 2 hours, stirring was continued at room temperature for further 4 hours. Thereafter, the reaction solution was diluted with 20 ml of ethyl acetate and the diluted solution was washed successively with 15 ml each of 4% sodium hydrogencarbonate aqueous solution and saturated sodium chloride aqueous solution. The organic layer was dried over anhydrous sodium sulfate and then concentrated under vacuum to give a light yellow amorphous solid. The solid was purified by column chromatography (silica gel, developed with dichloromethane-methanol-triethylamine) to give 160.2 mg of N-cyclohexyl-2-hydroxy-2-[2-(1-(N-( 2-pyridylcarbonyl)phenylalanyl)pyrrolidinyl)]acetamide as a colorless amorphous solid. Yield, 94.6%.

FAB-MS m/z 479 (M+1)$^+$

Example 26

N-Cyclohexyl-2-oxo-2-[2-(1-(N-(2-pyridylcarbonyl)phenylalanyl)pyrrolidinyl)]acetamide To 136.6 mg of N-cyclohexyl-2-hydroxy-2-[2-(1-(N-(2-pyridylcarbonyl)phenylalanyl)pyrrolidinyl)]acetamide were added 540 µl of acetic anhydride and 0.5 ml of DMSO. The mixture was stirred at room temperature for 24 hours. At the end of the reaction, 10 ml of water was added to the reaction solution followed by stirring for 30 minutes. The resulting aqueous layer was extracted 3 times with 10 ml each of dichloromethane. The oily layers were combined and washed with 10 ml of water. The mixture was dried over anhydrous sodium sulfate and concentrated under vacuum to give 231 mg of an oily substance. The oily substance was purified by column chromatography (silica gel, developed with dichloromethane-acetonitrile-acetic acid) to give 92.8 mg of N-cyclohexyl-2-oxo-2-[2-(1-(N-(2-pyridylcarbonyl)phenylalanyl)pyrrolidinyl)]acetamide as crystals. Yield, 68.2%.

melting point: 138–139° C.

[α]22/D–53.4° (c 1.02, CHCl$_3$)

FAB-MS m/z 477 (M+1)$^+$

1H-NMR (CDCl$_3$) δ:
  1.08–1.50 (5H, m)
  1.52–2.06 (8H, m)
  2.31 (1H, m)
  3.08 (1H, dd, J=6.4, 13.7Hz)
  ca. 3.11 (1H, m, overlapping)
  3.23 (1H, dd, J=7.4, 13.7Hz)
  3.64–3.84 (2H, m, overlapping)
  5.14 (1H, ddd, J=6.4, 7.4, 8.6Hz)
  5.33 (1H, dd, J=5.9, 8.6Hz)
  6.80 (1H, d, J=8.3Hz)
  7.18–7.47 (6H, m)
  7.81 (1H, m)
  8.08 (1H, m)
  8.54 (1H, m)
  8.67 (1H, d, J=8.6Hz)

Example 27

N-Cyclohexyl-2-hydroxy-2-[2-(1-(N-(3-phenoxybenzoyl)phenylalanyl)pyrrolidinyl)]acetamide To 168.9 mg of N-cyclohexyl-2-hydroxy-2-[2-(1-(N-t-butoxycarbonylphenylalanyl)pyrrolidinyl)]acetamide was added 1.6 ml of trifluoroacetic acid. After stirring at room temperature for 40 minutes, the solvent was distilled off and 2 ml of toluene was added to the residue followed by distilling off the solvent. This cycle of the procedures was repeated twice to give N-cyclohexyl-2-hydroxy-2-[2-(1-phenylalanylpyrrolidinyl)]acetamide trifluoroacetate as an amorphous solid. After 80.5 mg of 3-phenoxybenzoic acid, 96.4 mg of 1-hydroxybenzotriazole and 2 ml of DMF were added to the solid, 60 μl of triethylamine and 95.7 mg of 1-ethyl-3-(3-dimethylaminopropyl)carbodiimide hydrochloride were added to the mixture. After stirring for 2 hours, stirring was continued at room temperature for further 21 hours. Thereafter, the reaction solution was diluted with 20 ml of ethyl acetate and the diluted solution was washed successively with 10 ml each of 4% sodium hydrogencarbonate aqueous solution, 1% citric acid aqueous solution and saturated sodium chloride aqueous solution. The organic layer was dried over anhydrous sodium sulfate and then concentrated under vacuum to give 173 mg of a syrup-like substance. The substance was purified by column chromatography (silica gel, developed with dichloromethane-methanol) to give 172.2 mg of N-cyclohexyl-2-hydroxy-2-[2-(1-(N-(3-phenoxybenzoyl)phenylalanyl)pyrrolidinyl)]acetamide as a colorless amorphous solid. Yield, 84.8%.

FAB-MS m/z 570 (M+1)$^+$

Example 28

N-Cyclohexyl-2-oxo-2-[2-(1-(N-(3-phenoxybenzoyl)phenylalanyl)pyrrolidinyl)]acetamide To 155.3 mg of N-cyclohexyl-2-hydroxy-2-[2-(1-(N-(3-phenoxybenzoyl)phenylalanyl)pyrrolidinyl)]acetamide were added 520 μl of acetic anhydride and 0.5 ml of DMSO. The mixture was stirred at room temperature for 24 hours. At the end of the reaction, 15 ml of water was added to the reaction solution followed by stirring for 30 minutes. The resulting aqueous layer was extracted twice with 10 ml each of ethyl acetate. The oily layer was dried over anhydrous sodium sulfate and concentrated under vacuum to give 238 mg of a syrup-like substance. The substance was purified by column chromatography (silica gel, developed with dichloromethane-acetonitrile) to give 125.1 mg of N-cyclohexyl-2-oxo-2-[2-(1-(N-(3-phenoxybenzoyl)phenylalanyl)pyrrolidinyl)]acetamide as a colorless amorphous solid. Yield, 80.8%.

melting point: 73–75° C.

[α]22/D–43.6° (c 1.07, CHCl$_3$)

FAB-MS m/z 568 (M+1)$^+$

1H-NMR (CDCl$_3$) δ:
  1.05–1.50 (5H, m)
  1.52–2.04 (8H, m)
  2.33 (1H, m)
  3.07 (1H, dd, J=6.1, 13.7Hz)
  ca. 3.12 (1H, m, overlapping)
  3.19 (1H, dd, J=7.1, 13.7Hz)
  3.64–3.84 (2H, m)
  5.12 (1H, br ddd)
  5.34 (1H, dd, J=6.3, 8.6Hz)
  6.80 (1H, d, J=8.6Hz)
  6.90–7.50 (15H, m)

Example 29

N-Cyclohexyl-2-hydroxy-2-[2-(1-(N-(3-(3-pyridyl)acryloyl)phenylalanyl)pyrrolidinyl)]acetamide To 132.6 mg of N-cyclohexyl-2-hydroxy-2-[2-(1-phenylalanyl)pyrrolidinyl)]acetamide hydrochloride were added 50.5 mg of trans-3-(3-pyridyl)acrylic acid, 87.4 mg of 1-hydroxybenzotriazole and 2 ml of DMF. Under ice cooling 48 μl of triethylamine and 86.5 mg of 1-ethyl-3-(3-dimethylaminopropyl)carbodiimide hydrochloride were added to the mixture. After stirring for 30 minutes, the mixture was stirred at room temperature for further 21 hours. Thereafter, the reaction solution was diluted with 20 ml of ethyl acetate and the diluted solution was washed successively with 15 ml each of 4% sodium hydrogencarbonate aqueous solution and saturated sodium chloride aqueous solution. The organic layer was dried over anhydrous sodium sulfate and then concentrated under vacuum to give 189 mg of an amorphous solid. The solid was purified by column chromatography (silica gel, developed with dichloromethane-methanol-triethylamine) to give 149.4 mg of N-cyclohexyl-2-hydroxy-2-[2-(1-(N-(3-(3-pyridyl)acryloyl)phenylalanyl)pyrrolidinyl)]acetamide as a colorless amorphous solid. Yield, 91.9%.

FAB-MS m/z 505 (M+1)$^+$

Example 30

N-Cyclohexyl-2-hydroxy-2-[2-(1-(N-(3-(2-furyl)acryloyl)phenylalanyl)pyrrolidinyl)]acetamide To 125.2 mg of N-cyclohexyl-2-hydroxy-2-[2-(1-phenylalanyl)pyrrolidinyl)]acetamide hydrochloride were added 44.3 mg of 3-(2-furyl)acrylic acid, 82.5 mg of 1-hydroxybenzotriazole and 2 ml of DMF. Under ice cooling 45 μl of triethylamine and 82.0 mg of 1-ethyl-3-(3-dimethylaminopropyl)carbodiimide hydrochloride were added to the mixture. After stirring for 2 hours, the mixture was stirred at room temperature for further 7 hours. Thereafter, the reaction solution was diluted with 20 ml of ethyl acetate and the diluted solution was washed successively with 15 ml each of 4% sodium hydrogencarbonate aqueous solution, 10% citric acid aqueous solution and saturated sodium chloride aqueous solution. The organic layer was dried over anhydrous sodium sulfate and then concentrated under vacuum to give 206 mg of an amorphous solid. The solid was purified by column chromatography (silica gel, developed with dichloromethane-methanol) to give 138.8 mg of N-cyclohexyl-2-hydroxy-2-[2-(1-(N-(3-(2-furyl)acryloyl)phenylalanyl)pyrrolidinyl)]acetamide as a colorless amorphous solid. Yield, 92.1%.

FAB-MS m/z 494 (M+1)$^+$

Example 31

N-Cyclohexyl-2-oxo-2-[2-(1-(N-(3-(2-furyl) acryloyl)phenylalanyl)pyrrolidinyl)]acetamide To 138.4 mg of N-cyclohexyl-2-hydroxy-2-[2-(1-(N-(3-(2-furyl)acryloyl)phenylalanyl)pyrrolidinyl)]acetamide were added 0.53 ml of acetic anhydride and 1.0 ml of DMSO. The mixture was stirred at room temperature for 23 hours. At the end of the reaction, 15 ml of water was added to the reaction solution followed by stirring for an hour. The resulting aqueous layer was extracted 3 times with 10 ml each of dichloromethane. The oily layer was dried over anhydrous sodium sulfate and concentrated under vacuum to give an oily substance. The oily substance was purified by column chromatography (silica gel, developed with dichloromethane-acetonitrile-acetic acid). The resulting solid was washed with hexane to give 127.3 mg of N-cyclohexyl-2-oxo-2-[2-(1-(N-(3-(2-furyl)acryloyl) phenylalanyl)pyrrolidinyl)]acetamide as colorless powders. Yield, 92.4%.

melting point: 90–92° C.

[α]26/D–53.1° (c 1.00, CHCl$_3$)

FAB-MS m/z 492 (M+1)$^+$

1H-NMR (CDCl$_3$) δ:
1.02–1.46 (5H, m)
156–2.04 (8H, m)
2.32 (1H, m)
3.03 (1H, dd, J=5.9, 13.7Hz)
ca. 3.06 (1H, m, overlapping)
3.14 (1H, dd, J=7.6, 13.7Hz)
3.68 (1H, m)
3.75 (1H, m)
5.08 (1H, ddd, J=5.9, 7.6, 8.3Hz)
5.33 (1H, dd, J=5.9, 8.8Hz)
6.25 (1H, d, J=15.6Hz)
6.43 (1H, m)
6.45 (1H, d, J=8.3Hz)
6.52 (1H, m)
6.79 (1H, d, J=8.3Hz)
7.20–7.37 (5H, m)
7.33 (1H, d, J=15.6Hz)
7.43 (1H, m)

Example 32

N-Cyclohexyl-2-hydroxy-2-[2-(1-(N-(3-cyclohexylpropionylphenylalanyl)pyrrolidinyl)] acetamide To 129.7 mg of N-cyclohexyl-2-hydroxy-2-[2-(1-phenylalanyl)pyrrolidinyl)]acetamide hydrochloride were added 57 μl of 3-cyclohexylpropionic acid, 85.5 mg of 1-hydroxybenzotriazole and 2 ml of DMF. Under ice cooling 47 μl of triethylamine and 84.9 mg of 1-ethyl-3-(3-dimethylaminopropyl)carbodiimide hydrochloride were added to the mixture. After stirring for 2 hours, the mixture was stirred at room temperature for further 14 hours. Thereafter, the reaction solution was diluted with 20 ml of ethyl acetate and the diluted solution was washed successively with 15 ml each of 4% sodium hydrogencarbonate aqueous solution, 10% citric acid aqueous solution and saturated sodium chloride aqueous solution. The organic layer was dried over anhydrous sodium sulfate and then concentrated under vacuum to give 225 mg of an oily substance. The oily substance was purified by column chromatography (silica gel, developed with dichloromethane-methanol) to give 150.6 mg of N-cyclohexyl-2-hydroxy-2-[2-(1-(N-(3-cyclohexylpropionyl)phenylalanyl) pyrrolidinyl)]acetamide as a colorless amorphous solid. Yield, 93.0%.

FAB-MS m/z 512 (M+1)$^+$

Example 33

N-Cyclohexyl-2-oxo-2-[2-(1-(N-(3-cyclohexylpropionyl)phenylalanyl)pyrrolidinyl)] acetamide To 150.4 mg of N-cyclohexyl-2-hydroxy-2-[2-(1-(N-(3-cyclohexylpropionyl)phenylalanyl)pyrrolidinyl)]acetamide were added 0.56 ml of acetic anhydride and 0.6 ml of DMSO. The mixture was stirred at room temperature for 24 hours. At the end of the reaction, 15 ml of water was added to the reaction solution followed by stirring for an hour. The resulting aqueous layer was extracted 3 times with 10 ml each of dichloromethane. The oily layer was dried over anhydrous sodium sulfate and concentrated under vacuum to give an oily substance. The oily substance was purified by column chromatography (silica gel, developed with dichloromethane-acetonitrile) to give 128.7 mg of N-cyclohexyl-2-oxo-2-[2-(1-(N-(3-cyclohexylpropionyl) phenylalanyl)pyrrolidinyl)]acetamide as a colorless amorphous solid. Yield, 85.9%.

The amorphous solid was crystallized by treating with ethyl acetate-hexane.

melting point: 71–74° C.

[α]28/D–30.0° (c 1.02, CHCl$_3$)

FAB-MS m/z 510 (M+1)$^+$

1H-NMR (CDCl$_3$) δ:
0.77–0.95 (2H, m)
1.05–1.51 (11H, m)
1.55–2.04 (13H, m)
2.12 (2H, t)
2.32 (1H, m)
2.94 (1H, dd, J=6.4, 13.7Hz)
ca. 3.07 (1H, m, overlapping)
3.08 (1H, dd, J=7.3, 13.7Hz)
3.66 (1H, m)
3.75 (1H, m)
4.97 (1H, ddd, J=6.4, 7.3, 7.8Hz)
5.32 (1H, dd, J=5.9, 8.8Hz)
6.18 (1H, d, J=7.8Hz)
6.78 (1H, d, J=8.3Hz)
7.19–7.40 (5H, m)

Example 34

N-Cyclohexyl-2-hydroxy-2-[2-(1-(N-t-butoxycarbonylprolyl)pyrrolidinyl)]acetamide After 178.7 mg of N-cyclohexyl-2-hydroxy-2-(2-pyrrolidinyl)acetamide hydrochloride, 153.7 mg of N-t-butoxycarbonylproline and 184.2 mg of 1-hydroxybenzotriazole were dissolved in 2 ml of DMF, 100 μl of triethylamine and 182.5 mg of 1-ethyl-3-(3-dimethylaminopropyl)carbodiimide hydrochloride were added to the solution under ice cooling. After stirring for 2 hours, the mixture was stirred at room temperature for further 8 hours. Thereafter, the reaction solution was diluted with 20 ml of ethyl acetate and the diluted solution was washed successively with 10 ml each of 4% sodium hydrogencarbonate aqueous solution, 10% citric acid aqueous solution and saturated sodium chloride aqueous solution. The organic layer was dried over anhydrous sodium sulfate and then concentrated under vacuum to give 452 mg of an oily substance. The oily substance was purified by column chromatography (silica gel, developed with dichloromethane-methanol-acetic acid) to give 278.3 mg of N-cyclohexyl-2-hydroxy-2-[2-(1-(N-t-butoxycarbonylprolyl)pyrrolidinyl)]acetamide as a colorless syrup-like substance. Yield, 96.6%.

FAB-MS m/z 424 (M+1)$^+$

Example 35

N-Cyclohexyl-2-hydroxy-2-[2-(1-prolylpyrrolidinyl)]acetamide hydrochloride

To 278.0 mg of N-cyclohexyl-2-hydroxy-2-[2-(1-(N-t-butoxycarbonylprolyl)pyrrolidinyl)]acetamide was added 2 ml of 4 N hydrochloric acid-dioxane solution under ice cooling. After stirring at room temperature for an hour, the solvent was distilled off to give a syrup-like substance. To the substance was added 10 ml of ether. After washing, the substance was taken out by filtration and dried to give 214.4 mg of N-cyclohexyl-2-hydroxy-2-[2-(1-prolylpyrrolidinyl)] acetamide hydrochloride as white powders. Yield, 90.8%.

Example 36

N-Cyclohexyl-2-hydroxy-2-[2-(1-(N-(2-quinolylcarbonyl)prolyl)pyrrolidinyl)]acetamide To 2 ml of DMF were added 125.4 mg of N-cyclohexyl-2-hydroxy-2-[2-(1-prolylpyrrolidinyl)]acetamide hydrochloride, 63.5 mg of quinaldinic acid and 94.4 mg of 1-hydroxybenzotriazole. Under ice cooling, 51 μl of triethylamine and 93.5 mg of 1-ethyl-3-(3-dimethylaminopropyl) carbodiimide hydrochloride were added to the mixture. After stirring for 2 hours, the reaction mixture was stirred at room temperature for further 7 hours. The reaction solution was then diluted with 20 ml of ethyl acetate. The resulting mixture was washed successively with 15 ml each of 4% sodium hydrogencarbonate aqueous solution and saturated sodium chloride aqueous solution. The organic layer was dried over anhydrous sodium sulfate and concentrated under vacuum to give 201.2 mg of an amorphous solid. The solid was purified by column chromatography (silica gel, developed with dichloromethane-methanol-triethylamine) to give 162.0 mg of N-cyclohexyl-2-hydroxy-2-[2-(1-(N-(2-quinolylcarbonyl)prolyl)pyrrolidinyl)]acetamide as a light yellow amorphous solid. Yield, 97.1%.

FAB-MS m/z 479 (M+1)$^+$

Example 37

N-Cycloheptyl-2-hydroxy-2-[2-(1-t-butoxycarbonylpyrrolidinyl)]acetamide

In 7 ml of DMF were dissolved 588.8 mg of 2-hydroxy-2-[2-(1-t-butoxycarbonylpyrrolidinyl)]acetic acid and 487.9 mg of 1-hydroxybenzotriazole. Under ice cooling, 0.36 ml of cycloheptylamine and 575.1 mg of 1-ethyl-3-(3-dimethylaminopropyl)carbodiimide hydrochloride were added to the solution. After stirring for 2 hours, stirring was continued at room temperature for further 5 hours. At the end of the reaction, 70 ml of ethyl acetate was added to the reaction mixture for dilution. The mixture was washed successively with 30 ml each of 4% sodium hydrogencarbonate aqueous solution, saturated sodium chloride aqueous solution, 10% citric acid aqueous solution and saturated sodium chloride aqueous solution. The oily layer was dried over anhydrous sodium sulfate and the solvent was then distilled off to give 860.6 mg of white solid. Next, the solid was purified by column chromatography (Sephadex LH20, developed with methanol) to give 790.0 mg of N-cycloheptyl-2-hydroxy-2-[2-(1-t-butoxycarbonylpyrrolidinyl)]acetamide as a white solid. Yield, 96.7%.

FAB-MS m/z 341 (M+1)$^+$

Example 38

N-Cycloheptyl-2-hydroxy-2-[2-pyrrolidinyl)] acetamide hydrochloride

To 790.0 mg of N-cycloheptyl-2-hydroxy-2-[2-(1-t-butoxycarbonylpyrrolidinyl)]acetamide was added 14 ml of 4 N hydrochloric acid-dioxane solution under ice cooling. After stirring at room temperature for an hour, the solvent was distilled off to give 707.3 mg of white solid. After 20 ml of ether was added to the solid, the mixture was stirred for 30 minutes in a suspended state. The solid was then taken out by filtration and dried to give 622.9 mg of N-cycloheptyl-2-hydroxy-2-(2-pyrrolidinyl)acetamide hydrochloride as a white solid. Yield, 97.0%.

Example 39

N-Cycloheptyl-2-hydroxy-2-[2-(1-(N-t-butoxycarbonylphenylalanyl)pyrrolidinyl)]acetamide In 1 ml of DMF were dissolved 102.4 mg of N-cycloheptyl-2-hydroxy-2-(2-pyrrolidinyl)acetamide hydrochloride, 104.6 mg of N-t-butoxycarbonylphenylalanine and 100.3 mg of 1-hydroxybenzotriazole. Under ice cooling, 55 μl of triethylamine and 99.3 mg of 1-ethyl-3-(3-dimethylaminopropyl) carbodiimide hydrochloride were added to the solution. After stirring for 2 hours, the reaction mixture was stirred at room temperature for further 4 hours. The reaction solution was then diluted with 15 ml of ethyl acetate. The resulting mixture was washed successively with 10 ml each of 4% sodium hydrogencarbonate aqueous solution, 10% citric acid aqueous solution and saturated sodium chloride aqueous solution. The organic layer was dried over anhydrous sodium sulfate and concentrated under vacuum to give 391 mg of an oily substance. The oily substance was purified by column chromatography (silica gel, developed with dichloromethane-methanol) to give 169.5 mg of N-cycloheptyl-2-hydroxy-2-[2-(1-(N-t-butoxycarbonylphenylalanyl)pyrrolidinyl)]acetamide as a colorless amorphous solid. Yield, 94.0%.

FAB-MS m/z 488 (M+1)$^+$

Example 40

N-Cycloheptyl-2-hydroxy-2-[2-(1-(N-(3-phenoxybenzoyl)phenylalanyl)pyrrolidinyl)] acetamide To 169.1 mg of N-cycloheptyl-2-hydroxy-2-[2-(1-(N-t-butoxycarbonylphenylalanyl)pyrrolidinyl)]acetamide was added 2.0 ml of trifluoroacetic acid. After stirring at room temperature for 40 minutes, the solvent was distilled off and 2 ml of toluene was added to the residue followed by distilling off the solvent. This cycle of the procedures was repeated 3 times to give N-cycloheptyl-2-hydroxy-2-[2-(1-phenylalanylpyrrolidinyl)]acetamide trifluoroacetate as an amorphous solid. After 78.0 mg of 3-phenoxybenzoic acid, 93.7 mg of 1-hydroxybenzotriazole and 2 ml of DMF were added to the solid, 58 µl of triethylamine and 93.1 mg of 1-ethyl-3-(3-dimethylaminopropyl)carbodiimide hydrochloride were added to the mixture. After stirring for 2 hours, stirring was continued at room temperature for further 18 hours. Thereafter, the reaction solution was diluted with 20 ml of ethyl acetate and the diluted solution was washed successively with 10 ml each of 4% sodium hydrogencarbonate aqueous solution, 10% citric acid aqueous solution and saturated sodium chloride aqueous solution. The organic layer was dried over anhydrous sodium sulfate and then concentrated under vacuum to give an amorphous solid. The solid was purified by column chromatography (silica gel, developed with dichloromethane-methanol) to give 176.2 mg of N-cycloheptyl-2-hydroxy-2-[2-(1-(N-(3-phenoxybenzoyl)phenylalanyl)pyrrolidinyl)]acetamide as a colorless amorphous solid. Yield, 87.0%.

FAB-MS m/z 584 (M+1)+

Example 41

N-Cycloheptyl-2-oxo-2-[2-(1-(N-(3-phenoxybenzoyl)phenylalanyl)pyrrolidinyl)] acetamide To 175.9 mg of N-cycloheptyl-2-hydroxy-2-[2-(1-(N-(3-phenoxybenzoyl)phenylalanyl)pyrrolidinyl)]acetamide were added 0.57 ml of acetic anhydride and 1.0 ml of DMSO. The mixture was stirred at room temperature for 28 hours. At the end of the reaction, 20 ml of water was added to the reaction solution followed by stirring for 30 minutes. The resulting aqueous layer was extracted 3 times with 10 ml each of dichloromethane. The oily layer was dried over anhydrous sodium sulfate and concentrated under vacuum to give an oily substance. The oily substance was purified by column chromatography (silica gel, developed with dichloromethane-acetonitrile) to give 144.9 mg of N-cycloheptyl-2-oxo-2-[2-(1-(N-(3-phenoxybenzoyl) phenylalanyl)pyrrolidinyl)]acetamide as a colorless amorphous solid. Yield, 82.7%.

melting point: 70–72° C.
[α]24/D –45.0° (c 1.03, CHCl$_3$)
FAB-MS m/z 582 (M+1)+
1H-NMR (CDCl$_3$) δ:
  1.40–1.74 (11H, m)
  1.80–2.06 (4H, m)
  2.32 (1H, m)
  3.07 (1H, dd, J=5.9, 13.7Hz)
  ca. 3.12 (1H, m, overlapping)
  3.18 (1H, dd, J=7.3, 13.7Hz)
  3.70 (1H, m)
  3.92 (1H, m)
  5.11 (1H, ddd, J=5.9, 7.3, 7.6Hz)
  5.33 (1H, dd, J=5.9, 8.8Hz)
  6.84 (1H, d, J=8.3Hz)
  6.93 (1H, brd)
  6.99 (2H, m)
  7.12 (2H, m)
  7.18–7.44 (10H, m)

Example 42

N-Cyclohexyl-2-hydroxy-2-[2- (1-(N-benzoylphenylalanyl)pyrrolidinyl)]acetamide

To 138.9 mg of N-cyclohexyl-2-hydroxy-2-[2-(1-phenylalanyl)pyrrolidinyl)]acetamide hydrochloride were added 1.4 ml of dry tetrahydrofuran and 105 µl of triethylamine. A solution of 44 µl of benzoyl chloride in 3 ml of dry tetrahydrofuran was then dropwise added to the mixture over 30 minutes. After completion of the dropwise addition, the mixture was stirred for 3 hours and the solvent was distilled off under vacuum. After 6 ml of 1 N hydrochloric acid was added to the solid obtained, the mixture was extracted once with 8 ml of ethyl acetate and twice with 4 ml of ethyl acetate. The oily layers were combined and washed successively with 12 ml each of saturated sodium hydrogencarbonate aqueous solution and saturated sodium chloride aqueous solution. The oily layer was dried over anhydrous sodium sulfate and concentrated under vacuum to give 176 mg of an amorphous solid. The solid was purified by column chromatography (silica gel, developed with dichloromethane-methanol) to give 150.1 mg of N-cyclohexyl-2-hydroxy-2-[2-(1-(N-benzoylphenylalanyl) pyrrolidinyl)]acetamide as a colorless amorphous solid. Yield, 92.8%.

FAB-MS m/z 478 (M+1)+

Example 43

N-Cyclohexyl-2-oxo-2-[2-(1-(N-benzoylphenylalanyl)pyrrolidinyl)]acetamide

To 150.1 mg of N-cyclohexyl-2-hydroxy-2-[2-(1-(N-benzoylphenylalanyl)pyrrolidinyl)]acetamide were added 0.60 ml of acetic anhydride and 1.5 ml of DMSO. The mixture was stirred at room temperature for 24 hours. At the end of the reaction, 25 ml of water was added to the reaction solution followed by stirring for 1.5 hour. The resulting aqueous layer was extracted 3 times with 10 ml each of dichloromethane. The oily layer was dried over anhydrous sodium sulfate and concentrated under vacuum to give an oily substance. The oily substance was purified by column chromatography (silica gel, developed with dichloromethaneacetonitrile) to give 132.3 mg of N-cyclohexyl-2-oxo-2-[2- (1-(N-benzoylphenylalanyl) pyrrolidinyl)]acetamide as a colorless amorphous solid. Yield, 88.5%..

melting point: 78–80° C.
[α]26/D–47.6° (c 1.03, CHCl$_3$)
FAB-MS m/z 476 (M+1)+
1H-NMR (CDCl$_3$) δ:
  1.11–1.48 (5H, m)
  1.55–2.06 (8H, m)
  2.34 (1H, m)
  3.10 (1H, dd, J=5.9, 13.7Hz)
  ca. 3.13 (1H, m)
  3.21 (1H, dd, J=7.3, 13.7Hz)
  3.65–3.83 (2H, m)
  5.16 (1H, ddd, J=5.9, 7.3, 7.8Hz)
  5.35 81H, dd, J=6.1, 8.5Hz)
  6.80 (1H, d, J=8.3Hz)
  6.97 (1H, d, J=7.8Hz)
  7.19–7.55 (8H, m)
  7.69 (2H, m)

Example 44

N-Cyclohexyl-2-hydroxy-2-[2-(1-(N-benzyloxycarbonylphenylalanyl)pyrrolidinyl)] acetamide In 2 ml of DMF were dissolved 81.7 mg of N-cyclohexyl-2-hydroxy-2-(2-pyrrolidinyl)acetamide hydrochloride, 102.2 mg of benzyloxycarbonylphenylalanine and 47.8 mg of 1-hydroxybenzotriazole. Under ice cooling, 48 μl of triethylamine and 66.5 mg of 1-ethyl-3-(3-dimethylaminopropyl)carbodiimide hydrochloride were added to the solution. After stirring for 2 hours, the reaction mixture was stirred at room temperature for further 18 hours. The reaction solution was then diluted with 40 ml of ethyl acetate. The resulting mixture was washed successively with 30 ml each of 10% citric acid aqueous solution, 4% sodium hydrogencarbonate aqueous solution, distilled water and saturated sodium chloride aqueous solution. The organic layer was dried over anhydrous sodium sulfate and concentrated under vacuum to give 153.4 mg of an oily substance. The oily substance was purified by column chromatography (silica gel, developed with dichloromethane-methanol) to give 148 mg of N-cyclohexyl-2-hydroxy-2-[2-(1-(N-benzyloxycarbonylphenylalanyl)prolyl)pyrrolidinyl)] acetamide as a colorless amorphous solid.

FAB-MS m/z 508 (M+1)+

Example 45

N-Cyclohexyl-2-oxo-2-[2-(1-(N-benzyloxycarbonylphenylalanyl)pyrrolidinyl)] acetamide After 45.8 mg of N-cyclohexyl-2-hydroxy-2-[2-(1-(N-benzyloxycarbonylphenylalanyl)pyrrolidinyl)]acetamide hydrochloride, 45.8 mg of pyridinetrifluoroacetate and 191.3 mg of 1-ethyl-3-(3-dimethylaminopropyl)carbodiimide hydrochloride were dissolved in a mixture of 1.5 ml of DMSO and 3 ml of benzene, the solution was stirred at room temperature for 20 hours. At the end of the reaction, the reaction solution was diluted with 50 ml of ethyl acetate. The resulting mixture was washed successively with 30 ml each of 10% citric acid aqueous solution, 4% sodium hydrogencarbonate aqueous solution, distilled water and saturated sodium chloride aqueous solution. The organic layer was dried over anhydrous sodium sulfate and concentrated under vacuum to give 147.4 mg of an oily substance. The oily substance was purified by column chromatography (silica gel, developed with dichloromethane) to give 127.6 mg of N-cyclohexyl-2-oxo-2-[2-(1-(N-benzyloxycarbonylphenylalanyl)pyrrolidinyl)]acetamide as a colorless glassy solid.

FAB-MS m/z 506 (M+1)+

Example 46

N-Cyclohexyl-2-hydroxy-2-[2-(1-(N-(phenylthioacetyl)phenylalanyl)pyrrolidinyl)] acetamide In 1 ml of DMF were dissolved 101.6 mg of N-cyclohexyl-2-hydroxy-2-[2-(1-(N-phenylalanylpyrrolidinyl)]acetamide hydrochloride, 36.7 mg of phenylthioacetic acid and 49.4 mg of 1-hydroxybenzotriazole. Under ice cooling, 57.7 mg of 1-ethyl-3-(3-dimethylaminopropyl)carbodiimide hydrochloride was added to the solution. After stirring for 2 hours, the reaction mixture was stirred at room temperature for further 22 hours. After 10% citric acid was added to the reaction solution, the resulting mixture was extracted twice with ethyl acetate and washed successively with 10% citric acid aqueous solution, 4% sodium hydrogencarbonate aqueous solution, distilled water and saturated sodium chloride aqueous solution. The organic layer was dried over anhydrous sodium sulfate and concentrated under vacuum to give 125.1 mg of the title compound as an oily substance.

FAB-MS m/z 524 (M+1)+

Example 47

N-Cyclohexyl-2-oxo-2-[2-(1-(N-(phenylthioacetyl)phenylalanyl)pyrrolidinyl)]acetamide To 125 mg of N-cyclohexyl-2-hydroxy-2-[2-(1-(N-(phenylthioacetyl)phenylalanyl)pyrrolidinyl)]acetamide were added 0.45 ml of acetic anhydride and 0.5 ml of DMSO. The mixture was stirred at room temperature for 18 hours. At the end of the reaction, 1 ml of water was added to the reaction solution followed by stirring for 30 minutes. After 3 ml of methanol was added to the reaction mixture. The mixture was purified on a Sephadex LH20 column (300 ml, filled up with methanol). The product was then dissolved in ethyl acetate. After washing with water and then with saturated sodium chloride aqueous solution, the solution was dried over anhydrous sodium sulfate and concentrated under vacuum to give 108 mg of N-cyclohexyl-2-oxo-2-[2-(1-(N-(phenylthioacetyl)phenylalanyl)pyrrolidinyl)]acetamide as a colorless amorphous solid.

FAB-MS m/z 522 (M+1)+

1H-NMR (CDCl$_3$) δ:
1.05–1.50 (5H, m)
1.54–2.05 (8H, m)
2.32 (1H, m)
2.91 (1H, dd, J=6.9, 13.9Hz)
3.00–3.20 (2H, m)
3.55–3.85 (2H, m)
4.70 (1H, ddd, J=6.9, 7.1, 8.9Hz)
5.03, 5.06 (2H, ABq, J=12.4Hz)
5.32 (1H, dd, J=5.4, 8.1Hz)
5.50 (1H, d, J=8.9Hz)
6.78 (1H, d, J=8.2Hz)
7.10–7.46 (10H, m)

Example 48

N-Cyclohexyl-2-hydroxy-2-[2-(1-(N-(isonicotinonyl)phenylalanyl)pyrrolidinyl)] acetamide In 2 ml of DMF were dissolved 100.1 mg of N-cyclohexyl-2-hydroxy-2-[2-(1-(N-phenylalanylpyrrolidinyl)]acetamide hydrochloride, 36.7 mg of isonicotinic acid and 49.4 mg of 1-hydroxybenzotriazole. Under ice cooling, 57.7 mg of 1-ethyl-3-(3-dimethylaminopropyl)carbodiimide hydrochloride was added to the solution. After stirring for 2 hours, the reaction mixture was stirred at room temperature for further 23 hours. After 10% citric acid was added to the reaction solution, the resulting mixture was extracted with ethyl acetate and washed successively twice with 4% sodium hydrogencarbonate aqueous solution and twice with saturated sodium chloride aqueous solution. The organic layer was dried over anhydrous sodium sulfate and concentrated under vacuum to give 101.0 mg of the title compound as an oily substance.

FAB-MS m/z 479 (M+1)+

Example 49

N-Cyclohexyl-2-oxo-2-[2-(1-(N-(isonicotinonyl)phenylalanyl)pyrrolidinyl)]acetamide To 96 mg of N-cyclohexyl-2-hydroxy-2-[2-(1-(N-(isonicotinonyl)phenylalanyl)pyrrolidinyl)]acetamide were added 0.38 ml of acetic anhydride and 1 ml of DMSO. The mixture was stirred at room temperature for 16 hours. At the end of the reaction, 1 ml of water was added to the reaction solution followed by stirring for 30 minutes. After 4% sodium hydrogencarbonate aqueous solution was added to the reaction mixture, the mixture was extracted twice with ethyl acetate. The organic layer was washed successively with 4% sodium hydrogencarbonate aqueous solution and saturated sodium chloride aqueous solution. The organic layer was dried over anhydrous sodium sulfate and concentrated under vacuum to give 92.4 mg of N-cyclohexyl-2-oxo-2-[2-(1-(N-(isonicotinonyl)phenylalanyl)pyrrolidinyl)] acetamide as a colorless amorphous solid.

FAB-MS m/z 477 (M+1)$^+$
1H=NMR (CDCl$_3$) δ:
 1.15–1.45 (5H, m)
 1.60–2.5 (8H, m)
 2.35 (1H, m)
 3.05–3.3 (3H, m)
 3.5–3.8 (2H, m)
 5.12 (1H, dd J=7.8, 13.2Hz)
 5.38 (1H, dd J=5.9, 8.8Hz)
 6.79 (1H, d J=8.3)
 7.1–7.35 (6H, m)
 7.50 (2H, dd J=1.7, 4.6Hz)
 8.68 (2H, dd J=1.7, 4.6Hz)

Example 50

N-Cyclohexyl-2-hydroxy-2-[2-(1-(N-(4-pyridylthioacetyl)phenylalanyl)pyrrolidinyl)] acetamide In 1 ml of DMF were dissolved 120.9 mg of N-cyclohexyl-2-hydroxy-2-[2-(1-(N-phenylalanylpyrrolidinyl)]acetamide hydrochloride, 60.0 mg of 4-pyridylthioacetic acid and 60.3 mg of 1-hydroxybenzotriazole. Under ice cooling, 68.0 mg of 1-ethyl-3-(3-dimethylaminopropyl)carbodiimide hydrochloride was added to the solution. After stirring for 2 hours, the reaction mixture was stirred at room temperature for further 17 hours. After 4% sodium hydrogencarbonate aqueous solution was added to the reaction solution, the resulting mixture was extracted twice with ethyl acetate and washed successively with 4% sodium hydrogencarbonate aqueous solution, distilled water and saturated sodium chloride aqueous solution. The organic layer was dried over anhydrous sodium sulfate and concentrated under vacuum to give 146 mg of N-cyclohexyl-2-hydroxy-2-[2-(1-(N-(4-pyridylthioacetyl)phenylalanyl)pyrrolidinyl)]acetamide as a colorless amorphous solid.

FAB-MS m/z 525 (M+1)$^+$

Example 51

N-Cyclohexyl-2-oxo-2-[2-(1-(N-(4-pyridylthioacetyl)phenylalanyl)pyrrolidinyl)] acetamide To 139.5 mg of N-cyclohexyl-2-hydroxy-2-[2-(1-(N-(4-pyridylthioacetyl)phenylalanyl)pyrrolidinyl)]acetamide were added 0.6 ml of acetic anhydride and 1 ml of DMSO. The mixture was stirred at room temperature for 19 hours. At the end of the reaction, 1 ml of water was added to the reaction solution followed by stirring for 30 minutes. After 4% sodium hydrogencarbonate aqueous solution was added to the reaction mixture, the mixture was extracted twice with ethyl acetate. The organic layer was washed successively with 4% sodium hydrogencarbonate aqueous solution and saturated sodium chloride aqueous solution. The organic layer was dried over anhydrous sodium sulfate and concentrated under vacuum. The residue was dissolved in methylene chloride. The solution was purified by column chromatography (silica gel, developed with dichloromethane-methanol) to give 88.7 mg of N-cyclohexyl-2-oxo-2-[2-(1-(N-(4-pyridylthioacetyl)phenylalanyl)pyrrolidinyl)] acetamide as a colorless amorphous solid.

FAB-MS m/z 523 (M+1)$^+$
1H-NMR (CDCl$_3$) δ:
 1.15–1.45 (5H, m)
 1.60–2.0 (8H, m)
 2.35 (1H, m)
 2.85 (1H, dd J=7.1, 13.9Hz)
 3.06 (1H, dd J=6.6, 13.9Hz)
 3.2 (1H, m)
 3.5–3.8 (4H, m)
 4.94 (1H, dd J=6.8, 14.7Hz)
 5.62 (1H, dd J=5.6, 9.0Hz)
 6.76 81H, d J=8.3)
 7.0 (2H, dd J=1.6, 4.8Hz)
 7.05–7.25 (5H, m)
 8.37 (2H dd J=1.6, 4.8Hz)

Example 52

N-Cyclohexyl-2-hydroxy-2-[2-(1-(N-(nicotinonyl) phenylalanyl)pyrrolidinyl)]acetamide In 1 ml of DMF were dissolved 131.2 mg of N-cyclohexyl-2-hydroxy-2-[2-(1-(N-phenylalanylpyrrolidinyl)]acetamide hydrochloride, 36.7 mg of nicotinic acid and 48.5 mg of 1-hydroxybenzotriazole. Under ice cooling, 74.3 mg of 1-ethyl-3-(3-dimethylaminopropyl)carbodiimide hydrochloride was added to the solution. After stirring for 2 hours, the reaction mixture was stirred at room temperature for further 14 hours. After 4% sodium hydrogencarbonate aqueous solution was added to the reaction solution, the resulting mixture was extracted twice with ethyl acetate. The extract was washed successively with 4% sodium hydrogencarbonate aqueous solution, twice with distilled water and twice with saturated sodium chloride aqueous solution. The organic layer was dried over anhydrous sodium sulfate and concentrated under vacuum to give 147 mg of the title compound as a colorless amorphous solid.

FAB-MS m/z 479 (M+1)$^+$

Example 53

N-Cyclohexyl-2-oxo-2-[2-(1-(N-(nicotinonyl) phenylalanyl)pyrrolidinyl)]acetamide To 141 mg of N-cyclohexyl-2-hydroxy-2-[2-(1-(N-(nicotinonyl)phenylalanyl)pyrrolidinyl)]acetamide --were added 0.6 ml of acetic anhydride and 1 ml of DMSO. The mixture was stirred at room temperature for 19 hours. At the end of the reaction, 1 ml of water was added to the reaction solution followed by stirring for 30 minutes. After 4% sodium hydrogencarbonate aqueous solution was added to the reaction mixture, the mixture was extracted twice with ethyl acetate. The organic layer was washed successively with 4% sodium hydrogencarbonate aqueous solution and saturated sodium chloride aqueous solution. The organic layer was dried over anhydrous sodium sulfate and concentrated under vacuum to give 149.6 mg of a colorless amorphous solid. The solid was dissolved in methylene chloride. The resulting solution was purified by column chromatography (silica gel, developed with dichloromethanemethanol) to give 113 mg of N-cyclohexyl-2-oxo-2-[2-(1-(N-(nicotinonyl)phenylalanyl)pyrrolidinyl)]acetamide as a colorless amorphous solid.

FAB-MS m/z 477 (M+1)+
1H-NMR (CDCl$_3$) δ:
1.15–1.45 (5H, m)
1.60–2.05 (8H, m)
2.35 (1H, m)
2.95–3.3 (3H, m)
3.75 (2H, m)
5.15 (1H, dd J=7.3, 14Hz)
5.37 (1H, dd J=5.9, 8.8Hz)
6.8 (1H, d J=8.3)
7.13 (1H, d J=8.3)
7.2–7.4 (6H, m)
8.0 (1H, dt J=2.7, 8Hz)
8.7 (1H, dd J=1.4, 4.6Hz)
8.9 (1H, d J=2.5Hz)

Example 54

N-Cyclohexyl-2-hydroxy-2-[2-(1-(N-(4-pyridylthioacetyl)prolyl)pyrrolidinyl)]acetamide In 2 ml of DMF were dissolved 111 mg of N-cyclohexyl-2-hydroxy-2-[2-(1-(N-prolylpyrrolidinyl)]acetamide hydrochloride, 63.5 mg of 4-pyridylthioacetic acid and 62.5 mg of 1-hydroxybenzotriazole. Under ice cooling, 73.1 mg of 1-ethyl-3-(3-dimethylaminopropyl)carbodiimide hydrochloride was added to the solution. After stirring for 2 hours, the reaction mixture was stirred at room temperature for further 14 hours. After 4% sodium hydrogencarbonate aqueous solution was added to the reaction solution, the resulting mixture was extracted twice with ethyl acetate and washed successively with 4% sodium hydrogencarbonate aqueous solution, distilled water and saturated sodium chloride aqueous solution. The organic layer was dried over anhydrous sodium sulfate and concentrated under vacuum. The residue was dissolved in methylene chloride. The solution was purified by column chromatography (silica gel, developed with dichloromethane-methanol) to give 106.1 mg of N-cyclohexyl-2-hydroxy-2-[2-(1-(N-(4-pyridylthioacetyl)prolyl)pyrrolidinyl)]acetamide as a colorless amorphous solid.

FAB-MS m/z 475 (M+1)+

Example 55

N-Cyclohexyl-2-oxo-2-[2-(1-(N-(4-pyridylthioacetyl)prolyl)pyrrolidinyl)]acetamide To 100.9 mg of N-cyclohexyl-2-hydroxy-2-[2-(1-(N-(4-pyridylthioacetyl)prolyl)pyrrolidinyl)]acetamide were added 0.6 ml of acetic anhydride and 1 ml of DMSO. The mixture was stirred at room temperature for 19 hours. At the end of the reaction, 4% sodium hydrogencarbonate aqueous solution was added to the reaction mixture followed by stirring for 20 minutes. The reaction mixture was extracted twice with ethyl acetate. The extract was washed successively with 4% sodium hydrogencarbonate aqueous solution and saturated sodium chloride aqueous solution. The organic layer was dried over anhydrous sodium sulfate and concentrated under vacuum. The residue was dissolved in methylene chloride. The solution was purified by column chromatography (silica gel, developed with dichloromethane-methanol) to give 80.5 mg of N-cyclohexyl-2-oxo-2-[2-(1-(N-(4-pyridylthioacetyl)prolyl)pyrrolidinyl)]acetamide as a colorless amorphous solid.

FAB-MS m/z 473 (M+1)+
1H-NMR (CDCl$_3$) δ:
1.1–1.45 (5H, m)
1.6–2.4 (13H, m)
3.55–3.95 (6H, m)
4.72 (1H, dd J=3.4, 7.8Hz)
5.22 (1H, dd J=5.9, 8.8Hz)
6.75 (1H, d J=8.3)
7.22 (2H, dd J=1.7, 4.6Hz)
8.40 (2H, dd J=1.7, 4.6Hz)

Example 56

N-Cyclohexyl-2-hydroxy-2-[2-(1-(N-(4-morpholinomethylbenzoyl)phenylalanyl)pyrrolidinyl)]acetamide In 1 ml of DMF were dissolved 109.7 mg of N-cyclohexyl-2-hydroxy-2-[2-(1-(N-phenylalanylpyrrolidinyl)]acetamide hydrochloride, 86 mg of 4-morpholinomethylbenzoic acid hydrochloride and 43.1 mg of 1-hydroxybenzotriazole. Under ice cooling, 143.5 mg of Bop reagent and 127 μl of triethylamine were added to the solution. The mixture was stirred at room temperature for 17 hours. After 4% sodium hydrogencarbonate aqueous solution was added to the reaction solution, the resulting mixture was extracted twice with ethyl acetate. The extract was washed successively with 4% sodium hydrogencarbonate aqueous solution and saturated sodium chloride aqueous solution. The organic layer was dried over anhydrous sodium sulfate and concentrated under vacuum to give 169.7 mg of the title compound as a colorless amorphous solid.

FAB-MS m/z 575 (M+1)+

Example 57

N-Cyclohexyl-2-oxo-2-[2-(1-(N-(4-morpholinomethylbenzoyl)phenylalanyl)pyrrolidinyl)]acetamide To 157 mg of N-cyclohexyl-2-hydroxy-2-[2-(1-(N-(4-morpholinomethylbenzoyl)phenylalanyl)pyrrolidinyl)]acetamide were added 0.6 ml of acetic anhydride and 1 ml of DMSO. The mixture was stirred at room temperature for 13 hours. At the end of the reaction, 4% sodium hydrogencarbonate aqueous solution was added to the reaction mixture followed by extraction twice with ethyl acetate. The organic layer was washed successively with 4% sodium hydrogencarbonate aqueous solution and saturated sodium chloride aqueous solution. The organic layer was dried over anhydrous sodium sulfate and concentrated under vacuum. The residue was dissolved in methylene chloride. The solution was purified by column chromatography (silica gel, developed with dichloromethane-methanol) to give 37.4 mg of a solid. The solid was dissolved in a small volume of ethyl acetate and a small excess of HCl-ethyl acetate solution was added thereto. The mixture was evaporated to dryness to give N-cyclohexyl-2-oxo-2-[2-(1- (N-(4-morpholinomethylbenzoyl)phenylalanyl)pyrrolidinyl)] acetamide hydrochloride as a colorless amorphous solid.

FAB-MS m/z 573 (M+1)+

Example 58

N-Cyclohexyl-2-hydroxy-2-[2-(1-(N-(benzylalycyl)pyrrolidinyl)]acetamide

In 5 ml of DMF were dissolved 299.1 mg of N-cyclohexyl-2-hydroxy-2-(2-pyrrolidinyl)acetamide hydrochloride, 187.1 mg of bromoacetic acid and 228.1 mg of 1-hydroxybenzotriazole. Under ice cooling, 191.2 μl of triethylamine and 261.9 mg of 1-ethyl-3-(3-dimethylaminopropyl)carbodiimide hydrochloride were added to the solution. The mixture was stirred for 2 hours and then for 13 hours at room temperature. Then the reaction mixture was diluted with 30 ml of 4% sodium hydrogencarbonate aqueous solution. The diluted solution was extracted twice with ethyl acetate. The extract was washed successively with 4% sodium hydrogencarbonate aqueous solution, 10% citric acid aqueous solution and saturated sodium chloride aqueous solution. The organic layer was dried over anhydrous sodium sulfate and concentrated under vacuum to give 272.1 mg of a colorless amorphous solid. Mass spectrum of the solid revealed that it was a mixture of the N-bromoacetyl compound and the N-chloroacetyl compound. The solid substance was thus employed in the following step without purification. After 100.4 mg of the solid substance was dissolved in 0.3 ml of DMSO, 100 μl of benzylamine was added to the solution. The mixture was stirred at room temperature for 2 hours and 10 minutes. After 2.5 ml of water was added to the reaction solution, the mixture was adsorbed to a small column packed with dry ext (Extrelut®, MERCK). The column was extracted with ethyl acetate. The extract was concentrated and the residue was dissolved in methylene chloride. The solution was passed through a small column packed with dry ext, to which 2.5 ml of 4% sodium hydrogencarbonate aqueous solution was adsorbed. The eluate was fractionated and analyzed by TLC to give hydroxy-2-[2-(1-(N-benzylglycyl)pyrrolidinyl)]acetamide, as a colorless amorphous solid, which contained no benzylamine.

FAB-MS m/z 372 (M+1)$^+$

Example 59

N-Cyclohexyl-2-hydroxy-2-[2-(1-(N-isonicotinonyl-N-benzylglycyl)pyrrolidinyl)]acetamide In 2 ml of DMF were dissolved 107.4 mg of N-cyclohexyl-2-hydroxy-2-[2-(1-(N-benzylglycyl)pyrrolidinyl)]acetamide hydrochloride, 73.8 mg of isonicotinic acid and 100.5 mg of 1-hydroxybenzotriazole. Under ice cooling, 113.8 mg of 1-ethyl-3-(3-dimethylaminopropyl)carbodiimide hydrochloride was added to the solution. After stirring for 2 hours, the reaction mixture was stirred at room temperature for further 13 hours. The reaction solution was diluted with 4% sodium hydrogencarbonate aqueous solution. The resulting mixture was extracted twice with ethyl acetate and the extract was washed successively with 4% sodium hydrogencarbonate aqueous solution, distilled water and saturated sodium chloride aqueous solution. The organic layer was dried over anhydrous sodium sulfate and concentrated under vacuum. The residue was purified by column chromatography (silica gel, developed with dichloromethane-methanol) to give 125.8 mg of N-cyclohexyl-2-hydroxy-2-[2-(1-(N-isonicotinonyl-N-benzylglycyl)pyrrolidinyl)]acetamide as a colorless amorphous solid.

FAB-MS m/z 479 (M+1)$^+$

Example 60

N-Cyclohexyl-2-oxo-2-[2-(1-(N-isonicotinonyl-N-benzylalycyl)pyrrolidinyl)]acetamide To 114.7 mg of N-cyclohexyl-2-hydroxy-2-[2-(1-(N-isonicotinonyl-N-benzylglycyl)pyrrolidinyl)]acetamide were added 0.6 ml of acetic anhydride and 1 ml of DMSO. The mixture was stirred at room temperature for 14.5 hours. At the end of the reaction, 20 ml of 4% sodium hydrogencarbonate aqueous solution was added to the reaction mixture followed by stirring for 30 minutes. The reaction mixture was extracted twice with ethyl acetate. The organic layer was washed successively with 4% sodium hydrogencarbonate aqueous solution, distilled water and saturated sodium chloride aqueous solution. The organic layer was dried over anhydrous sodium sulfate and concentrated under vacuum. The residue was dissolved in methylene chloride and the solution was purified by column chromatography (silica gel, developed with dichloromethane-methanol) to give 89 mg of a colorless amorphous solid. The solid was again purified by column chromatography (silica gel, developed with ethyl acetate) to give 19.7 mg of the product as a colorless amorphous solid.

FAB-MS m/z 477 (M+1)$^+$

Reference Example 3

Benzylmethylamino-N-succinimidyl carbamate

In 100 ml of acetonitrile was dissolved 2571 mg of N,N'-disuccinimide carbonate (DSC). While stirring, 200 ml of acetonitrile solution of 645.2 mg of N-methylbenzylamine was dropwise added to the solution at room temperature over 8 hours. After completion of the dropwise addition, the mixture was stirred at room temperature for further 14 hours. The solvent was distilled off under vacuum and the residue was dissolved in chloroform. Insoluble DSC was removed by filtration. The filtrate was washed successively with water, 1 N hydrochloric acid, 4% sodium hydrogencarbonate aqueous solution and saturated sodium chloride aqueous solution and then dried over anhydrous sodium sulfate. After the solvent was distilled off, the residue was dissolved in methylene chloride. The a solution was purified by column chromatography (silica gel, developed with dichloromethane-acetonitrile) to give 845.2 mg of benzylmethylamino-N-succinimidyl carbamate as a colorless amorphous solid.

FAB-MS m/z 263 (M+1)$^+$
$^1$H-NMR (CDCl$_3$) δ:
  2.84 (4H, s)
  2.91, 3.01 (3H, s), split due to cis- and trans-isomers of the carbamate
  4.51, 4.61 (2H, s), split due to cis- and trans-isomers of the carbamate
  7.26–7.45 (5H, m)

Example 61

N-Cyclohexyl-2-hydroxy-2-[2-(1-(N-(N-benzyl-N-methylcarbamoyl)phenylalanyl)pyrrolidinyl)]acetamide In 2 ml of DMF were dissolved 119.5 mg of N-cyclohexyl-2-hydroxy-2-(2-pyrrolidinyl)acetamide hydrochloride and 118.7 mg of benzylmethylamino-N-succinimidyl carbamate. After 44.9 μl of triethylamine was added to the solution, the mixture was stirred at room temperature for 8 days. The reaction solution was purified on a Sephadex LH20 column (300 ml, filled up with methanol). The purified fraction was dissolved in chloroform. The solution was washed successively with 1 N hydrochloric acid, water and saturated sodium chloride aqueous solution. After drying over anhydrous sodium sulfate, the solution was concentrated under vacuum to give 91.7 mg of N-cyclohexyl-2-hydroxy-2-[2-(1-(N-(N-benzyl-N-methylcarbamoyl)phenylalanyl)pyrrolidinyl)]acetamide as a colorless amorphous solid.

FAB-MS m/z 521 (M+1)⁺

Example 62

N-Cyclohexyl-2-oxo-2-[2-(1-(N-(N-benzyl-N-methylcarbamoyl)phenylalanyl)pyrrolidinyl)]acetamide To 87.1 mg of N-cyclohexyl-2-hydroxy-2-[2-( 1-(N-(N-benzyl-N-methylcarbamoyl)phenylalanyl)pyrrolidinyl)]acetamide were added 0.6 ml of acetic anhydride and 1 ml of DMSO. The mixture was stirred at room temperature for 16 hours. At the end of the reaction, ml of 4% sodium hydrogencarbonate aqueous solution (1 ml) was added to the reaction mixture followed by stirring. The reaction mixture was extracted twice with ethyl acetate. The organic layer was washed successively with 4% sodium hydrogencarbonate aqueous solution, distilled water and saturated sodium chloride aqueous solution. The organic layer was dried over anhydrous sodium sulfate and concentrated under vacuum. The residue was dissolved in methylene chloride and the solution was purified by column chromatography (silica gel, developed with dichloromethane-methanol) to give 85.5 mg of N-cyclohexyl-2-oxo-2-[2-(1-(N-(N-benzyl-N-methylcarbamoyl)phenylalanyl)pyrrolidinyl)]acetamide as a colorless amorphous solid.

FAB-MS m/z 519 (M+1)⁺

Example 63

N-Cyclohexyl-2-hydroxy-2-[2-(1-(2-naphthoyl)pyrrolidinyl)]acetamide

To 150.2 mg of N-cyclohexyl-2-hydroxy-2-(2-pyrrolidinyl)acetamide hydrochloride were added 103.2 mg of 2-naphthoenic acid, 154.3 mg of 1-hydroxybenzotriazole and 2 ml of DMF. Under ice cooling 112 μl of triethylamine and 153.2 mg of 1-ethyl-3-(3-dimethylaminopropyl) carbodiimide hydrochloride were added to the solution. After stirring for 30 minutes, stirring was continued at room temperature for further 3 hours. Thereafter, the reaction solution was diluted with 20 ml of ethyl acetate and the diluted solution was washed successively with 10 ml each of 4% sodium hydrogencarbonate aqueous solution, 1% citric acid aqueous solution and saturated sodium chloride aqueous solution. The organic layer was dried over anhydrous sodium sulfate and then concentrated under vacuum to give 272 mg of a syrup-like substance. The substance was purified by column chromatography (silica gel, developed with dichloromethane-methanol) to give 213.9 mg of the title compound as a colorless amorphous solid. Yield, 98.4%.

FAB-MS m/z 381 (M+1)⁺

Example 64

N-Cyclohexyl-2-oxo-2-[2-(1-(2-naphthoyl)pyrrolidinyl)]acetamide

To 213.7 mg of N-cyclohexyl-2-hydroxy-2-[2-(1-(2-naphthoyl)pyrrolidinyl)]acetamide were added 0.82 ml of acetic anhydride and 0.8 ml of DMSO. The mixture was stirred at room temperature for 22 hours. At the end of the reaction, 20 ml of water was added to the reaction solution followed by stirring for 40 minutes. The aqueous layer was extracted 3 times with 10 ml each of ethyl acetate. The oily layer was dried over anhydrous sodium sulfate and concentrated under vacuum to give a partially crystalline solid. The solid was purified by column chromatography (silica gel, developed with dichloromethane-acetonitrile) to give 160.8 mg of the title compound as a colorless needles. Yield, 97.7%.

melting point: 132.5–133.5° C.
[α]27/D–31.4° (c 1.06, CHCl₃)
FAB-MS m/z 379 (M+1)⁺
1H-NMR (CDCl₃) δ:
  1.00–1.85 (8H, m)
  1.85–2.15 (5H, m)
  2.49 (1H, m)
  3.57–3.95 (3H, m)
  5.48 (1H, dd, J=6.3, 8.3Hz)
  6.82 (1H, br d, J=8.3Hz)
  7.43–7.72 (3H, m)
  7.72–7.96 (3H, m)
  8.07 (1H, s)

Example 65

N-Cyclohexyl-2-hydroxy-2-[2-(1-(2-quinolylcarbonyl)pyrrolidinyl)]acetamide

To 200.2 mg of N-cyclohexyl-2-hydroxy-2-(2-pyrrolidinyl)acetamide hydrochloride were added 138.5 mg of quinaldinic acid, 205.9 mg of 1-hydroxybenzotriazole and 2.5 ml of DMF. Under ice cooling, 112 μl of triethylamine and 204.5 mg of 1-ethyl-3-(3-dimethylaminopropyl) carbodiimide hydrochloride were added to the mixture. After stirring for 2 hours, the reaction mixture was stirred at room temperature for further 4 hours. The reaction solution was then diluted with 25 ml of ethyl acetate. The resulting mixture was washed successively with 15 ml each of 4% sodium hydrogencarbonate aqueous solution and saturated sodium chloride aqueous solution. The organic layer was dried over anhydrous sodium sulfate and concentrated under vacuum to give 493 mg of an oily substance. The oily substance was purified by column chromatography (silica gel, developed with dichloromethane-methanol-triethylamine). The purified fraction was again purified by column chromatography (Sephadex LH-20, developed with methanol) to give 287.6 mg of the title compound as a colorless transparent amorphous solid. Yield, 99.1%.

FAB-MS m/z 382 (M+1)⁺

Example 66

N-Cyclohexyl-2-oxo-2-[2-(1-(2-quinolylcarbonyl)pyrrolidinyl)]acetamide

To 287.6 mg of N-cyclohexyl-2-hydroxy-2-[2-(1-(2-quinolylcarbonyl)pyrrolidinyl)]acetamide were added 1.43 ml of acetic anhydride and 1.40 ml of DMSO. The mixture was stirred at room temperature for 24 hours. At the end of the reaction, 40 ml of saturated sodium hydrogencarbonate aqueous solution was gradually added to the reaction solution. The aqueous layer was extracted 3 times with 20 ml each of dichloromethane. The oily layer was dried over anhydrous sodium sulfate and concentrated under vacuum to give an oily substance. The substance was purified by column chromatography(silica gel, developed with dichloromethane-acetonitrile-acetic acid) to give 173.3 mg of the title compound as a colorless needles. Yield, 60.6%.

melting point: 160–161° C.
[α]24/D–39.3° (c 1.00, CHCl₃)

FAB-MS m/z 380 (M+1)⁺
1H-NMR (CDCl₃) δ:
  1.02–1.51 (5H, m)
  1.59–1.84 (3H, m)
  1.85–2.18 (5H, m)
  2.48 (1H, m)
  3.80–3.98 (2H, m)
  4.03 (1H, m)
  6.39 (1H, dd, J=3.9, 9.3Hz)
  6.95 (1H, d, J=8.3Hz)
  7.56 (1H, m)
  7.63 (1H, m)
  7.80 (1H, d)
  7.89 (1H, d)
  8.22 (1H, d)
  8.28 (1H, d)

Example 67

N-Cyclohexyl-2-hydroxy-2-[2-(1-cinnamoylpyrrolidinyl)]acetamide

To 150.2 mg of N-cyclohexyl-2-hydroxy-2-(2-pyrrolidinyl)acetamide hydrochloride were added 1.5 ml of dry tetrahydrofuran and 184 μl of triethylamine. A solution of 116.0 mg of cinnamoyl chloride in 3 ml of dry tetrahydrofuran was then dropwise added to the mixture over 30 minutes. After completion of the dropwise addition, the mixture was stirred for 2 hours - and the solvent was distilled off under vacuum. After 6 ml of 1 N hydrochloric acid was added to the solid obtained, the mixture was extracted once with 8 ml of ethyl acetate and twice with 4 ml each of ethyl acetate. The oily layers were combined and washed successively with 12 ml each of saturated sodium hydrogencarbonate aqueous solution and saturated sodium chloride aqueous solution. The oily layer was dried over anhydrous sodium sulfate and concentrated under vacuum to give an amorphous solid. The solid was purified by column chromatography (silica gel, developed with dichloromethane-methanol) to give 178.6 mg of the title compound as an amorphous solid. Yield, 87.7%.

FAB-MS m/z 357 (M+1)⁺

Example 68

N-Cyclohexyl-2-oxo-2-[2-(1-cinnamoylpyrrolidinyl)]acetamide

To 178.4 mg of N-cyclohexyl-2-hydroxy-2-[2-(1-cinnamoylpyrrolidinyl)]acetamide were added 49.3 mg of pyridine-trifluoroacetate, 287.8 mg of 1-ethyl-3-(3-dimethylaminopropyl)carbodiimide hydrochloride and 2.0 ml of DMSO. The mixture was stirred at room temperature for 5 hours. At the end of the reaction, the reaction solution was diluted with 20 ml of ethyl acetate and then washed with 20 ml of water. The oily layer was dried over anhydrous sodium sulfate and concentrated under vacuum to give a light yellow solid. The solid was purified by column chromatography (silica gel, developed with dichloromethane-ethyl acetate-acetonitrile) to give 160.1 mg of a white solid. Yield, 90.3%. After the solid was dissolved in 6 ml of ethyl acetate and 2 ml of dichloromethane, 20 ml of hexane was gradually added to the solution, whereby crystals were slowly grown to give the title compound as colorless transparent needles.

melting point: 184–185° C.
[α]27/D–38.61 (c1.08, CHCl₃)
FAB-MS m/z 355 (M+1)⁺

1H-NMR (CDCl₃) δ:
  1.08–1.49 (5H, m)
  1.55–2.19 (8H, m)
  2.39 (1H, m)
  3.67–3.94 (3H, m)
  5.40 (1H, dd, J=5.6, 8.9Hz)
  6.74 (1H, d, J=15.5Hz)
  6.79 (1H, br d, overlapping)
  7.30–7.59 (5H, m)
  7.68 (1H, d, J=15.5Hz)

Example 69

N-Cyclohexyl-2-hydroxy-2-[2-(1-(3-(4-chlorophenyl)acryloyl)pyrrolidinyl)]acetamide To 151.6 mg of N-cyclohexyl-2-hydroxy-2-(2-pyrrolidinyl)acetamide hydrochloride were added 110.6 mg of p-chlorocinnamic acid, 156.2 mg of 1-hydroxybenzotriazole and 2.0 ml of DMF. Under ice cooling 85 μl of triethylamine and 154.8 mg of 1-ethyl-3-(3-dimethylaminopropyl)carbodiimide hydrochloride were added to the mixture. After stirring for 2 hours, the mixture was stirred at room temperature for further 4 hours. Thereafter, the reaction solution was diluted with 20 ml of ethyl acetate and the diluted solution was washed successively with 10 ml each of 4% sodium hydrogencarbonate aqueous solution, 1% citric acid aqueous solution and saturated sodium chloride aqueous solution. The organic layer was dried over anhydrous sodium sulfate and then concentrated under vacuum to give 335 mg of an oily substance. The oily substance was purified by column chromatography (silica gel, developed with dichloromethane-methanol) to give 206.4 mg of the title compound as a colorless transparent amorphous solid. Yield, 91.5%.

FAB-MS m/z 391 (M+1)⁺

Example 70

N-Cyclohexyl-2-oxo-2-[2-(1-(3-(4-chlorophenyl)acryloyl)pyrrolidinyl)]acetamide

To 206.0 mg of N-cyclohexyl-2-hydroxy-2-[2-(1-(3-(4-chlorophenyl)acryloyl)pyrrolidinyl)]acetamide were added 51.9 mg of pyridine trifluoroacetate, 303.1 mg of 1-ethyl-3-(3-dimethylaminopropyl)carbodiimide hydrochloride and 2.0 ml of DMSO. The mixture was stirred at room temperature for 14 hours. At the end of the reaction, the reaction solution was diluted with 20 ml of ethyl acetate and then washed with 20 ml of water. The oily layer was dried over anhydrous sodium sulfate and concentrated under vacuum to give 421 mg of an oily substance. The oily substance was purified by column chromatography (silica gel, developed with dichloromethane-acetonitrile) to give 171.2 mg of a white solid. Yield, 83.5%.

After the solid was dissolved in 2 ml of dichloromethane, 26 ml of hexane was gradually added to the solution, whereby crystals grew to give the title compound as colorless transparent needles.

melting point: 178–180° C.
[α]26/D–16.6° (c 1.01, CHCl₃)
FAB-MS m/z 389 (M+1)⁺
1H-NMR (CDCl₃) δ:
  1.13–1.46 (5H, m)
  1.53–1.80 (3H, m)
  1.81–2.18 (5H, m)
  2.37 (1H, m)

3.67–3.91 (3H, m)
5.37 (1H, dd, J=5.9, 8.8Hz)
6.69 (1H, d, J=15.4Hz)
6.74 (1H, br d, J=7.8Hz)
7.33 (2H, m)
7.43 (2H, m)
7.61 (1H, d, J=15.4Hz)

Example 71

N-Cyclohexyl-2-hydroxy-2-[2-(1-(3-(3-pyridyl)acryloyl)pyrrolidinyl)]acetamide

To 150.2 mg of N-cyclohexyl-2-hydroxy-2-(2-pyrrolidinyl)acetamide hydrochloride were added 89.7 mg of 3-(3-pyridyl)acrylic acid, 154.5 mg of 1-hydroxybenzotriazole and 2.0 ml of DMF. Under ice cooling, 84 µl of triethylamine and 153.4 mg of 1-ethyl-3-(3-dimethylaminopropyl)carbodiimide hydrochloride were added to the solution. After stirring for 2 hours, the reaction mixture was stirred at room temperature for further 4 hours. Then the reaction solution was diluted with 20 ml of ethyl acetate. The diluted solution was washed successively with 15 ml each of 4% sodium hydrogencarbonate aqueous solution and saturated sodium chloride aqueous solution. The organic layer was dried over anhydrous sodium sulfate and concentrated under vacuum to give 276 mg of an oily substance. The oily substance was purified by column chromatography (silica gel, developed with dichloromethane-methanol-triethylamine) to give 189.5 mg of the title compound as an amorphous solid. Yield, 92.8%.

FAB-MS m/z 358 (M+1)$^+$

Example 72

N-Cyclohexyl-2-oxo-2-[2-(1-(3-(3-pyridyl)acryloyl)pyrrolidinyl)]acetamide

To 189.0 mg of N-cyclohexyl-2-hydroxy-2-[2-(1-(3-(3-pyridyl)acryloyl)pyrrolidinyl)]acetamide were added 53.7 mg of pyridine trifluoroacetate, 305.2 mg of 1-ethyl-3-(3-dimethylaminopropyl)carbodiimide hydrochloride and 2.0 ml of DMSO. The mixture was stirred at room temperature for 7 hours. At the end of the reaction, a sodium hydrogencarbonate solution (23.4 mg dissolved in 20 ml of water) was added to the reaction solution. The solution was extracted 3 times with 10 ml each of dichloromethane. The oily layer was dried over anhydrous sodium sulfate and concentrated under vacuum to give light yellow needles. The crystals were purified by column chromatography (silica gel, developed with chloroform-methanol) to give 168.1 mg of the title compound as colorless transparent needles. Yield, 89.4%.

melting point: 181–182° C.
[α]22/D–14.9° (c 1.01, CHCl$_3$)
FAB-MS m/z 356 (M+1)$^+$
1H-NMR (CDCl$_3$) δ:
 1.07–1.50 (5H, m)
 1.55–2.21 (8H, m)
 2.40 (1H, m)
 3.67–3.95 (3H, m)
 5.42 (1H, dd, J=5.6, 8.9Hz)
 6.79 (1H, br d, overlapping)
 6.82 (1H, d, J=15.5Hz)
 7.32 (1H, dd, J=5.0, 7.9Hz)
 7.67 (1H, d, J=15.5Hz)
 7.82 (1H, m)
 8.59 (1H, br d)
 8.77 (1H, br s)

Example 73

N-Cyclohexyl-2-hydroxy-2-[2-(1-(2-pyridylcarbonyl)pyrrolidinyl)]acetamide

To 152.4 mg of N-cyclohexyl-2-hydroxy-2-(2-pyrrolidinyl)acetamide hydrochloride were added 75.0 mg of picolinic acid, 156.7 mg of 1-hydroxybenzotriazole and 2.0 ml of DMF. Under ice cooling, 85 µl of triethylamine and 155.6 mg of 1-ethyl-3-(3-dimethylaminopropyl)carbodiimide hydrochloride were added to the mixture. After stirring for 2 hours, the reaction mixture was stirred at room temperature for further 4 hours. The reaction solution was then diluted with 20 ml of ethyl acetate. The resulting mixture was washed successively with 15 ml each of 4% sodium hydrogencarbonate aqueous solution and saturated sodium chloride aqueous solution. The organic layer was dried over anhydrous sodium sulfate and concentrated under vacuum to give 275 mg of an oily substance. The oily substance was purified by column chromatography (silica gel, developed with dichloromethane-methanol-triethylamine) to give 165.1 mg of the title compound as a colorless transparent amorphous solid. Yield, 85.9%.

FAB-MS m/z 332 (M+1)$^+$

Example 74

N-Cyclohexyl-2-oxo-2-[2-(1-(2-pyridylcarbonyl)pyrrolidinyl)]acetamide

To 164.7 mg of N-cyclohexyl-2-hydroxy-2-[2-(1-(2-pyridylcarbonyl)pyrrolidinyl)]acetamide were added 48.2 mg of pyridine trifluoroacetate, 285.8 mg of 1-ethyl-3-(3-dimethylaminopropyl)carbodiimide hydrochloride and 2.0 ml of DMSO. The mixture was stirred at room temperature for 7 hours. At the end of the reaction, a sodium hydrogencarbonate solution (21.0 mg of sodium hydrogencarbonate dissolved in 20 ml of water) was added to the reaction solution. The solution was extracted 3 times with 10 ml each of dichloromethane. After washing with 15 ml of water, the oily layer was dried over anhydrous sodium sulfate and concentrated under vacuum to give a brown syrup-like substance. The substance was purified by column chromatography (silica gel, developed with dichloromethane-acetonitrile-acetic acid) to give 149.3 mg of the title compound as colorless transparent gum. Yield, 91.2%.

[α]23/D+22.0° (c 1.00, CHCl$_3$)
FAB-MS m/z 330 (M+1)$^+$
1H-NMR (CDCl$_3$) δ:
 1.12–1.54 (5H, m)
 1.55–1.87 (3H, m)
 1.88–2.12 (5H, m)
 2.35 (1H, m)
 3.71–3.94 (2H, m)
 4.00 (1H, m)
 5.89 (1H, dd, J=2.7, 9.0Hz)
 6.98 (1H, d, J=8.3Hz)
 7.31 (1H, m)
 7.79 (1H, m)
 8.16 (1H, d)
 8.24 (1H, d)

Example 75

N-Cyclohexyl-2-hydroxy-2-[2-(1-(3-phenoxybenzoyl)pyrrolidinyl)]acetamide

To 103.2 mg of N-cyclohexyl-2-hydroxy-2-(2-pyrrolidinyl)acetamide hydrochloride were added 88.6 mg of 3-phenoxybenzoic acid, 111.9 mg of 1-hydroxybenzotriazole and 1.5 ml of DMF. Under ice cooling, 58 μl of triethylamine and 105.4 mg of 1-ethyl-3-(3-dimethylaminopropyl)carbodiimide hydrochloride were added to the mixture. After stirring for 2 hours, the reaction mixture was stirred at room temperature for further 6 hours. The reaction solution was then diluted with 15 ml of ethyl acetate. The diluted solution was washed successively with 10 ml each of 4% sodium hydrogencarbonate aqueous solution, 10% citric acid aqueous solution and saturated sodium chloride aqueous solution. The organic layer was dried over anhydrous sodium sulfate and concentrated under vacuum to give 26075 mg of an oily substance. The oily substance was purified by column chromatography (silica gel, developed with dichloromethane-methanol) to give 161.7 mg of the title compound as a colorless transparent amorphous solid. Yield, 97.4%.

FAB-MS m/z 423 (M+1)$^+$

Example 76

N-Cyclohexyl-2-oxo-2-[2-(1-(3-phenoxybenzoyl) pyrrolidinyl)]acetamide

To 161.3 mg of N-cyclohexyl-2-hydroxy-2-[2-(1-(3-phenoxybenzoyl)pyrrolidinyl)]acetamide were added 0.72 ml of acetic anhydride and 1.5 ml of DMSO. The mixture was stirred at room temperature for 24 hours. At the end of the reaction, 25 ml of water was added to the reaction solution. After stirring for 40 minutes, the aqueous layer was extracted 3 times with 10 ml each of ethyl acetate. The oily layer was dried over anhydrous sodium sulfate and concentrated under vacuum to give 359 mg of an oily substance. The substance was purified by column chromatography (silica gel, developed with dichloromethane-acetonitrile) to give 121.4 mg of the title compound as a colorless transparent amorphous solid. Yield, 75.6%.

melting point: 40–42° C.
[α]23/D–34.4° (c 1.05, CHCl$_3$)
FAB-MS m/z 421 (M+1)$^+$
1H-NMR (CDCl$_3$) δ:
 1.07–1.50 (5H, m)
 1.55–2.19 (8H, m)
 2.43 (1H, m)
 3.50–3.89 (3H, m)
 5.39 (1H, dd, J=6.0, 7.7Hz)
 6.76 (1H, br d, J=7.8Hz)
 6.89–7.50 (9H, m)

Example 77

N-Cycloheptyl-2-hydroxy-2-[2-(1-(2-naphthoyl) pyrrolidinyl)]acetamide

To 149.5 mg of N-cycloheptyl-2-hydroxy-2-(2-pyrrolidinyl)acetamide hydrochloride were added 98.2 mg of 2-naphthoenic acid, 146.0 mg of 1-hydroxybenzotriazole and 2 ml of DMF. Under ice cooling 80 μl of triethylamine and 144.9 mg of 1-ethyl-3-(3-dimethylaminopropyl) carbodiimide hydrochloride were added to the solution. After stirring for 2 hours, stirring was continued at room temperature for further 3 hours. Thereafter, the reaction solution was diluted with 20 ml of ethyl acetate and the diluted solution was washed successively with 10 ml each of 4% sodium hydrogencarbonate aqueous solution, 10% citric acid aqueous solution and saturated sodium chloride aqueous solution. The organic layer was dried over anhydrous sodium sulfate and then concentrated under vacuum to give 270 mg of a syrup-like substance. The substance was purified by column chromatography (silica gel, developed with dichloromethane-methanol) to give 200.1 mg of the title compound as a colorless transparent syrup-like substance. Yield, 93.9%.

FAB-MS m/z 395 (M+1)$^+$

Example 78

N-Cycloheptyl-2-oxo-2-[2-(1-(2-naphthoyl) pyrrolidinyl)]acetamide

To 199.7 mg of N-cycloheptyl-2-hydroxy-2-[2-(1-(2-naphthoyl)pyrrolidinyl)]acetamide were added 0.96 ml of acetic anhydride and 1.0 ml of DMSO. The mixture was stirred at room temperature for 24 hours. At the end of the reaction, 20 ml of water was added to the reaction solution followed by stirring for 40 minutes. The aqueous layer was extracted 3 times with 10 ml each of dichloromethane. The oily layer was dried over anhydrous sodium sulfate and concentrated under vacuum to give a partially crystalline solid. The solid was purified by column chromatography (silica gel, developed with dichloromethane-acetonitrile) to give 176.4 mg of the title compound as colorless transparent needles. Yield, 88.8%.

melting point: 114–115° C.
[α]24/D–30.6° (c 1.01, CHCl$_3$)
FAB-MS m/z 393 (M+1)$_3$
1H-NMR (CDCl$_3$) δ:
 1.20–1.80 (10H, m)
 1.84–2.12 (5H, m)
 2.48 (1H, m)
 3.65 (1H, m)
 3.76 (1H, m)
 3.96 (1H, m)
 5.47 (1H, dd, J=6.6, 8.1Hz)
 6.87 (1H, br d, J=8.3Hz)
 7.45–7.60 (2H, m)
 7.64 (1H, m)
 7.74–7.95 (3H, m)
 8.06 (1H, S)

Example 79

N-Cyclohexyl-2-hydroxy-2-[2-(1-(N-(4-pyridylthio) acetyl)pyrrolidinyl)]acetamide In 1 ml of DMF were dissolved 107.5 mg of N-cyclohexyl-2-hydroxy-2-(2-pyrrolidinyl)acetamide hydrochloride, 83 mg of (4-pyridylthio)acetic acid and 84.5 mg of 1-hydroxybenzotriazole. Under ice cooling, 68.7 μl of triethylamine and 96.7 mg of 1-ethyl-3-(3-dimethylaminopropyl)carbodiimide hydrochloride were added to the solution. After stirring for 2 hours, the reaction mixture was stirred at room temperature for further 18 hours. After the reaction solution was diluted with 15 ml of ethyl acetate, the diluted solution was washed successively with 15 ml each of 4% sodium hydrogencarbonate aqueous solution, distilled water and saturated sodium chloride aqueous solution. The organic layer was dried over anhydrous sodium sulfate and concentrated under vacuum to give 123.6 mg of an oily substance. The substance was purified by column chromatography (silica gel, developed with dichloromethane-methanol) to give 119.6 mg of N-cyclohexyl-2-hydroxy-2-[2-(1-(N-(4-pyridylthio)acetyl) pyrrolidinyl)]acetamide as a colorless amorphous solid. Yield, 77.0%

FAB-MS m/z 378 (M+1)$^+$

Example 80

N-Cyclohexyl-2-oxo-2-[2-(1-(N-(4-pyridylthio)acetyl)pyrrolidinyl)]acetamide

After 109.7 mg of N-cyclohexyl-2-hydroxy-2-[2-(1-(N-(4-pyridylthio)acetyl)pyrrolidinyl)]acetamide was dissolved in 1.0 ml of DMSO, 0.6 ml of acetic anhydride was added to the solution. The mixture was stirred at room temperature for 20 hours. Then 5 ml each of ethyl acetate and 4% sodium hydrogencarbonate aqueous solution were added to the reaction mixture followed by stirring for 20 minutes. At the end of the reaction, 10 ml of 4% sodium hydrogencarbonate aqueous solution was added to reaction solution. The mixture was extracted twice with ethyl acetate. The extract was washed successively with distilled water and saturated sodium chloride aqueous solution. The organic layer was dried over anhydrous sodium sulfate and concentrated under vacuum to give 128.8 mg of an oily substance. The oily substance was purified by column chromatography (silica gel, developed with dichloromethane-acetonitrile) to give 56.6 mg of N-cyclohexyl-2-oxo-2-[2-(1-(N-(4-pyridylthio)acetyl)pyrrolidinyl)]acetamide as a colorless amorphous solid.

FAB-MS m/z 376 (M+1)$^+$

1H-NMR (CDCl$_3$) δ:
1.15–1.45 (5H, m)
1.60–2.15 (8H, m)
2.39 (1H, m)
3.5–3.8 (3H, m)
3.8 (2H, dd, J=14.7, 24.4Hz)
5.28 (1H, dd, J=5.4, 8.8Hz)
6.71 (1H, d, J=8.3)
7.24 (2H, dd, J=1.5, 4.4Hz)
8.41 (2H, dd, J=1.5, 4.4Hz)

Example 81

N-Cyclohexyl-2-hydroxy-2-[2-(1-(4-morpholinomethylbenzoyl)pyrrolidinyl)]acetamide In 5 ml of DMF were dissolved 191 mg of N-cyclohexyl-2-hydroxy-2-(2-pyrrolidinyl)acetamide hydrochloride and 193 mg of 4-morpholinomethylbenzoic acid hydrochloride. After 394 mg of Bop reagent and then 255 μl of triethylamine were added to the solution, the mixture was stirred at room temperature overnight. Then 30 ml of 4% sodium hydrogencarbonate aqueous solution was added to the reaction solution and the resulting mixture was extracted twice with ethyl acetate. After washing and drying, ethyl acetate was distilled off under vacuum. The residue was dissolved in a small volume of methanol and the solution was purified by Sephadex LH20 column chromatography. Methanol used as a developing solvent was distilled off under vacuum to give 245 mg of the title compound as a light yellow syrup-like substance.

Example 82

N-Cyclohexyl-2-hydroxy-2-[2-(1-(4-chloromethylbenzoyl)pyrrolidinyl)]acetamide

In 3 ml of DMF were dissolved 224 mg of N-cyclohexyl-2-hydroxy-2-(2-pyrrolidinyl)acetamide, 176 mg of 4-chloromethylbenzoic acid and 179.4 mg of 1-hydroxybenzotriazole. Under ice cooling, 199 mg of 1-ethyl-3-(3-dimethylaminopropyl)carbodiimide hydrochloride and 144 μl of triethylamine were added to the solution. After stirring overnight, ethyl acetate was added to the reaction and the mixture was washed successively with an acid and an alkali. After drying the solvent was distilled off to give 320 mg of a colorless solid. The solid was dissolved in a small volume of chloroform. The solution was adsorbed to a silica gel (WAKO GEL C300) column filled up with chloroform. The column was developed with chloroform and then with chloroform:methanol=30:1 to give a fraction containing the title compound. Yielded amount, 300 mg.

FAB-MS m/z 379 (M+1)$^+$

Example 83

N-Cyclohexyl-2-hydroxy-2-[2-(1-(4-morpholinomethylbenzoyl)pyrrolidinyl)]acetamide After 145 mg of N-cyclohexyl-2-hydroxy-2-[(2-(1-(4-chloromethylbenzoyl)pyrrolidinyl)]acetamide was dissolved in 3 ml of ethanol, 0.15 ml of morpholine was added to the solution. The mixture was heated to reflux for 4 hours. The solvent and excess morpholine were distilled off under vacuum and the residue was dissolved in a small volume of methanol. The solution was purified by Sephadex LH20 column chromatography. Methanol used as a developing solvent was distilled off under vacuum to give 173 mg of the title compound as a light yellow syrup-like substance.

FAB-MS: 430 (M+1)$^+$

TLC (n-PrOH:ACOH:H$_2$O=3:1:1)

Rf=0.48

Example 84

N-Cyclohexyl-2-oxo-2-[2-(1-(4-morpholinomethylbenzoyl)pyrrolidinyl)]acetamide

After 173 mg of N-cyclohexyl-2-hydroxy-2-[(2-(1-(4-morpholinomethylbenzoyl)pyrrolidinyl)]acetamide was dissolved in 2 ml of DMSO, 0.4 ml of acetic anhydride was added to the solution. The mixture was stirred at room temperature overnight. The reaction solution was purified by Sephadex LH20 column chromatography. Methanol used as a developing solvent was distilled off under vacuum. The residue was dissolved in a small volume of 50% hydrated methanol. The resulting solution was adsorbed to Lobar® column RP-8 (Merck, size B), which was developed with methanol:water:acetic acid=25:75: 0.3. UV absorption was monitored to obtain the fraction containing the title compound. The solvent was distilled off under vacuum and dried to give 77.5 mg of the title compound as colorless powders.

FAB-MS: 428 (M+1)$^+$

TLC (n-PrOH:AcOH:H$_2$O=3:1:1)

Rf=0.48

Example 85

N-Cyclohexyl-2-hydroxy-2-[2-(1-(4-piperidinomethvlbenzoyl)pyrrolidinyl)]acetamide After 141 mg of N-cyclohexyl-2-hydroxy-2-[(2-(1-(4-chloromethylbenzoyl)pyrrolidinyl)]acetamide was dissolved in 3 ml of ethanol, 148 μl of piperidine was added to the solution. The mixture was heated to reflux for 4 hours. The solvent and excess piperidine were distilled off under vacuum and the residue was dissolved in a small volume of methanol. The solution was purified by Sephadex LH20 column chromatography. Methanol used as a developing solvent was distilled off under vacuum to give 152 mg of the title compound as a light yellow syrup-like substance.

FAB-MS: 428 (M+1)$^+$
TLC (n-PrOH:ACOH:H$_2$O=3:1:1)
Rf=0.44

Example 86

N-Cyclohexyl-2-oxo-2-[2-(1-(4-piperidinomethylbenzoyl)pyrrolidinyl)]acetamide

After 137 mg of N-cyclohexyl-2-hydroxy-2-[(2-(1-(4-piperidinomethylbenzoyl)pyrrolidinyl)]acetamide was dissolved in 2 ml of DMSO, 320 μl of acetic anhydride was added to the solution. The mixture was stirred at room temperature overnight. The reaction solution was purified by Sephadex LH20 column chromatography. Methanol used as a developing solvent was distilled off under vacuum. The residue was dissolved in a small volume of 50% hydrated methanol. The resulting solution was adsorbed to Lobar® column RP-8 (Merck, size B), which was developed with methanol:water:acetic acid=25:75:0.3. UV absorption was monitored to obtain the fraction containing the title compound. The solvent was distilled off under vacuum and the residue was dissolved in ethanol. Two drops of 2 N hydrochloric acid were added to the solution. The solvent was distilled off under vacuum and dried to give 68.2 mg of the title compound as colorless powders.
FAB-MS: 426 (M+1)$^+$
TLC (n-PrOH:ACOH:H$_2$O=3:1:1)
Rf=0.45

Example 87

N-Cyclohexyl-2-hydroxy-2-[2-(1-(4-(1-imidazolylmethylbenzoyl)pyrrolidinyl)]acetamide After 166.3 mg of N-cyclohexyl-2-hydroxy-2-[(2-(1-(4-chloromethylbenzoyl)pyrrolidinyl)]acetamide was dissolved in 3.5 ml of ethanol, 149 mg of imidazole was added to the solution. The mixture was heated to reflux for 14 hours. The solvent was distilled off under vacuum and the residue was dissolved in a small volume of methanol. The solution was purified by Sephadex LH20 column chromatography. Methanol used as a developing solvent was distilled off under vacuum to give 135.5 mg of the title compound as a light yellow syrup-like substance.
FAB-MS: 411 (M+1)$^+$
TLC (n-PrOH:AcOH:H$_2$O=3:1:1)
Rf=0.41

Example 88

N-Cyclohexyl-2-oxo-2-[2-(1-(4-(1-imidazolylmethylbenzoyl)pyrrolidinyl)]acetamide After 127.6 mg of N-cyclohexyl-2-hydroxy-2-[(2-(1-(4-(1-imidazolylmethylbenzoyl)pyrrolidinyl)]acetamide was dissolved in 2 ml of DMSO, 360 μl of acetic anhydride was added to the solution. The mixture was stirred at room temperature overnight. The reaction solution was purified by Sephadex LH20 column chromatography. Methanol used as a developing solvent was distilled off under vacuum and dried to give 60.3 mg of the title compound as a light yellow syrup-like substance.
FAB-MS: 409 (M+1)$^+$
TLC (n-PrOH:AcOH:H$_2$O=3:1:1)
Rf=0.41

Example 89

N-Cyclohexyl-2-hydroxy-2-[2-(1-(N-benzyl-N-methylcarbamoyl)pyrrolidinyl)]acetamide In 1 ml of DMF and 1 ml of methylene chloride were dissolved 119.1 mg of N-cyclohexyl-2-hydroxy-2-(2-pyrrolidinyl)acetamide hydrochloride and 177.7 mg of benzylaminomethyl-N-succinimidyl carbamate. After 69.8 μl of triethylamine was added to the solution, the mixture was stirred at room temperature for 5 days. Then 1 N hydrochloric acid was added to the reaction mixture followed by extraction twice with chloroform. The extract was washed in succession with 1 N hydrochloric acid, water and saturated sodium chloride aqueous solution. After drying over anhydrous sodium sulfate, the extract was concentrated under vacuum and the residue was dissolved in methylene chloride. The solution was purified by column chromatography (silica gel, developed with dichloromethane-methanol) to give 157.4 mg of the title compound as a colorless amorphous solid.
FAB-MS m/z 407 (M+1)$^+$

Example 90

N-Cyclohexyl-2-oxo-2-[2-(1-(N-benzyl-N-methylcarbamoyl)pyrrolidinyl)]acetamide

N-Cyclohexyl-2-hydroxy-2-[2-(1-(N-benzyl-N-methylcarbamoyl)pyrrolidinyl)]acetamide was oxidized and purified in a manner similar to Example 80 to give N-cyclohexyl-2-oxo-2-[2-(1-(N-benzyl-N-methylcarbamoyl)pyrrolidinyl)]acetamide.
FAB-MS m/z 405 (M+1)$^+$

Example 91

2-Hydroxy-2-[2-(l1-(4-chlorobenzoyl)pyrrolidinyl)]acetic acid

In 10 ml of water was dissolved 744.5 mg of 2-hydroxy-2-(2-pyrrolidinyl)acetic acid hydrochloride. Then a solution of 1090 mg of 4-chlorobenzoic acid N-hydroxysuccinimide ester in 10 ml of dioxane was added to the solution. After 1.72 ml of triethylamine was added to the mixture, stirring was continued at room temperature for 18 hours. After completion of the reaction, 50 ml of 0.3 N hydrochloric acid was added to the reaction mixture followed by extraction twice with 50 ml each of ethyl acetate. The extract was washed in succession with 1 N hydrochloric acid and water. After drying over anhydrous sodium sulfate, the extract was filtrated and then concentrated. The residue was dissolved in methylene chloride. The solution was purified by column chromatography (silica gel, developed with dichloromethane-methanol-acetic acid) to give 660.2 mg of 2-hydroxy-2-[2-(1-(4-chlorobenzoyl)pyrrolidinyl)]acetic acid as a colorless amorphous solid.
FAB-MS m/z 284 (M+1)$^+$

Example 92

N-(2-Benzimidazolylmethyl)-2-hydroxy-2-[2-(1-(4-chlorobenzoyl)pyrrolidinyl)]acetamide After 127.5 mg of 2-hydroxy-2-[2-(1-(4-chlorobenzoylpyrrolidinyl)]acetic acid and 108.8 mg of 2-aminomethylbenzimidazole dihydrochloride were dissolved in 5 ml of DMF, 219.9 mg of Bop reagent and 207 μl of triethylamine were added to the solution. The mixture was reacted at room temperature for 2 hours and 40 minutes. Then 25 ml of 4% sodium hydrogencarbonate aqueous solution was added to the reaction mixture followed by extraction twice with ethyl acetate. After the ethyl acetate layer was .washed with water, the product was extracted with 1 N hydrochloric acid into the aqueous layer. The extract was adsorbed onto DIAION CHP-20 column (100 ml, filled up with water). After washing with water, elution was performed by continuously varying the concentration, using 0.1 N hydrochloric acid-methanol (1:4). The eluate was evaporated off to dryness under reduced pressure to give 105.6 mg of the title compound as a colorless amorphous solid.

Example 93

N-(2-Benzimidazolylmethyl)-2-oxo-2-[2-(1-(4-chlorobenzoyl)pyrrolidinyl)]acetamide To 99.2 mg of N-(2-benzimidazolylmethyl)-2-hydroxy-2-[2-(1-(4-chlorobenzoyl)pyrrolidinyl)]acetamide were added 0.2 ml of acetic anhydride and 2 ml of DMSO. The mixture was stirred at room temperature for 16.5 hours. At the end of the reaction, 20 ml of water was added to the reaction solution followed by extraction twice with ethyl acetate. The ethyl acetate layer was concentrated under vacuum. The concentrate was purified on Sephadex LH20 (filled up with methanol) column to give 69.8 mg of the crude product. The crude product was dissolved in methylene chloride and the solution was purified by column chromatography (silica gel, developed with dichloromethane-methanol) to give 31.5 mg of N-(2-benzimidazolylmethyl)-2-oxo-2-[2-(1-(4-chlorobenzoyl)pyrrolidinyl)]acetamide as a colorless transparent solid.

FAB-MS m/z 448 (M+1)$^+$
1H-NMR (CD$_3$OD) δ:
1.9–2.20 (3H, m)
2.45 (1H, m)
5 3.55–3.7 (2H, m)
4.73 (2H, dd, J=16.1, 22Hz)
5.42 (1H, dd, J=6.1, 9.0Hz)
7.15–7.54 (8H, m)

Example 94

N-(2-Morpholinoethyl)-2-hydroxy-2-[2-(1-(4-chlorobenzoyl)pyrrolidinyl)]acetamide After 113.7 mg of 2-hydroxy-2-[2-(1-(4-chlorobenzoylpyrrolidinyl)]acetic acid and 58 μl of N-aminoethylmorpholine were dissolved in 2 ml of DMF, 196.1 mg of Bop reagent and 62 μl of triethylamine were added to the solution. The mixture was reacted at room temperature for 3 hours. Then 30 ml of water was added to the reaction mixture and the solution was adsorbed onto DIAION CHP-20 column (100 ml, filled up with water). After washing with water, the column was eluted with 0.1 N hydrochloric acid-methanol (1:4). The eluate was evaporated off to dryness under reduced pressure and purified on Sephadex LH20 (filled up with methanol) column to give 136.6 mg of the title compound as a colorless amorphous solid.

FAB-MS m/z 433 (M+1)$^+$

Example 95

N-(2-Morpholinoethyl-2-oxo-2-[2-(1-(4-chlorobenzoyl)pyrrolidinyl)]acetamide

To 125 mg of N-(2-morpholinoethyl)-2-hydroxy-2-[2-(l1-(4-chlorobenzoyl)pyrrolidinyl)]acetamide were added 0.36 ml of acetic anhydride and 2 ml of DMSO. The mixture was stirred at room temperature for 18 hours. The reaction solution was purified on Sephadex LH20 (filled up with methanol) column to give 130.7 mg of the crude product. The crude product was dissolved in methylene chloride and the solution was purified by column chromatography (silica gel, developed with dichloromethane-methanol). The fractions considered to contain the title compound were collected by TLC and concentrated. A solution of dil. hydrochloric acid in ethyl acetate was added to the concentrate and the mixture was again concentrated to give 39.4 mg of N-(2-morpholinoethyl)-2-oxo-2-[2-(1-(4-chlorobenzoyl) pyrrolidinyl)]acetamide as a colorless amorphous solid.

FAB-MS m/z 394 (M+1)$^+$
1H-NMR (CD$_3$OD) δ:
1.15–1.45 (5H, m)
1.60–2.05 (8H, m)
2.45 (1H, m)
3.2–3.8 (2H, m)
4.41 (2H, s)
4.85 (8H, s)
5.39 (1H, dd, J=5.6, 8.5Hz)
7.56 (4H, S)

Example 96

N-(2-(2-Pyridyl)ethyl)-2-hydroxy-2-[2-(1-(4-chlorobenzoyl)pyrrolidinyl)]acetamide After 114.2 mg of 2-hydroxy-2-[2-(1-(4-chlorobenzoylpyrrolidinyl)]acetic acid and 53 μl of 2-aminoethylpyridine were dissolved in 2 ml of DMF, 177.5 mg of Bop reagent and 62 μl of triethylamine were added to the solution. The mixture was reacted at room temperature for 3 hours. Then 20 ml of water and 5 ml of 1 N hydrochloric acid were added to the reaction mixture. Thereafter the mixture was adsorbed onto DIAION CHP-20 column (100 ml, filled up with water). After washing with water, the column was eluted with 0.1 N hydrochloric acid-methanol (1:4). The eluate was evaporated off to dryness under reduced pressure and then purified on Sephadex LH20 (filled up with methanol) column to give 151.2 mg of the title compound as a colorless amorphous solid.

FAB-MS m/z 388 (M+1)$^+$

Example 97

N-(2-(2-Pyridyl)ethyl)-2-oxo-2-[2-(1-(4-chlorobenzoyl)pyrrolidinyl)]acetamide

To 150 mg of N-(2-(2-pyridyl)ethyl)-2-hydroxy-2-[2-(1-(4-chlorobenzoyl)pyrrolidinyl)]acetamide were added 0.3 ml of acetic anhydride and 3 ml of DMSO. The mixture was stirred at room temperature for 20 hours. The reaction mixture was purified on Sephadex LH20 (filled up with methanol) column to give the crude product. The crude product was dissolved in 3 ml of methanol and the solution was diluted with 17 ml of water. The diluted solution was adsorbed onto DIAION CHP-20 column (100 ml, filled up with water). After washing with water, elution was performed by continuously varying the concentration, using 0.1 N hydrochloric acid-methanol (1:4). The eluate was evaporated off to dryness under vacuum to give 128.1 mg of a colorless amorphous solid. The solid was dissolved in methylene chloride and the solution was purified by column chromatography (silica gel, developed with dichloromethane-methanol) to give 20.1 mg of N-(2-(2-pyridyl)ethyl)-2-oxo-2-[2-(1-(4-chlorobenzoyl) pyrrolidinyl)]acetamide as a colorless amorphous solid.

FAB-MS m/z 386 (M+1)$^+$

Example 98

N-(2-(2-Pyridyl)ethyl)-2-hydroxy-2-[2-(1-t-butoxycarbonylpyrrolidinyl)]acetamide After 199.4 mg of 2-hydroxy-2-[2-(1-t-butoxycarbonylpyrrolidinyl)]acetic acid was dissolved in 2 ml of DMF, 398.9 mg of Bop reagent and 125.2 μl of triethylamine were added to the solution. The mixture was stirred for 2 hours and at room temperature for further 13 hours. After completion of the reaction, 4% sodium hydrogencarbonate aqueous solution was added to the reaction mixture for dilution followed by extraction twice with ethyl acetate. The ethyl acetate layer was washed in succession with 4% sodium hydrogencarbonate aqueous solution and saturated sodium chloride aqueous solution. After drying over anhydrous sodium sulfate, the solvent was distilled off to give a white solid. The solid was then purified by column chromatography (silica gel, developed with dichloromethane-methanol) to give 281 mg of N-(2-(2-pyridyl)ethyl)-2-hydroxy-2-[2-(1-t-butoxycarbonylpyrrolidinyl)]acetamide as a colorless amorphous solid.

FAB-MS m/z 354 (M+1)$^+$

Example 99

N-(2-(2-Pyridyl)ethyl)-2-hydroxy-2-(2-pyrrolidinyl) acetamide hydrochloride

N-(2-(2-Pyridyl)ethyl)-2-hydroxy-2-[2-(1-t-butoxycarbonylpyrrolidinyl)]acetamide was treated with hydrochloric acid-dioxane in a manner similar to Example 2 to give N-(2-(2-pyridyl)ethyl)-2-hydroxy-2-(2-pyrrolidinyl)acetamide hydrochloride.

FAB-MS m/z 250 (M+1)$^+$

Example 100

N-(2-(2-Pyridyl)ethyl)-2-hydroxy-2-[2-(1-isonicotinonylpyrrolidinyl)]acetamide

N-(2-(2-Pyridyl)ethyl)-2-hydroxy-2-(2-pyrrolidinyl)acetamide hydrochloride was reacted with isonicotinic acid in a manner similar to Example 48 and further purified to give N-(2-(2-pyridyl)ethyl)-2-hydroxy-2-[2-(1-isonicotinonylpyrrolidinyl)]acetamide.

FAB-MS m/z 355 (M+1)$^+$

Example 101

N-(2-(2-Pyridyl)ethyl)-2-oxo-2-[2-(1-isonicotinonylpyrrolidinyl)]acetamide

N-(2-(2-Pyridyl)ethyl)-2-hydroxy-2-[2-(1-isonicotinonylpyrrolidinyl)]acetamide was oxidized in a manner similar to Example 97 to give N-(2-(2-pyridyl)ethyl)-2-oxo-2-[2-(1-isonicotinonylpyrrolidinyl)]acetamide.

FAB-MS m/z 353 (M+1)$^+$

Example 102

N-(2-(2-Pyridyl[]ethyl)-2-hydroxy-2-[2-(1-(4-pyridylthioacetyl)pyrrolidinyl)]acetamide N-(2-(2-Pyridyl)ethyl)-2-hydroxy-2-(pyrrolidinyl)acetamide hydrochloride was reacted with 4-pyridylthioacetic acid in a manner similar to Example 48 and further purified to give N-(2-(2-pyridyl)ethyl)-2-hydroxy-2-[2-(1-(4-pyridylthioacetyl)pyrrolidinyl)]acetamide.

FAB-MS m/z 401 (M+1)$^+$

Example 103

N-(2-(2-Pyridyl)ethyl)-2-oxo-2-[2-(1-(4-pyridylthioacetyl)pyrrolidinyl)]acetamide N-(2-(2-Pyridyl)ethyl)-2-hydroxy-2-[2-(1-(4-pyridylthioacetyl)pyrrolidinyl)]acetamide was oxidized in a manner similar to Example 97 to give N-(2-(2-pyridyl)ethyl)-2-oxo-2-[2-(1-(4-pyridylthioacetyl)pyrrolidinyl)]acetamide.

FAB-MS m/z 399 (M+1)$^+$

Example 104

N-Cyclopropyl-2-hydroxy-2-[2-(1-t-butoxycarbonylpyrrolidinyl)]acetamide

In 3.5 ml of DMF were dissolved 294.4 mg of 2-hydroxy-2-[2-(1-t-butoxycarbonylpyrrolidinyl)]acetic acid and 243.3 mg of 1-hydroxybenzotriazole. Under ice cooling, 104 μl of cyclopropylamine and 287.6 mg of 1-ethyl-3-(3-dimethylaminopropyl)carbodiimide hydrochloride were added to the solution. The mixture was stirred for 2 hours and for further 5 hours at room temperature. At the end of the reaction, 35 ml of ethyl acetate was added to the reaction mixture for dilution. The diluted mixture was washed in succession with 20 ml each of 4% sodium hydrogencarbonate aqueous solution, saturated sodium chloride aqueous solution and 10% citric acid aqueous solution. The oily layer was dried over anhydrous sodium sulfate and the solvent was distilled off to give 353.8 mg of an amorphous solid. The solid was purified by column chromatography (Sephadex LH20, developed with methanol) to give 283.2 mg of the product. Yield, 83.0%.

FAB-MS m/z 285 (M+1)$^+$

Example 105

N-Cyclopropyl-2-hydroxy-2-(2-pyrrolidinyl) acetamide hydrochloride

To 282.8 mg of N-cyclopropyl-2-hydroxy-2-[2-(1-t-butoxycarbonylpyrrolidinyl)]acetamide was added 4 ml of 4 N hydrochloric acid-dioxane solution under ice cooling. After stirring at room temperature for an hour, the solvent was distilled off to give a white solid. To the white solid was added 10 ml of ether. The mixture was stirred for 30 minutes in a suspended state, followed by filtration and drying. Thus, 208.0 mg of the title compound was obtained as a white solid. Yield, 94.8%.

Example 106

N-Cyclopropyl-2-hydroxy-2-[2-(1-(N-t-butoxycarbonylphenylalanyl)pyrrolidinyl)]acetamide In 1.2 ml of DMF were dissolved 114.4 mg of N-cyclopropyl-2-hydroxy-2-(2-pyrrolidinyl)acetamide hydrochloride, 144.4 mg of N-t-butoxycarbonylphenylalanine and 141.3 mg of 1-hydroxybenzotriazole. Under ice cooling, 77 μl of triethylamine and 142.0 mg of 1-ethyl-3-(3-dimethylaminopropyl) carbodiimide hydrochloride were added to the solution. After stirring for 2 hours, the reaction mixture was stirred at room temperature for further 4 hours. After the reaction solution was diluted with 12 ml of ethyl acetate, the diluted solution was washed successively with 5 ml each of 4% sodium hydrogencarbonate aqueous solution, saturated sodium chloride aqueous solution and 10% citric acid aqueous solution. The organic layer was dried over anhydrous sodium sulfate and concentrated under vacuum to give 380 mg of an oily substance. The oily substance was purified by column chromatography (silica gel, developed with dichloromethane-methanol) to give 204.4 mg of the title compound as a crystalline solid. Yield, 91.4%

FAB-MS m/z 432 (M+1)$^+$

Example 107

N-Cyclopropyl-2-hydroxy-2-[2- (1- (N-(3-phenoxybenzoyl)phenylalanyl)pyrrolidinyl) acetamide To 204.1 mg of N-cyclopropyl-2-hydroxy-2-[2-(1-(N-t-butoxycarbonylphenylalanyl)pyrrolidinyl)]acetamide was added 2.0 ml of trifluoroacetic acid. After stirring at room temperature for 40 minutes, the solvent was distilled off and 2 ml of toluene was added to the residue followed by distilling off the solvent. This cycle of the procedures was repeated twice to give N-cyclopropyl-2-hydroxy-2-[2-(1-phenylalanylpyrrolidinyl)]acetamide trifluoroacetate as an amorphous solid. After 106.4 mg of 3-phenoxybenzoic acid, 127.8 mg of 1-hydroxybenzotriazole and 2.5 ml of DMF were added to the solid, 73 μl of triethylamine and 126.9 mg of 1-ethyl-3-(3-dimethylaminopropyl)carbodiimide hydrochloride were added to the mixture. After stirring for 2 hours, stirring was continued at room temperature for further 17 hours. Thereafter, the reaction solution was diluted with 25 ml of ethyl acetate and the diluted solution was washed successively with 20 ml each of 4% sodium hydrogencarbonate aqueous solution, 10% citric acid aqueous solution and saturated sodium chloride aqueous solution. The organic layer was dried over anhydrous sodium sulfate and the solvent was then distilled off to give 341 mg of an oily substance. The oily substance was purified by column chromatography (silica gel, developed with dichloromethane-methanol) to give 198.3 mg of the title compound as a colorless amorphous solid. Yield, 79.5%.

FAB-MS m/z 528 (M+1)$^+$

Example 108

N-Cyclopropyl-2-oxo-2-[2-(1-(N-(3-phenoxybenzoyl)phenylalanyl)pyrrolidinyl)] acetamide To 185.9 mg of N-cyclopropyl-2-hydroxy-2-[2-(1-(N-(3-phenoxybenzoyl)phenylalanyl)pyrrolidinyl)]acetamide were added 0.67 ml of acetic anhydride and 1.0 ml of DMSO. The mixture was stirred at room temperature for 24 hours. At the end of the reaction, 20 ml of water was added to the reaction solution followed by stirring for 30 minutes. The resulting aqueous layer was extracted 3 times with 10 ml each of dichloromethane. The oily layer was dried over anhydrous sodium sulfate and concentrated under vacuum to give an oily substance. The oily substance was purified by column chromatography (silica gel, developed with dichloromethane-acetonitrile) to give 167.5 mg of the title compound as a colorless amorphous solid. Yield: 90.4%.

melting point: 70–72° C.

[α]24/D–48.6° (c 1.48, CHCl$_3$)

FAB-MS m/z 526 (M+1)$^+$

1H-NMR (CDCl$_3$) δ:
  0.61, 0.84 (4H (each 2H), two m)
  1.78–2.05 (3H, m)
  2.32 (1H, m)
  2.78 (1H, m)
  3.06 (1H, dd, J=5.9, 13.7Hz)
  ca. 3.15 (1H, m, overlapping)
  3.16 (1H, dd, J=7.1, 13.7Hz)
  3.72 (1H, m)
  5.10 (1H, ddd, J=5.9, 7.1, 7.8Hz)
  5.30 (1H, dd, J=6.3, 8.3Hz)
  6.93 (1H, d, J=2.9Hz)
  6.96–7.05 (3H, m)
  7.12 (2H, m)
  7.17–7.46 (10H, m)

Example 109

N-Cyclooctyl-2-hydroxy-2-[2-(1-t-butoxycarbonylpyrrolidinyl)]acetamide

In 6 ml of DMF were dissolved 490.5 mg of 2-hydroxy-2-[2-(1-t-butoxycarbonylpyrrolidinyl)]acetic acid and 405.5 mg of 1-hydroxybenzotriazole. Under ice cooling, 0.35 ml of cyclooctylamine and 479.2 mg of 1-ethyl-3-(3-dimethylaminooctyl)carbodiimide hydrochloride were added to the solution. The mixture was stirred for 2 hours and for further 5 hours at room temperature. At the end of the reaction, 60 ml of ethyl acetate was added to the reaction mixture for dilution. The diluted mixture was washed in succession with 30 ml each of 4% sodium hydrogencarbonate aqueous solution, saturated sodium chloride aqueous solution, 10% citric acid aqueous solution and again saturated sodium chloride aqueous solution. The oily layer was dried over anhydrous sodium sulfate and the solvent was distilled off to give 977.1 mg of a crystalline solid. The solid was purified by column chromatography (Sephadex LH20, developed with methanol) to give 682.4 mg of the product. Yield, 96.3%.

FAB-MS m/z 355 (M+1)$^+$

Example 110

N-Cyclooctyl-2-hydroxy-2-(2-pyrrolidinyl) acetamide hydrochloride

To 682.1 mg of N-cyclooctyl-2-hydroxy-2-[2-(1-t-butoxycarbonylpyrrolidinyl)]acetamide was added 12 ml of 4 N hydrochloric acid-dioxane solution under ice cooling. After stirring at room temperature for an hour, the solvent was distilled off to give a white solid. To the white solid was added 20 ml of ether. The mixture was stirred for 30 minutes in a suspended state, followed by filtration and drying. Thus, 548.8 mg of the title compound was obtained as white powders. Yield, 98.1%.

Example 111

N-Cyclooctyl-2-hydroxy-2-[2-(1-(N-t-butoxycarbonylphenylalanyl)pyrrolidinyl)]acetamide In 1.0 ml of DMF were dissolved 107.6 mg of N-cyclooctyl-2-hydroxy-2-(2-pyrrolidinyl)acetamide hydrochloride, 108.2 mg of N-t-butoxycarbonylphenylalanine and 100.0 mg of 1-hydroxybenzotriazole. Under ice cooling, 55 μl of triethylamine and 99.3 mg of 1-ethyl-3-(3-dimethylaminooctyl)carbodiimide hydrochloride were added to the solution. After stirring for 2 hours, the reaction mixture was stirred at room temperature for further 5 hours. After the reaction solution was diluted with 15 ml of ethyl acetate, the diluted solution was washed successively with 10 ml each of 4% sodium hydrogencarbonate aqueous solution and 10% citric acid aqueous solution. The organic layer was dried over anhydrous sodium sulfate and concentrated under vacuum to give 316 mg of an oily substance. The oily substance was purified by column chromatography (silica gel, developed with dichloromethane-methanol) to give 177.4 mg of the title compound as a crystalline solid. Yield, 95.6%

FAB-MS m/z 502 (M+1)$^+$

Example 112

N-Cyclooctyl-2-hydroxy-2-[2-(1-(N-(3-phenoxybenzoyl)phenylalanyl)pyrrolidinyl) acetamide To 177.1 mg of N-cyclooctyl-2-hydroxy-2-[2-(1-(N-t-butoxycarbonylphenylalanyl)pyrrolidinyl)]acetamide was added 2.0 ml of trifluoroacetic acid. After stirring at room temperature for 40 minutes, the solvent was distilled off and 2 ml of toluene was added to the residue followed by distilling off the solvent. This cycle of the procedures was repeated 3 times to give N-cyclooctyl-2-hydroxy-2-[2-(1-phenylalanylpyrrolidinyl)]acetamide trifluoroacetate as an amorphous solid. After 79.8 mg of 3-phenoxybenzoic acid, 95.4 mg of 1-hydroxybenzotriazole and 2.5 ml of DMF were added to the solid, 55 µl of triethylamine and 94.7 mg of 1-ethyl-3-(3-dimethylaminopropyl)carbodiimide hydrochloride were added to the mixture. After stirring for 2 hours, stirring was continued at room temperature for further 4 hours. Thereafter, the reaction solution was diluted with 25 ml of ethyl acetate and the diluted solution was washed successively with 20 ml each of 4% sodium hydrogencarbonate aqueous solution and 10% citric acid aqueous solution. The organic layer was dried over anhydrous sodium sulfate and the solvent was then distilled off to give 303 mg of an oily substance. The oily substance was purified by column chromatography (silica gel, developed with dichloromethane-methanol) to give 199.8 mg of the title compound as a colorless amorphous solid. Yield,. 94.7%.

FAB-MS m/z 598 (M+1)$^+$

Example 113

N-Cyclooctyl-2-oxo-2-[2-(1-(N-(3-phenoxybenzoyl) phenylalanyl)pyrrolidinyl)]acetamide To 199.5 mg of N-cyclooctyl-2-hydroxy-2-(2-(1-(N-(3-phenoxybenzoyl)phenylalanyl)pyrrolidinyl)]acetamide were added 0.63 ml of acetic anhydride and 1.0 ml of DMSO. The mixture was stirred at room temperature for 24 hours. At the end of the reaction, 20 ml of water was added to the reaction solution followed by stirring for 30 minutes. The resulting aqueous layer was extracted 3 times with 10 ml each of dichloromethane. The oily layer was dried over anhydrous sodium sulfate and concentrated under vacuum to give an oily substance. The oily substance was purified by column chromatography (silica gel, developed with dichloromethane-acetonitrile) to give 182.3 mg of the title compound as a colorless amorphous solid. Yield, 91.7%.

melting point: 67.5–69.5° C.

$[\alpha]26/D$–45.1° (c 1.26, CHCl$_3$)

FAB-MS m/z 596 (M+1)$^+$

1H-NMR (CDCl$_3$) δ:
 1.40–2.05 (17H, m)
 2.33 (1H, m)
 3.07 (1H, dd, J=5.9, 13.7Hz)
 ca. 3.14 (1H, m, overlapping)
 3.18 (1H, dd, J=7.3, 13.7Hz)
 3.70 (1H, m)
 3.96 (1H, m)
 5.11 (1H, ddd, J=5.9, 7.3, 7.8Hz)
 5.33 (1H, dd, J=5.9, 8.3Hz)
 6.85 (1H, d, J=8.3Hz)
 6.99 (3H, m)
 7.12 (2H, m)
 7.18–7.49 (10H, m)

Example 114

N-Cyclohexyl-2-hydroxy-2-[2-(1-(N-(2-quinolylcarbonyl)phenylalanyl)pyrrolidinyl)] acetamide After 164.0 mg of N-cyclohexyl-2-hydroxy-2-[2-(1-phenylalanylpyrrolidinyl)]acetamide hydrochloride, 79.0 mg of quinaldinic acid and 108.4 mg of 1-hydroxybenzotriazole were dissolved in 2 ml of DMF, 62 µl of triethylamine and 107.4 mg of 1-ethyl-3-(3-dimethylaminopropyl)carbodiimide hydrochloride were added to the solution under ice cooling. Thereafter the reaction mixture was stirred for 2 hours and at room temperature for further 4 hours. The reaction solution was then diluted with 20 ml of ethyl acetate. The diluted solution was washed successively with 20 ml each of 4% sodium hydrogencarbonate aqueous solution and saturated sodium chloride aqueous solution. The organic layer was dried over anhydrous sodium sulfate and concentrated under vacuum to give 311 mg of an oily substance. The oily substance was purified by column chromatography (silica gel, developed with dichloromethane-methanol-triethylamine) to give 203.1 mg of the title compound as a colorless amorphous solid. Yield, 96.0%.

FAB-MS m/z 529 (M+1)$^+$

Example 115

N-Cyclohexyl-2-oxo-2-[2-(1-(N-(2-quinolylcarbonyl)phenylalanyl)pyrrolidinyl)] acetamide To 203.0 mg of N-cyclohexyl-2-hydroxy-2-[2-(1-(N-(2-quinolylcarbonyl)phenylalanyl)pyrrolidinyl)]acetamide were added 0.73 ml of acetic anhydride and 0.7 ml of DMSO. The mixture was stirred at room temperature for 29 hours. At the end of the reaction, 30 ml of 4% sodium hydrogencarbonate aqueous solution was added to the reaction solution. The aqueous layer was extracted 3 times with 10 ml each of dichloromethane. The oily layer was dried over anhydrous sodium sulfate and concentrated under vacuum to give an oily substance. The oily substance was purified by column chromatography (silica gel, developed with dichloromethane-acetonitrile-acetic acid) to give 146.4 mg of the title compound as colorless needles. Yield, 72.4%.

melting point: 83–84° C.

$[\alpha]26$-D–42.1° (c 0.86, CHCl$_3$)

FAB-MS m/z 527 (M+1)$^+$

1H-NMR (CDCl$_3$) δ:
 1.12–1.48 (5H, m)
 1.64 (1H, m)
 1.70–2.06 (7H, m)
 2.32 (1H, m)
 ca. 3.14 (1H, m, overlapping)
 3.15 (1H, dd, J=6.8, 13.7Hz)
 3.28 (1H, dd, J=7.3, 13.7Hz)
 3.70–3.83 (2H, m)
 5.22 (1H, ddd, J=6.8, 7.3, 8.8z)
 5.36 (1H, dd, J=6.1, 8.5Hz)
 6.82 (1H, d, J=8.3Hz)
 7.20–7.44 (5H, m)
 7.61–7.76 (2H, two m)
 7.86, 8.12, 8.20, 8.27 (4H, four d)
 8.89 (1H, d, J=8.8Hz)

Example 116

N-Acetyl-L-phenylalanine

After 4.96 g of L-phenylalanine was dissolved in 5% sodium hydrogencarbonate aqueous solution, 3.4 ml of acetic anhydride was dropwise added to the solution over an hour under ice cooling. After completion of the dropwise addition, the mixture was stirred for 2 hours at room temperature. Then 17 ml of hydrochloric acid was added to the reaction mixture to render the system acidic. The precipitated white solid was extracted once with 100 ml of ethyl acetate and twice with 40 ml each of the same solvent. The oily layer was dried over anhydrous sodium sulfate and the solvent was distilled off to give 5.61 g of N-acetyl-L-phenylalanine as white crystalline powders. Yield, 90.3%.

melting point: 170–171° C.

$[\alpha]_{25/D}$ +45.7° (c=4.00, ethanol)

Example 117

N-Cyclohexyl-2-hydroxy-2-[2-(1-(N-acetylphenylalanyl)pyrrolidinyl)]acetamide

To 109.9 mg of N-cyclohexyl-2-hydroxy-2-[2-(1-phenylalanylpyrrolidinyl)]acetamide were added 110.5 mg of N-acetylphenylalanine, 131.2 mg of 1-hydroxybenzotriazole and 2 ml of DMF. Under ice cooling, 130.5 mg of 1-ethyl-3-(3-dimethylaminopropyl)carbodiimide hydrochloride was added to the solution. Thereafter the reaction mixture was stirred for 2 hours and at room temperature for further 5 hours. The reaction solution was then diluted with 20 ml of ethyl acetate. The diluted solution was washed successively with 15 ml each of 4% sodium hydrogencarbonate aqueous solution, 10% citric acid aqueous solution and saturated sodium chloride aqueous solution. The organic layer was dried over anhydrous sodium sulfate and concentrated under vacuum to give an amorphous solid. The solid was purified by column chromatography (silica gel, developed with dichloromethane-methanol) to give 173.6 mg of the title compound as a colorless amorphous solid. Yield, 86.0%.

FAB-MS m/z 416 (M+1)$^+$

Example 118

N-Cyclohexyl-2-oxo-2-[2-(1-(N-acetylphenylalanyl)pyrrolidinyl)]acetamide

To 173.3 mg of N-cyclohexyl-2-hydroxy-2-[2-(1-(N-acetylphenylalanyl)pyrrolidinyl)]acetamide were added 0.79 ml of acetic anhydride and 1.0 ml of DMSO. The mixture was stirred at room temperature for 24 hours. At the end of the reaction, 20 ml of water was added to the reaction solution. The aqueous layer was extracted 3 times with 10 ml each of dichloromethane. The oily layer was dried over anhydrous sodium sulfate and concentrated under vacuum to give 772 mg of an oily substance. The oily substance was purified by column chromatography (silica gel, developed with dichloromethane-acetonitrile) to give 119.9 mg of the title compound as an amorphous solid. Yield, 69.5%.

melting point: 94–96.5° C.

$[\alpha]25/D$–30.1° (c 1.00, CHCl$_3$)

FAB-MS m/z 414 (M+1)$^+$

1H-NMR (CDCl$_3$) δ:
  1.11–1.48 (5H, m)
  1.55, 2.05 (8H, m)
  1.92 (3H, s)
  2.32 (1H, m)
  2.94 (1H, dd, J=6.4, 13.7Hz)
  ca. 3.06 (1H, m, overlapping)
  3.08 (1H, dd, J=7.3, 13.7Hz)
  3.46 (1H, m)
  3.75 (1H, m)
  4.96 (1H, ddd, J=6.4, 7.3, 8.3Hz)
  5.33 (1H, dd, J=6.1, 8.5Hz)
  6.36 (1H, d, J-8.3Hz)
  6.78 (1H, d, J=8.3Hz)
  7.15–7.40 (5H, m)

Example 119

(S)-2-Acetylamino-3-cyclohexylpropionic acid

After 4.03 g of N-acetyl-L-phenylalanine was dissolved in 50 ml of methanol, 0.41 g of 5% rhodium/alumina was added to the solution. The mixture was reduced for 23 hours with a low-pressure hydrogenator under an initial hydrogen pressure of 2.5 kg/cm$^2$ (approximately 30% reaction, confirmed by TLC). Then 0.40 g of the catalyst was supplemented and reduction was similarly carried out for 20 hours (approximately 70% reaction, confirmed by TLC). Further 0.10 g of the catalyst was replenished and reduction was similarly performed for additional 13 hours. The catalyst was then filtered off through a funnel lined with celite. The solvent was distilled off from the filtrate. By drying using a vacuum pump, 4.07 mg of the product was obtained as a white crystalline solid. Yield, 98.1%.

melting point: 199–200° C.

$[\alpha]_{26/D}$ –4.4° (c=1.08, methanol)

FAB-MS m/z 212 (M–1)$^-$

1H-NMR (MeOH-d$_4$) δ:
  0.80–1.09 (2H, m)
  1.10–1.45 (4H, m)
  1.56 (1H, ddd, J=4.9, 10.3, 13.7Hz)
  ca. 1.60–1.85 (6H, m, overlapping)
  1.97 (1H, s)
  4.42 (1H, dd, J=4.9, 10.3Hz)

Example 120

(S)-2-Amino-3-cyclohexylpropionic acid hydrochloride

To 3.82 g of (S)-2-acetylamino-3-cyclohexylpropionic acid was added 100 ml of 7 N hydrochloric acid. As the reaction proceeded, the suspension changed to a homogeneous solution. After the reaction was completed, the solvent was distilled off to give 3.97 g of a crystalline solid. The solid was washed once with 20 ml of acetone and twice with 10 ml each of acetone to give 3.59 g of the product as needles. Yield, 96.6%.

melting point: 235–239° C. (decompd.)

$[\alpha]_{26/D}$ +20.2° (c=1.50, methanol)

FAB-MS m/z 172 (M-HCl+1)$^+$

Example 121

(S)-2-t-Butoxycarbonylamino-3-cyclohexylpropionic acid

In 90 ml of dioxane and 60 ml of water was suspended 3.00 g of (S)-2-amino-3-cyclohexylpropionic acid hydrochloride. Under ice cooling, 4.25 ml of triethylamine and 3.47 g of di-t-butyl dicarbonate were added to the suspension. The mixture was stirred at room temperature for 4.5 hours. As the reaction proceeded, the suspension changed to a homogeneous solution. The solvent was then distilled off under vacuum and 30 ml of water was added to the thus obtained white solid. The resulting solution was washed with 20 ml of ethyl acetate. By adding 3.0 ml of 5 N hydrochloric acid to the aqueous layer, the pH was made acidic (pH 2). The mixture was extracted twice with 20 ml each of ethyl acetate. The extracts were combined and washed with 20 ml of saturated sodium chloride aqueous solution. After drying over anhydrous sodium sulfate, the solvent was distilled off to give 3.06 g of (S)-2-t-butoxycarbonylamino-3-cyclohexylpropionic acid as a colorless transparent amorphous solid. On the other hand, 10 ml of water was added to the liquid previously obtained by washing with ethyl acetate. After the mixture was rendered acidic as shown above, extraction was performed with ethyl acetate and 0.92 g of the recovered syrup-like substance was purified by column chromatography (Sephadex LH-20, methanol) to give 0.86 g of the product. Yield, 100%.

melting point: 32–33° C.

$[\alpha]26/D$ –2.7° (c 1.10, $CHCl_3$)

FAB-MS m/z 270 (M–1)⁻

1H-NMR ($CDCl_3$) δ:
0.82–1.05 (2H, m)
1.06–1.33 (3H, m)
1.34–1.57 (2H, m, overlapping)
1.45 (9H, s)
1.58–1.89 (6H, m)
4.20, 4.34 (total 1H, m and br ddd)
4.87, 5.96 (total 1H, d, J=7.8Hz and br s)
8.58 (1H, br)

Example 122

N-Cyclohexyl-2-hydroxy-2-[2-(1-(N-t-butoxycarbonyl-β-cyclohexylalanyl)pyrrolidinyl)] acetamide To 101.7 mg of N-cyclohexyl-2-hydroxy-2-(2-pyrrolidinyl)acetamide were added 134.4 mg of (S)-2-t-butoxycarbonylamino-3-cyclohexylpropionic acid, 121.8 mg of 1-hydroxybenzotriazole and 2 ml of DMF. Under ice cooling, 120.8 mg of 1-ethyl-3-(3-dimethylaminopropyl) carbodiimide hydrochloride was added to the solution. After stirring for 2 hours, the reaction mixture was stirred at room temperature for further 6 hours. Then the reaction solution was diluted with 20 ml of ethyl acetate. The diluted solution was washed successively with 15 ml each of 4% sodium hydrogencarbonate aqueous solution, 10% citric acid aqueous solution and saturated sodium chloride aqueous solution. The organic layer was dried over anhydrous sodium sulfate and concentrated under vacuum to give an amorphous solid. The solid was purified by column chromatography (silica gel, developed with dichloromethane-methanol) to give 209.7 mg of the product as a colorless amorphous solid. Yield, 97.3%

FAB-MS m/z 480 (M+1)⁺

Example 123

N-Cyclohexyl-2-hydroxy-2-[2-(1-(N-(2-quinolylcarbonyl)β-cyclohexylalanyl)pyrrolidinyl) acetamide To 209.4 mg of N-cyclohexyl-2-hydroxy-2-[2-(1-(N-(t-butoxycarbonyl)-β-cyclohexylalanyl)pyrrolidinyl)] acetamide was added 2.0 ml of trifluoroacetic acid. After stirring at room temperature for 40 minutes, the solvent was distilled off and 2 ml of toluene was added to the residue followed by distilling off the solvent. This cycle of the procedures was repeated 3 times to give N-cyclohexyl-2-hydroxy-2-[2-(1-(β-cyclohexylalanyl)pyrrolidinyl)] acetamide trifluoroacetate. After 79.4 mg of quinaldinic acid and. 118.6 mg of 1-hydroxybenzotriazole were added to the thus obtained salt, the mixture was dissolved in 2.5 ml of DMF. Under ice cooling, 67 μl of triethylamine and 117.2 mg of 1-ethyl-3-(3-dimethylaminopropyl)carbodiimide hydrochloride were added to the solution. After stirring for 2 hours, stirring was continued at room temperature for further 5 hours. Thereafter, the reaction solution was diluted with 25 ml of ethyl acetate and the diluted solution was washed successively with 20 ml each of 4% sodium hydrogencarbonate aqueous solution and saturated sodium chloride aqueous solution. The organic layer was dried over anhydrous sodium sulfate and concentrated under vacuum to give 257 mg of an amorphous solid. The solid was purified by column chromatography (silica gel, developed with dichloromethane-methanol-triethylamine) to give 211.8 mg of the title compound as a colorless amorphous solid. Yield, 90.7%.

FAB-MS m/z 535 (M+1)⁺

Example 124

N-Cyclohexyl-2-oxo-2-[2-(1-(N-(2-quinolylcarbonyl)-β-cyclohexylalanyl)pyrrolidinyl)] acetamide To 186.5 mg of N-cyclohexyl-2-hydroxy-2-[2-(1-(N-(2-quinolylcarbonyl)-β-cyclohexylalanyl)pyrrolidinyl)] acetamide were added 34.5 mg of pyridine trifluoroacetate, 201.1 mg of 1-ethyl-3-(3-dimethylaminopropyl) carbodiimide hydrochloride and 2.0 ml of DMSO. The mixture was stirred at room temperature for 24 hours. At the end of the reaction, a sodium hydrogencarbonate solution (14.8 mg of sodium hydrogencarbonate dissolved in 20 ml of water) was added to the reaction solution. The solution was extracted 3 times with 10 ml each of dichloromethane. After washing with 15 ml of water, the oily layer was dried over anhydrous sodium sulfate and concentrated under vacuum to give a brown syrup-like substance. The substance was purified by column chromatography (silica gel, developed with dichloromethane-acetonitrile-acetic acid) to give 139.2 mg of the title compound as a colorless transparent amorphous solid. Yield, 74.9%.

melting point: 82–84° C.

$[\alpha]26/D$ –49.3° (c 1.22, $CHCl_3$)

FAB-MS m/z 533 (M+1)⁺

1H-NMR ($CDCl_3$) δ:
0.85–1.56 (11H, m)
1.57–2.17 (15H, m)
2.39 (1H, m)
3.66–3.80 (2H, m)
3.98 (1H, dt, J=6.4, 9.8Hz)
5.14 (1H, ddd, J=5.4, 9.3, 9.3Hz)
5.28 (1H, dd, J=6.6, 8.5Hz)
6.75 (1H, d, J=8.3Hz)
7.60, 7.76 (2H, two m)
7.86, 8.13, 8.25, 8.29 (4H, four d)
8.71 (1H, d, J=9.3Hz)

Reference Example 4

N-(N-(3-Phenoxybenzoyl)-L-phenylalanyl)-L-prolinal

To 216.4 mg of N-(N-(3-phenoxybenzoyl)-L-phenylalanyl)-L-prolinol were added 0.92 ml of acetic anhydride-and 2.6 ml of DMSO. The mixture was stirred at room temperature for 22 hours. Then 40 ml of water was added to the reaction mixture. After stirring for an hour, the mixture was extracted 3 times with 20 ml each of dichloromethane. The oily layer was dried over anhydrous sodium sulfate and the solvent was distilled off to give 248.7 mg of an oily substance. The oily substance was purified by column chromatography (silica gel, developed with hexane-ethyl acetate) to give 85.5 mg of an amorphous solid. The solid was further purified by column chromatography (silica gel, developed with dichloromethane-ethyl acetate) to give 46.4 mg of the title compound as a colorless transparent amorphous solid. Yield, 21.5%.

FAB-MS m/z 443 (M+1)⁺

1H-NMR (CDCl₃) δ:
 1.71 (1H, m)
 1.77–1.93 (2H, m)
 1.97 (1H, m)
 2.98 (1H, m)
 3.17 (1H, dd, J=7.8, 13.2Hz)
 3.20 (1H, dd, J=6.4, 13.2Hz)
 3.70 (1H, dt, J=6.6, 10.3Hz)
 4.40 (1H, m)
 5.15 (1H, ddd, J=6.4, 7.8, 7.8Hz)
 7.01 (2H, m)
 7.13 (3H, m)
 7.18–7.50 (10H, m)

The prolyl endopeptidase inhibition activity of the product: IC$_{50}$ 0.11 μg/ml Example 125

N-Cyclohexyl-2-hydroxy-2-[2-(1-(1-t-butoxycarbonyl-2,3-dihydroindole-2-carbonyl)pyrrolidinyl)]acetamide In 3 ml of DMF were dissolved 162 mg of N-cyclohexyl-2-hydroxy-2-(2-pyrrolidinyl)acetamide hydrochloride, 198.1 mg of 1-t-butoxycarbonyl-2,3-dihydroindole-2-carboxylic acid and 126.1 mg of 1-hydroxybenzotriazole. Under ice cooling, 103.6 μl of triethylamine and 141.1 mg of 1-ethyl-3-(3-dimethylaminopropyl)carbodiimide hydrochloride were added to the solution. After stirring for 2 hours, the reaction mixture was stirred at room temperature for further 18 hours. Then the reaction mixture was diluted with 25 ml of ethyl acetate. The diluted mixture was washed in succession with 10% citric acid aqueous solution, 4% sodium hydrogencarbonate aqueous solution, distilled water and saturated sodium chloride aqueous solution. The organic layer was dried over anhydrous sodium sulfate and concentrated under vacuum to give 313 mg of N-cyclohexyl-2-hydroxy-2-[2-(1-(1-t-butoxycarbonyl-2,3-dihydroindole-2-carbonyl)pyrrolidinyl)]acetamide as a colorless solid.

FAB-MS m/z 472 (M+1)⁺

Example 126

N-Cyclohexyl-2-oxo-2-[2-(1-(1-t-butoxycarbonyl-2,3-dihydroindole-2-carbonyl)pyrrolidinyl)]acetamide After 82.0 mg of N-cyclohexyl-2-hydroxy-2-[2-(1-(1-t-butoxycarbonyl-2,3-dihydroindole-2-carbonyl)pyrrolidinyl)]acetamide was dissolved in 1 ml of DMSO, 0.6 ml of acetic anhydride was added to the solution followed by stirring for 18 hours. Then 20 ml of 4% sodium hydrogencarbonate aqueous solution was added thereto. After stirring for 15 minutes, the reaction mixture was extracted twice with 20 ml each of ethyl acetate. The extract was washed in succession with 20 ml each of 4% sodium hydrogencarbonate aqueous solution, distilled water and saturated sodium chloride aqueous solution. The organic layer was dried over anhydrous sodium sulfate and concentrated under vacuum to give 76.4 mg of a colorless solid. The solid was dissolved in methylene chloride and the solution was purified by silica gel column chromatography (methylene chloride-methanol) to give 69.4 mg of N-cyclohexyl-2-oxo-2-[2-(1-(1-t-butoxycarbonyl-2,3-dihydroindole-2-carbonyl)pyrrolidinyl)]acetamide as a colorless amorphous solid. Yield, 77.0%

FAB-MS m/z 470 (M+1)⁺

Industrial Applicability

According to the present invention, there are obtained novel keto-acid amide derivatives represented by formula (1) which possess a potent prolyl endopeptidase activity and are thus expected to be useful as an active ingredient of a drug for the treatment of amnesia and systemic lupus erythematosus. In these novel keto-acid amide derivatives, it is unnecessary to retain peptide residues or amino acid residues, which might be degraded by various proteases in vivo, in order to enhance the C-terminal specificity in the keto-acid structure. The prolyl endopeptidase activity of the compounds of the present invention is also confirmed in vivo.

We claim:

1. A pyrrolidine represented by formula (3):

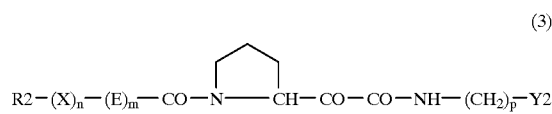

(3)

wherein:

represents a 3- to 15-membered mono- or fused cyclic hydrocarbon group, a pyridyl group or a morpholino group, each of which nay be substituted with a substituent(s) selected from the group consisting of a lower alkyl group, a lower alkoxy group, phenoxy, methylenedioxy, a halogen atom, hydroxy, mercapto, in alkylthio group, nitro and a mono- and di-lower alkylamino group;

each of n and m represents an integer and the sum of n and m is an integer of 0 to 2;

each of X and E represents oxygen, NR' (wherein R' is hydrogen or a lower alkyl group having 1 to 6 carbon atoms), sulfur, phenylene, CH=CH or CH$_2$;

p represents air integer of 1 to 3; and,

Y2 represents a pyridyl group or a morpholino group, each of which may be substituted with a substituent(s) selected from the group consisting of a lower alkyl group, a lower alkoxy group, phenoxy, methylenedioxy, a haloen atom, hydroxy, mercapto, an alkyltio group, nitro and a mono- and di-lower-alkylamino group;

or a salt thereof.

2. A compound according to claim 1 or a salt thereof, wherein R2—(X)n—(E)m—CO— represents phenoxyacetyl, phenylthioacetyl, pyridylthioacetyl, pyridylcarbonyl, pyridylacetyl, morpholinomethylbenzyl, phenoxybenzoyl, naphthoyl, or cinnamoyl; and Y2 represents a monovalent group from pyridyl or morpholino.

3. A compound according to claim 1 or a salt thereof, wherein R2—(X)n—(E)m—CO— represents pyridylthioacetyl or pyridylcarbonyl; and Y2 represents a monovalent group from pyridyl or morpholino.

4. A pyrrolidine represented by formula (4):

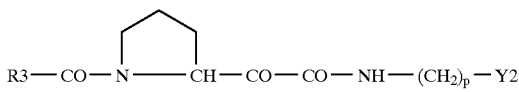

(4)

wherein
R3 represents a phenyl group which may be substituted with a substituent(s) selects from the group consisting of a lower alkyl group, a lower alkoxy group, phenoxy, methylenedioxy, a halogen atom, hydroxy, mercapto, an alkylthio group, nitro and a mono- and di-lower alkylamino group;
p represents an integer of 1 to 3; and,
Y2 represents a pyridyl group or a morpholino group, each of which may be substituted with a substituent(s) selected from the group consisting of a lower alkyl group, a lower alkoxy group, phenoxy, methylenedioxy, a halogen atom, hydroxy, mercapto, an alkylthio group, nitro and a mono- and di-lower alkylamino group;
or a salt thereof.

5. A compound according to claim 4 or a salt thereof, wherein R3 represents a phenyl group which may be substituted with a substituent(s) selected from the group consisting of a lower alkyl group, a lower alkoxy group, phenoxy, methylenedioxy, a halogen atom, hydroxy, mercapto, an alkylthio group, nitro and a mono- and di-lower alkylamino group; and Y2 represents a monovalent group from pyridyl or morpholino.

6. A pyrrolidine represented by formula (1):

(1)

wherein:
R1 represents a pyridyl group or a morpholino group, each of which may be substituted with a substituent(s) selected from the group consisting of a lower alkyl group, a lower alkoxy group, phenoxy, methylenedioxy, a halogen atom, hydroxy, mercapto, an alkylthio group, nitro and a mono- and di-lower alkylamino group;
each of n and m represents an integer and the sum of n and m is an integer of 0 to 2;
each of X and E represents oxygen, NR' (wherein R' is hydrogen or a lower alkyl group having 1 to 6 carbon atoms), sulfur, phenylene, CH=CH or $CH_2$;
A represents an amino acid residue or an amino acid residue, which functional group may be optionally protected, or a glycine residue which may be substituted at the amino moiety thereof with a substituent selected from the group consisting of glycine, sarcosine, N-benzylycine, N-cyclohexylglycine, N-cyclohexylnmethylglycine, N-isopropylglycine and N-isobutylglycine; and
Y1 represents a cycloalkyl group having 3 to 8 carbon atoms;
or a salt thereof.

7. A compound according to claim 6 or a salt thereof, wherein R1—(X)n—(E)m—CO— represents pyridylthioacetyl, pyridylacetyl, morpholinomethylbenzoyl, pyridylacryloyl or pyridylcarbonyl; and A represents phenylalanine, homophenylalanine, valine, leucine, isoleucine, alanine, β-cyclohexylalanine; an optionally protected lysine, ornithine, arginine, serine, homoserine, threonine, methionine, aspartic acid, glutamic acid, proline, hydroxyproline, glycine, sarcosine, N-benzylglycine, N-cyclohexylglycine, N-cyclohexylmethylglycine, N-isopropylglycine, N-isobutylglycine or dihydroindole-2-carbonyl.

8. A compound according to claim 6 or a salt thereof, wherein R1—(X)n—(E)m—CO— represents pyridylthioacetyl, pyridylacetyl, morpholinomethylbenzoyl, pyridylacryloyl or pyridylcarbonyl: and A represents phenylalanine, homophenylalanine, valine, leucime, isoleucine, N-benzylglycine, proline, β-cyclohexylalanine or dihydroindole-2-carbonyl.

9. N-cyclohexyl-2-oxo-2-[2-(1-(N-(2-pyridylcarbonyl)phenylalanyl)pyrrolidinyl)]acetamide or a salt thereof.

10. A compound according to claim 8 or a salt thereof, wherein A represents phenylalanine, valine, N-benzylglycine, proline, β-cyclohexylalanine or dihydroindole-2-carbonyl.

11. A pyrrolidine represented by formula (2):

(2)

wherein:
R2 represents a pyridyl group or a morpholino group, each of which may be substituted with a substituent(s) selected from the group consisting of a lower alkyl group, a lower alkoxy group, phenoxy, methylenedioxy, a halogen atom, hydroxy, mercapto, an alkylthio group, nitro and a mono- and di-lower alkylamino group;
each of n and m represents an integer and the sum of n and m is an integer of 0 to 2;
each of X and B represents oxygen, NR' (wherein R' is hydrogen or a lower alkyl group having 1 to 6 carbon atoms), sulfur, phenylene, CH=CH or $CH_2$; and,
Y1 represents a cycloalkyl group having 3 to 8 carbon atoms: or a salt thereof.

12. A pyrrolidine according to claim 11 or a salt thereof, wherein R2—(X)n—(E)m—CO— represents pyridylthioacetyl, pyridylacetyl, morpholinomethuylbenzoyl, pyridylcarbonyl, or pyridylacryloyl.

13. A pyrrolidine according to claim 11 or a salt thereof, wherein R2—(X)n—(E)m—CO— represents morpholinomethylbenzoyl, pyridylcarbonyl or pyridylacryloyl.

14. A pharmaceutical composition comprising a pyrrolidine or a salt thereof according to any one of claims 1, 4, 6, or 11 together with a suitable pharmaceutical carrier.

15. A method for inhibiting the activity of serine protease or thiol protease which comprises administering to a mammal an effective dose of the pyrrolidine derivative or a salt thereof according to any one of claims 1, 4, 6, or 11.

16. N-Cyclohexyl-2-oxo-2-[2-(1-4-(morpholinomethylbenzoyl)pyrrolidinyl)]acetamide or a salt thereof.

* * * * *